(12) United States Patent
Nam et al.

(10) Patent No.: US 9,274,117 B2
(45) Date of Patent: Mar. 1, 2016

(54) USE OF SIRT7 AS NOVEL CANCER THERAPY TARGET AND METHOD FOR TREATING CANCER USING THE SAME

(71) Applicant: Catholic University Industry Academic, Seoul (KR)

(72) Inventors: Suk-Woo Nam, Seoul (KR); Jeong-Kyu Kim, Sungnam-si (KR)

(73) Assignee: CATHOLIC UNIVERSITY INDUSTRY ACADEMIC, Seoul (KR)

( * ) Notice: Subject to any disclaimer, the term of this patent is extended or adjusted under 35 U.S.C. 154(b) by 0 days.

(21) Appl. No.: 14/138,035

(22) Filed: Dec. 21, 2013

(65) Prior Publication Data

US 2015/0177248 A1  Jun. 25, 2015

(51) Int. Cl.
| | |
|---|---|
| *C12N 15/11* | (2006.01) |
| *G01N 33/574* | (2006.01) |
| *C12N 15/113* | (2010.01) |
| *C12Q 1/68* | (2006.01) |
| *A61K 48/00* | (2006.01) |

(52) U.S. Cl.
CPC ...... *G01N 33/57438* (2013.01); *C12N 15/1137* (2013.01); *C12Q 1/6886* (2013.01); *A61K 48/00* (2013.01); *C12N 2310/14* (2013.01); *C12N 2310/141* (2013.01); *C12N 2320/11* (2013.01); *C12Q 2600/158* (2013.01); *C12Y 305/01098* (2013.01); *G01N 2500/10* (2013.01)

(58) Field of Classification Search
CPC .............................. A61K 48/00; C12N 15/113
See application file for complete search history.

(56) References Cited

U.S. PATENT DOCUMENTS

| | | | |
|---|---|---|---|
| 5,138,045 A | 8/1992 | Cook et al. | |
| 5,218,105 A | 6/1993 | Cook et al. | |
| 5,459,255 A | 10/1995 | Cook et al. | |
| 2011/0212965 A1* | 9/2011 | Frechette et al. | 514/237.2 |
| 2013/0072421 A1* | 3/2013 | Collard et al. | 514/1.6 |

FOREIGN PATENT DOCUMENTS

| | | |
|---|---|---|
| WO | 9907409 A1 | 2/1999 |
| WO | 9932619 A1 | 7/1999 |
| WO | 0044895 A1 | 8/2000 |
| WO | 0044914 A1 | 8/2000 |
| WO | 0129058 A1 | 4/2001 |
| WO | 0136646 A1 | 5/2001 |

OTHER PUBLICATIONS

Bjersing, L., et al., "Easy detection of mutations in acute intermittent porphyria and hepatocellular carcinoma on paraffin-embedded tissue", "Journal of Internal Medicine", 1993, pp. 339-340, vol. 234.
Clackson, T., et al., "Making antibody fragments using phage display libraries", "Nature", Aug. 15, 1991, pp. 624-628, vol. 352.
Hui, A., et al., "Cell cycle regulators and human hepatocarcinogenesis", "Hepatogastroenterology", Sep.-Oct. 1998, pp. 1635-1642 (Abstract), vol. 45, No. 23.
Keck, C., et al., "Nonrandom Breakpoints of Unbalanced Chromosome Translocations in Human Hepatocellular Carcinoma Cell Lines", "Cancer Genet Cytogenet", 1999, pp. 37-44, vol. 11.
Kim, J., et al., "Sirtuin7 Oncogenic Potential in Human Hepatocellular Carcinoma and Its Regulation by the Tumor Suppressors MiR-125a-5p and MiR-125b", "Hepatology", Mar. 2013, pp. 1055-1067, vol. 57, No. 3.
Kusano, N., et al., "Genetic Aberrations Detected by Comparative Genomic Hybridization in Hepatocellular Carcinomas: Their Relationship to Clinicopathological Features", "Hepatology", 1999, pp. 1858-1862, vol. 29, No. 6.
Marks, J., et al., "By-passing Immunization Human Antibodies from V-gene Libraries Displayed on Phage", "J. Mol. Biol.", 1991, pp. 581-597, vol. 222.
Park, W., et al., "Somatic Mutations in the Kinase Domain of the Met/Hepatocyte Growth Factor Receptor Gene in Childhood Hepatocellular Carcinomas", "Cancer Research", Jan. 15, 1999, pp. 307-310, vol. 59.
Tsopanomichalou, M., et al., "Loss of heterozygosity and microsatellite instability in human non-neoplastic hepatic lesions", "Liver", Aug. 1999, pp. 305-311 (Abstract), vol. 19, No. 4.

* cited by examiner

*Primary Examiner* — Brian Whiteman
(74) *Attorney, Agent, or Firm* — Hultquist, PLLC; Steven J. Hultquist

(57) ABSTRACT

The use of SIRT7 (sirtuin 7) as a marker for diagnosis of liver cancer is described. The disclosure variously relates to a liver cancer diagnostic marker including SIRT7 gene, a liver cancer diagnostic composition, a kit and microarray including the same, and a method of diagnosing liver cancer using the same. Also described is a method for screening a substance capable of treating liver cancer by inhibiting the expression of SIRT7 gene or protein, and a composition for preventing or treating liver cancer, which includes such substance. The disclosure further relates to the use of SIRT7 gene as a cancer diagnostic marker and the anticancer use of inhibition of SIRT7 expression, as well as the use of the specific miRNA to regulate the cell cycle and inhibit tumor growth by the expression of SIRT7 gene.

3 Claims, 17 Drawing Sheets

USE OF SIRT7 AS NOVEL CANCER THERAPY TARGET AND METHOD FOR TREATING CANCER USING THE SAME

TECHNICAL FIELD

The present invention relates to a novel cancer diagnostic marker capable of effectively diagnosing and predicting cancer in an early stage, a composition for cancer diagnosis, a kit for cancer diagnosis, a microarray for cancer diagnosis, and a method of diagnosing or prognosing cancer using the cancer diagnostic marker.

Moreover, the present invention is based on the finding that the expression of SIRT7 gene is indicative of the development and proliferation of cancer cells. Thus, the present invention is directed to specific endogenous miRNA that regulate the expression of SIRT7, and more particularly to a method of treating cancer by targeting cancer cells with miR-125a-5p and miR-125b, which are miRNAs that regulate the expression of SIRT7 and have the abilities to regulate the cell cycle and inhibit tumor growth.

BACKGROUND ART

Hepatocellular carcinoma (HCC) is the fifth most common tumor worldwide and accounts for 500,000 deaths each year (Okuda 2000). The survival rate of HCC patients has not been improved over the past 20 years, with the incidence rate almost equal to the death rate (Marrero, Fontena et al. 2005). The known major risk factors for HCC are chronic hepatitis resulting from infection with hepatitis B virus or hepatitis C virus and exposure to carcinogens such as aflatoxin B1 (Thorgeireson and Grisham 2002).

It was reported that the change in cell cycle regulators that proceed to the GI phase in the cell cycle leads to hepatocarcinogenesis [Hui et al., Hepatogasteroenterology 45:1635-1642, 1998]. In addition, it was reported that DNA mutations and genetic alterations in gene expression are found in the tissue of liver cancer patients [Park et al., Cancer Res. 59:307-310, 1999; Bjersing et al., J. Intern. Med. 234:339-340, 1993; Tsopanomichalou et al., Liver 19:305-311, 1999; Kusano et al., Hepatology 29:1858-1862, 1999; Keck et al., Cancer Genet. Cytogenet. 111:37-44, 1999].

Thus, it can be seen that the development and progression of cancer is not caused by some specific genes, but results from complex interactions between many genes that are involved in various intracellular signaling mechanisms and regulatory mechanisms which occur during the progression of cancer. Accordingly, it is very significant to identify new liver cancer-related genes by comparatively analyzing the expression levels of a large number of genes between normal liver cells and liver cancer cells, rather than studying mechanisms of hepatocarcinogenesis on the basis of some specific genes.

Recent molecular studies revealed that genetic alterations of tumor suppressor genes or oncogenes, such as p53, beta-catenin and AXIN1, can be associated with the progression of HCC (de La Coste, Romagnolo et al. 1998; Satoh, Daigo et al. 2000; Pang, Ng et al. 2003). However, it is unclear whether such genetic alterations are reflected in the clinical characteristics of tumors of individuals. Thus, reliable molecular studies on HCC in most patients still remain challenges (Nam, Park et al. 2005).

Accordingly, the present inventors have analyzed the expression level of the SIRT7 gene in cancer tissues, and as a result, have identified a cancer diagnostic marker that expresses SIRT7, as well as specific miRNAs that function to regulate the expression of SIRT7. The present inventors have also found that the miRNAs have the abilities to regulate the cell cycle and inhibit tumor growth caused by promoter methylation, and thus can be used as a cancer therapeutic target, thereby completing the present invention.

DISCLOSURE OF INVENTION

It is an object of the present invention to provide a cancer diagnostic marker comprising a substance for measuring the level of SIRT7 gene or the level of SIRT7 protein.

Another object of the present invention is to provide a cancer diagnostic kit and a cancer diagnostic microarray, which comprise the above cancer diagnostic marker.

Still another object of the present invention is to provide a method for diagnosing or prognosing cancer, the method comprising a step of measuring the expression level of SIRT7 gene or the level of SIRT7 protein.

Still another object of the present invention is to provide a method for screening a substance capable of preventing or treating cancer.

Still another object of the present invention is to provide a pharmaceutical composition for preventing or treating cancer, the composition comprising a substance for inhibiting the expression of SIRT7 gene.

Still another object of the present invention is to provide a method for diagnosing or prognosing cancer, the method comprising examining the expression profiling of miR-125a-5p or miR-125b on the basis of the relationship between cancer marker SIRT7 and specific miRNA miR-125a-5p or miR-125b.

Still another object of the present invention is to provide a method for treating SIRT7-expressing cancer by administering an anticancer composition against the cancer, wherein the anticancer composition comprises, as an active ingredient, an agent for promoting the expression or activity of miR-125a-5p or miR-125b.

Still another object of the present invention is to provide a method for screening a substance for treating a liver cancer, in which the expression of miR-125a-5p or miR-125b is inhibited.

Still another object of the present invention is to provide the novel use of miR-125a-5p or miR-125b. which is a specific miRNA that controls the expression of liver cancer marker SIRT7.

In one embodiment, the present invention provides a method of diagnosing or prognosing SIRT7-expressing cancer by examining the expression profiling of miR-125-5p or miR-125b.

Herein, the SIRT7-expressing cancer may be at least one liver cancer selected from the group consisting of hepatocellular carcinoma (HCC), biliary duct cancer, and metastatic liver cancer. More preferably, the cancer is hepatocellular carcinoma (HCC). Further, miR-125a-5p may have a nucleotide sequence of 5'-ucccugagacccuuuaaccaguga-3' (SEQ ID NO: 7), and miR-125b may have a nucleotide sequence of 5'-ucccugagacccuaacuuguga-3' (SEQ ID NO: 8).

Still another object of the present invention is to provide a method of treating SIRT7-expressing cancer by administering an anticancer composition against the cancer, wherein the composition comprises, as an active ingredient, an agent for promoting the expression or activity of miR-125a-5p or miR-125b. Herein, the agent for promoting the expression or activity of miR-125a-5p or miR-125b may be a vector encoding miR-125a-5p or miR-125b, a hypermethylation inhibitor, or a p53 activator.

Particularly, the above composition may have the effect of transfecting SIRT7-expressing cancer cells so as to cause miR-125a-5p or miR-125b to bind to SIRT7 mRNA 3'UTR to thereby inhibit the expression of SIRT7. The composition may comprise a cationic lipid or cationic amphipathic substance that facilitates intracellular release of the composition.

The above composition has the effect of arresting the cell cycle at G1/S phase to delay the growth of cancer cells. Thus, the composition is useful as an anticancer agent.

Yet another object of the present invention is to provide a method of regulating the expression of SIRT7 using a miRNA such as miR-125a-5p or miR-125b.

This method may comprise either a step of bringing SI1RT7 into contact with a miRNA such as miR-125a-5p or miR-125b, or a step of bringing SIRT7 into contact with a vector encoding miR-125a-5p that targets the SIRT7 gene. Herein, an anticancer effect can be exhibited by a method of inhibiting the expression of SIRT7 gene by overexpressing or activating miR-125a-5p or miR-125b. For this purpose, it is preferable to inhibit promoter methylation or induce p53 activation.

The present invention also provides a method for screening a substance for treating liver cancer, the method comprising the steps of:

(a) treating an animal cell, which expresses miR-125a-5p or miR-125b, with an anticancer candidate substance; and (b) selecting the candidate substance as the substance for treating liver cancer when the expression of miR-125a-5p or miR-125b in the animal cell is increased compared to a control group not treated with the candidate substance.

As described above, the present invention is directed to a cancer diagnostic marker comprising a substance for measuring the level of SIRT7 gene or SIRT7 protein, and to the use of miR-125a-5pb or miR-125b as a target for diagnosing and treating SIRT7-related cancer.

BRIEF DESCRIPTION OF THE DRAWINGS

FIG. 1A shows the results of microarray analysis of the expression level of SIRT7 mRNA in LGDN (low-grade dysplastic nodule), HGDN (high-grade dysplastic nodule), G1-G3 (Edmondson grade I, II, III); FIG. 1B shows the results of comparatively analyzing the expression levels of SIRT7 in liver cancer tissue and normal tissue; FIG. 1C shows the results of Western blot analysis of whether or not SIRT7 is expressed in hepatocellular carcinoma (HCC) tissues (T) and normal tissues (N) surrounding cancer cells; and FIGS. 1D to 1F show the results of MTT assay for the cell viabilities of the Hep3B, SNU-368 and SNU-449 cells treated with SIRT7 si-RNA and a control group treated with si-Cont.

FIG. 2A shows the results of analyzing the SIRT7 siRNA-mediated change in the cell cycle by treatment with nocodazole; FIG. 2B shows the results of Western blot analysis performed to examine the influence of SIRT7 on the expressions of the cell cycle regulators p21 and cyclin D1; and FIG. 2C shows experimental results indicating that SIRT7 can regulate the growth of hepatocellular carcinoma (HCC) by cell cycle regulatory proteins and autophagy-related proteins.

FIG. 4A shows the decrease in number of liver cancer cells caused by treatment with SIRT7 si-RNA, and FIG. 4B shows the decrease in tumor volume in liver cancer mouse models caused by injection with SIRT7 si-RNA.

FIGS. 5A and 5B shows microarray analysis data in several HCC groups, FIG. 5C shows western blot analysis performed to examine the expression of SIRT7 in 10 randomly selected human HCC tissues, FIG. 5D shows Kaplan-Meier survival curve of HCC patients with high SIRT7 expression or low SIRT7 expression and FIGS. 5E to 5F show SIRT7 knockdown resulted in a significant decrease in the expression of SIRT7 protein and also resulted in a decrease in the proliferation rate of Hep3B, SNU-368 and SNU-449 liver cancer cells.

FIGS. 6A and 6B shows microarray analysis data in several HCC groups and FIG. 6C is Western blot analysis data which shows human liver cancer cell lines also have high expression levels of the SIRT7 protein compared to normal liver cell lines LO2, MiHA and THLE-3.

FIG. 7A shows SIRT7 knockdown resulted in a significant increase in liver cancer cells at G1/S phase and delayed cell cycle transition by Flow cytometry measurement, FIG. 7B shows inactivation of SIRT7 in Hep3B cells selectively induced the expression of p21$^{WAF1/Cip1}$ and, at the same time, inhibited the expression of cyclin D1 among G1/S cell cycle regulatory proteins by western blot analysis, FIG. 7C shows the inactivation of SIRT7 in Hep3B cells induced the expression of pro-autophagic protein Beclin-1 and conversion to LC3B-II by western blot analysis, FIG. 7D is western blot analysis data shows that the SIRT7 expressed in the nuclear fraction of Hep3B cells is a nucleolar sirtuin of liver cancer cells and FIG. 7E is western blot analysis data of ectopic plasimds expression which encode HDAC1, HAC2, p53 and HDAC6 in Hep3B cells.

FIGS. 8A and 8C shows WGS results which are transcriptionally silenced by oncogenic gene SIRT7 and FIG. 8B shows inactivation of SIRT7 in Hep3B cells selectively induced the expression of p21$^{WAF1/Cip1}$ and, at the same time, inhibited the expression of cyclin D1 among G1/S cell cycle regulatory proteins by western blot analysis

FIGS. 10A and 10B shows miRNA identification data which target SIRT7 gene, FIG. 10C shows miRNA microarray analysis data and FIG. 10D shows RT-PCR analysis data of five miRNAs in HCC cells and normal cells.

FIG. 11A shows vector construction related to SIRT7 3-UTR and random mutated 3-UTR, SIRT7 wt of the upper panel of FIG. 11A means 3'UTR region(312-335) of the wild type SIRT7 as described as SEQ ID NO: 47, SIRT7 mt of the upper panel of FIG. 11A means 3'UTR region(312-335) of the randomly mutated SIRT7 by using primer of SEQ ID NO: 11 and SEQ ID NO: 12 as described as SEQ ID NO: 48, SIRT7 wt of the middle panel of FIG. 11A means 3'UTR region(138-160) of the wild type SIRT7 as described as SEQ ID NO: 49, SIRT 7 mt of the middle panel of FIG. 11A means 3'UTR region(138-160) of the randomly mutated SIRT7 by using primer of SEQ ID NO: 13 and SEQ ID NO: 14 as described as SEQ ID NO: 50 and SIRT 7 wt of the down panel of FIG. 11A means 3'UTR region(307-328) of the wild type SIRT7 as described as SEQ ID NO: 51, SIRT 7 mt of the down panel of FIG. 11A means 3'UTR region(307-328) of the randomly mutated SIRT7 by using primer of SEQ ID NO: 15 and SEQ ID NO: 16 as described as SEQ ID NO: 52 and FIGS. 11B and 11C shows GEO data base analysis of the expression of miR-125a-5p and miR-125-b.

FIGS. 12A and 12B show dual-luciferase reporter analysis of five miRNAs, FIGS. 12C and 12D show endogenous expression level of five miRNAs in HCC cells and FIGS. 12E and 12F show western blot analysis data of inhibition of SIRT7 expression by the five miRNAs.

FIGS. 13A and 13B show MTT analysis that the ectopic expression of miR-125a-5p and miR-125b significantly inhibited the growth of both Hep3B and SNU-449 cell lines, FIGS. 13C and 13D show that only miR-125a-5p and miR-125b induced G1 arrest, unlike corresponding control groups (scramble sequences of miRNA) or other miRNAs (miR-148a and miR-152) and FIG. 13E shows Quantitative analysis of G1 phase of cells expressing miR-125a-5p, miR-125b or other miRNAs.

FIG. 15A shows western blot analysis data of promoter methylation in HCC and normal cell lines and FIGS. 15B to 15E show qRT-PCR analysis which showed that the endogenous expression of miR-125a-5p and miR-125b in Hep3B and SNU-449 cells was induced by ectopic p53 expression, 5-aza-dC treatment and the knockdown of DNMT1 and DNMT3b.

FIGS. 16A to 16D show qRT-PCR analysis which showed that the endogenous expression of miR-125a-5p and miR-125b in Hep3B and SNU-449 cells was induced by ectopic p53 expression, 5-aza-dC treatment and FIGS. 16E and 16F is western blot analysis data of SIRT7 expression level according to siRNA, p53, DMSO and 5-aza-dC treatment.

FIG. 17A is western blot analysis data for human HCCs compared to the adjacent non-tumor tissue, FIGS. 17B and 17C show the endogenous expression of miR-125a-5p and miR-125b in human HCCs which was analyzed by qRT-PCR, FIG. 17D shows DNA-binding motif of p53 gene sequencing results and FIG. 17E is western blot analysis data for promoter methylation of miR-125b.

DETAILED DESCRIPTION

Figure 1:
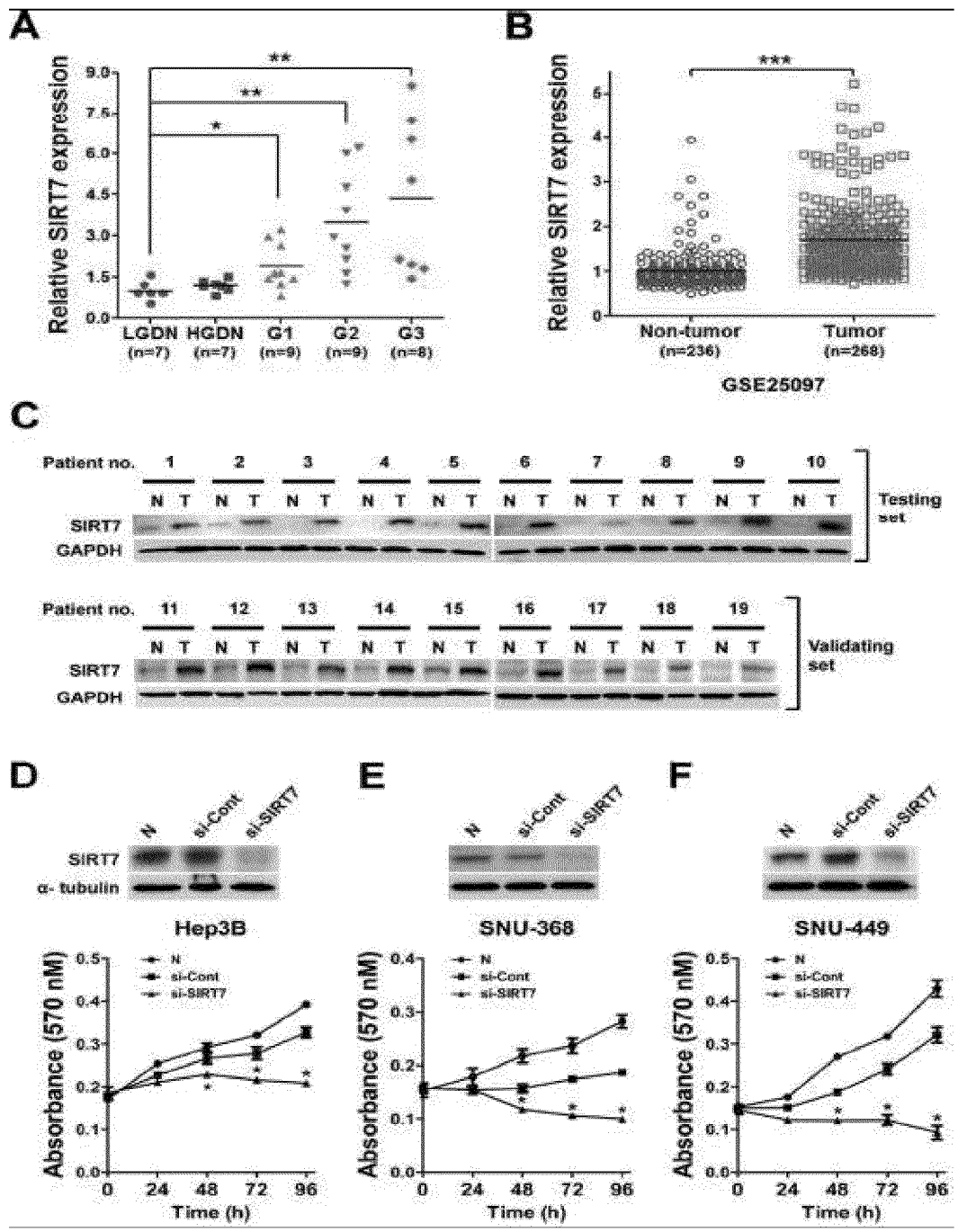
FIG. 1 shows the results of examining the relationship between human hepatocellular carcinoma (HCC) and SIRT7 expression.

The present invention provides a novel cancer diagnostic marker including SIRT7 gene or SIRT7 protein encoded by the gene. Most conventional markers that are used for cancer diagnosis have problems in that the accuracy of diagnosis of liver cancer is relatively low and in that these markers are not clearly distinguished from those of diseases other than liver cancer, and thus have low sensitivity and specificity for liver cancer. Accordingly, the present inventors have investigated a gene whose expression in cancer tissue or cells differs from that in normal tissue or cells, in order to discover a novel cancer diagnostic marker. As a result, the present inventors have found that SIRT7 is more expressed in cancer tissue than in normal tissue. The nucleotide sequence of the SIRT7 gene according to the present invention is set forth in SEQ ID NO: 1.

The present inventors have found that the SIRT7 gene can be used as a cancer diagnostic marker. Specifically, in an example of the present invention, the expression level of the SIRT7 gene in cancer tissue (cells) was significantly higher than that in normal tissue (cells).

This result suggests that, when the expression level of SIRT7 is higher than normal levels, cancer will develop. Therefore, the present invention provides a cancer diagnostic marker composed of the SIRT7 gene or the SIRT7 protein encoded by the gene.

As used herein, the term "diagnosis" means identifying pathological conditions. For the purpose of the present invention, the term "diagnosis" means detecting the development of cancer by determining whether the cancer diagnostic marker was expressed. In addition, the term "diagnosis", as used herein, includes determining whether cancer developed and the progression and alleviation of cancer by determining whether the cancer diagnostic marker was expressed and the expression level of the cancer diagnostic marker.

As used herein, the term "diagnosis marker" or "diagnostic marker" refers to a substance capable of being used to distinguish cancer cells or tissues from normal cells or tissue and includes organic biomolecules whose expression is higher or lower in cancer cells than in normal cells, such as polypeptides or nucleic acids (e.g., mRNA, etc.), lipids, glycolipids, glycoproteins, sugars (monosaccharides, disaccharides, oligosaccharides, etc.) or the like. The cancer diagnostic marker according to the present invention may be the SIRT7 gene or protein whose expression level is higher in cancer cells (or tissue) than in normal cell. Preferably, the SIRT7 gene may have a nucleotide sequence set forth in SEQ ID NO: 1. The SIRT7 protein may have an amino acid sequence set forth in SEQ ID NO: 2.

The present invention may also provide a cancer diagnostic composition comprising a substance for measuring the level of the SIRT7 gene or protein.

As used herein, the term "level of the SIRT7 gene" refers to the expression level of mRNA of the SIRT7 gene, that is, the quantity of mRNA. The substance for measuring the level of the SIRT7 gene may include a primer or probe specific for the SIRT7 gene. In the present invention, the primer or probe specific for the SIRT7 gene may be a primer or probe capable of specifically amplifying all or part of the SIRT7 gene set forth in SEQ ID NO: 1. The primer or probe can be designed by a method known in the art.

As used herein, the term "primer" refers to a single-stranded oligonucleotide capable of acting as a point of initiation of template-directed DNA synthesis under appropriate conditions (i.e., in the presence of four different nucleoside triphosphates and an agent for polymerization) in an appropriate buffer and at a suitable temperature. The appropriate length of the primer may vary according to various factors, for example, temperatures and the intended use of the primer. Further, the primer need not be perfectly complementary to the exact sequence of a template, but should be sufficiently complementary to hybridize with the template. Thus, the primer in the present invention need not be perfectly complementary to the nucleotide sequence of the SIRT7 gene (template) and should be sufficiency complementary to hybridize with the sequence of the gene.

As used herein, the term "amplification reaction" refers to a reaction that amplifies nucleic acid molecules. Such amplification reactions of genes are well known in the art and include, for example, polymerase chain reaction (PCR), reverse-transcription polymerase chain reaction (RT-PCR), ligase chain reaction (LCR), transcription-mediated amplification (TMA), nucleic acid sequence-based amplification (NASBA), etc.

As used herein, the term "probe" refers to a linear oligomer of natural or modified monomers or linkages, including deoxyribonucleotides, ribonucleotides and the like, capable of specifically hybridizing with a target nucleotide sequence, whether occurring naturally or produced synthetically. The probe in the present invention may be single stranded. Preferably, it may be an oligodeoxyribonucleotide. The probe of the present invention may include naturally occurring dNMP (i.e., dAMP, dGMP, dCMP and dTMP), nucleotide analogs, or nucleotide derivatives. The probe in the present invention may also include ribonucleotides. For example, the probe of the present invention may include nucleotides with backbone modifications such as peptide (nucleic acid (PNA) (M. Egholm et al., Nature, 365:566-568 (1993)), phosphorothioate DNA, phosphorodithioate DNA, phosphoramidate DNA, amide-linked DNA, MMI-linked DNA, 2'-O-methyl RNA, alpha-DNA and methylphosphonate DNA, nucleotides with sugar modifications such as 2'-O-methyl RNA, 2'-fluoro RNA, 2'-amino RNA, 2'-O-alkyl DNA, 2'-O-allyl DNA, 2'-O-alkynyl DNA, hexose DNA, pyranosyl RNA, and anhydrohexitol DNA, and nucleotides having base modifications such as C-5 substituted pyrimidines (substituents including fluoro-, bromo-, chloro-, iodo-, methyl-, ethyl-, vinyl-, formyl-, ethynyl-, propynyl-, alkynyl-, thiazolyl-, imidazolyl-, pyridyl-), 7-deazapurines with C-7 substituents (substituents including fluoro-, bromo-, chloro-, iodo-, methyl-, ethyl-, vinyl-, formyl-, alkynyl-, alkenyl-, thiazolyl-, imidazolyl-, pyridyl-), inosine, and diaminopurine.

As used herein, the term "level of the SIRT7 protein" preferably refers to the level of the SIRT7 polypeptide translated from the mRNA of the SIRT7 gene. Substances that may be used to measure the level of the SIRT7 protein include antibodies, such as polyclonal antibodies, monoclonal antibodies and recombinant antibodies, which can bind specifically to the SIRT7 protein.

As described above, in the present invention, it was found that the SIRT7 protein may be used as a marker protein capable of diagnosing cancer. In the present invention, antibody production using the protein may be easily carried out using techniques generally known to those skilled in the art. For example, polyclonal antibodies may be produced using a method widely known in the art, which includes injecting SIRT7 antigen into an animal and collecting blood from the animal to obtain sera containing antibodies. Such polyclonal antibodies may be produced from any animal host, such as goats, rabbits, sheep, monkeys, horses, pigs, cows and dogs. Monoclonal antibodies may be produced by a method widely known in the art, such as a hybridoma method (Kohler et al., European Journal of Immunology, 6, 511-519, 1976) or a phage antibody library technique (Clackson et al, Nature, 352, 624-628, 1991, Marks et al, J. Mol. Biol., 222:58, 1-597, 1991).

The antibodies according to the present invention include complete forms having two full-length light chains and two full-length heavy chains, as well a functional fragments of antibody molecules. The term "functional fragments of antibody molecules" refers to fragments retaining at least an antigen-binding function, which are exemplified by Fab, F(ab'), F(ab')2 and Fv.

The present invention may also provide as cancer diagnostic kit comprising a cancer diagnostic composition capable of measuring the expression level of the SIRT7 protein or a gene encoding the same.

The cancer diagnostic composition that is included in the cancer diagnostic kit of the present invention may comprise a primer, probe or antibody capable of measuring the expression level of the SIRT7 protein or a gene encoding the same. The definitions of the primer, the probe and the antibody are as described above.

If the cancer diagnostic kit of the present invention is used in PCR amplification procedure, the kit of the present invention may optionally include reagents required for PCR amplification, for example, buffer, DNA polymerase (e.g., thermostable DNA polymerase obtained from *Thermus aquaticus* (Taq), *Thermus thermophilus* (Tth), *Thermus filiformis, Thermis flavus, Thermococcus literalis* or *Pyrococcus furiosus* (Pfu)), DNA co-polymerase and dNTPs. If the cancer diagnostic kit of the present invention is applied to immunoassay, the kit of the present invention may optionally comprise a secondary antibody and a labeled substrate. Further, the kit of the present invention may be made of a plurality of packagings or compartments including the above-described reagent components.

The present invention also provides a cancer diagnostic microarray comprising a cancer diagnostic composition capable of measuring the expression level of the SIRT7 protein or a gene encoding the same.

In the microarray of the present invention, the primer, probe or antibody capable of measuring the expression level of the SIRT7 protein or a gene encoding the same serves as a hybridizable array element and is immobilized on a substrate. A preferable substrate includes suitable solid or semi-solid supports, such as membrane, filter, chip, slide, wafer, fiber, magnetic or nonmagnetic bead, gel, tubing, plate, polymer, microparticle and capillary tube. The hybridizable array elements are arranged and immobilized on the substrate. Such immobilization occurs through chemical binding or covalent binding such as UV. For example, the hybridizable array elements can be bound to a glass surface modified to contain epoxy compound or aldehyde group or to a polylysine-coated surface by UV irradiation. Further, the hybridizable array elements can be bound to a substrate through linkers (e.g. ethylene glycol oligomer and diamine). Meanwhile, if a sample to be applied to the microarray of the present invention is a nucleic acid sample, it may be labeled and hybridize with array elements on the microarray. Various hybridization conditions are applicable, and for the detection and analysis of the extent of hybridization, various methods are available depending on labels used.

The present invention also provides a method of diagnosing cancer by measuring the expression level of the SIRT7 gene or the level of the SIRT7 protein, the method comprising the steps of: (a) measuring the expression level of the SIRT7 gene or the level of the SIRT7 protein in a biological sample; and (b) comparing the results measured in step (a) with the expression level of the SIRT7 gene or the level of the SIRT7 protein in a normal control sample. Herein, the process of measuring the expression level of the SIRT7 gene or the level of the SIRT7 protein can be performed by detecting or isolating mRNA or protein from the biological sample using a known technique.

As used herein, the term "biological sample" refers to a sample derived from a living organism, in which the expression level of SIRT7 gene or the level of the SIRT7 protein according to the development or progression of cancer differs from that in a normal control group. Examples of the sample include, but are not limited to, tissues, cells, whole blood, serum, plasma, saliva, and urine.

The measurement of the expression level of the SIRT7 gene is preferably the measurement of the level of mRNA. Methods for measuring the mRNA level include, but are not limited to, reverse transcriptase-polymerase chain reaction (RT-PCR), real-time reverse transcriptase-polymerase chain reaction, RNase protection analysis, Northern blotting, DNA chip assay, etc. The measurement of the level of the SIRT7 protein can be carried out using an antibody. In this case, the SIRT7 marker protein in the biological sample and an antibody specific thereto form a complex, i.e., an antigen-antibody complex. The amount of antigen-antibody complex formed may be quantitatively determined by measuring the signal intensity of a detection label. This detection label may be selected from the group consisting of enzymes, fluorescent substances, ligands, luminescent substances, microparticles, redox molecules and radioisotopes, but is not limited thereto.

Analysis methods for measuring the protein levels include, but are not limited to, Western blotting, ELISA, radioimmunoassay, radioimmunodiffusion, ouchterlony immunodiffusion, rocket immunoelectrophoresis, immunohistochemistry, immunoprecipitation assay, complement fixation assay, FACS, and protein chip assay.

In the present invention, using the detection methods as described above, the expression level of SIRT7 mRNA or the level of SIRT7 protein in a control group and the expression level of SIRT7 mRNA or the level of SIRT7 protein in a cancer patient or a patient suspected of having cancer can be measured. Further, the onset, progression or prognosis of cancer can be predicted and diagnosed by comparing the measured expression level with that in a control group (i.e., normal people).

In an example of the present invention, the tissues and cancer cells obtained from cancer patients were lysed to obtain a lysate containing intracellular proteins, and then the level of the SIRT7 protein in each of the cancer samples was measured by Western blot analysis using an antibody against SIRT7, after which the measured values were compared with those obtained for a control group.

From the above-described results, the present inventors expected that, when cancer develops, the expression of SIRT7 in cells or tissue increases, and thus when the expression of SIRT7 in cancer cells is inhibited, cancer can be prevented or treated. Also, the present inventors could see that a substance capable of inhibiting the expression of SIRT7 can be used as a cancer therapeutic agent.

Therefore, the present invention provides a method for screening a substance for preventing or treating cancer, the method comprising the steps of: (a) bringing a sample to be analyzed into contact with cells containing SIRT7 gene or SIRT7 protein; (b) measuring the expression level of the SIRT7 gene, the level of the SIRT7 protein or the activity of the SIRT7 protein; and (c) selecting the sample as the substance for preventing or treating cancer when the results measured in step (b) indicate that the expression level of the SIRT7 gene, the level of the SIRT7 protein or the activity of the SIRT7 protein decreased.

According to the method of the present invention, a sample to be analyzed can be brought into contact with cells that contain or express the SIRT7 gene or the SIRT7 protein. As used herein, the term "sample" refers to a unknown substance that is used in screening to examine whether it influences the expression level of the SIRT7 gene, the level of the SIRT7 protein or the activity of the SIRT7 protein. Examples of the sample include, but are not limited to, chemical substances, nucleotides, antisense-RNA, siRNA (small interference RNA), and natural extracts. Then, the expression level of the SIRT7 gene, the level of the SIRT7 protein or the activity of the SIRT7 protein in the cells treated with the sample can be measured, and when the results of the measurement indicate that the expression level of the SIRT7 gene, the level of the SIRT7 protein or the activity of the SIRT7 protein decreased, the sample can be determined to be a substance capable of treating or preventing cancer.

Herein, methods for measuring the expression level of the SIRT7 gene, the level of the SIRT7 protein or the activity of the SIRT7 protein include various methods known in the art, for example, reverse transcriptase-polymerase chain reaction, real-time polymerase chain reaction, Western blotting, Northern blotting, ELISA (enzyme linked immunosorbent assay), RIA (radioimmunoassay), radioimmunodiffusion, and immunoprecipitation assay, but are not limited thereto. The present invention also provides a pharmaceutical composition for preventing or treating cancer, the composition comprising, as an active ingredient, a substance that inhibits the expression of the SIRT7 gene or reduces the expression and activity of the SIRT7 protein.

In an example of the present invention, an experiment was performed to whether cancer can be prevented or treated when the expression of the SIRT7 gene or the SIRT7 protein is inhibited. Specifically, it could be seen that, when the expression of SIRT7 in cancer cells was inhibited using siRNA against the SIRT7 gene, the growth of the cancer cells was inhibited, the death of the cancer cells was promoted and the tumor volume decreased. Meanwhile, normal cells maintain a balance between the ability to self-grow and self-regulate differentiation and the apoptotic ability, but in the case of cancer cells, this balance is broken, and thus the cells rapidly grow in a geometrical progression. The cell cycle for cell growth and differentiation is largely divided into interphase and mitotic phase, and the interphase consists of G(1)-phase in which synthesis of various proteins required for cell division occurs, S-phase in which DNA synthesis occurs, and mitosis-phase in which cell differentiation occurs. In addition, cell division requires regulatory factors capable of regulating it, and particularly, various cyclin proteins function to regulate the phases of the cell cycle by forming cyclin/CDK complexes with cyclin-dependent kinase (CDK). Particularly, p21 that is a cyclin kinase inhibitor (CKI) function to bind to the cyclin/CDK complex in the G1-phase to prevent the complex from being activated and inhibit the progression of the cell cycle, thereby inhibiting the growth of cells.

In addition, the cyclin proteins play a central role in the cell cycle. The synthesis and degradation of cyclins is tightly controlled such that their level of expression fluctuates during the cell cycle. Cyclins bind to cyclin-dependent serine/threonine kinases (CDKs) and this association is essential for CDK (such as CDK1, CDK2, CDK4 and/or CDK6) activity within the cell. Moreover, it was reported that CDKs are present downstream of a number of oncogene signalling pathways. It is known that deregulation of CDK activity by upregulation of cyclins or deletion of endogenous inhibitors appears is an important axis between mitogenic signaling pathways and proliferation of tumor cells. In addition, it has been recognized that an inhibitor of cell cycle kinases is useful as a selective inhibitor of cell proliferation, such as growth of mammalian cancer cells.

Accordingly, the present inventors have expected that, based on the fact that SIRT7 is overexpressed in cancer cells, SIRT7 will also be involved in the cell cycle of cancer cells. Also, the present inventors investigated cell cycle regulatory factors that are influenced by SIRT7. Specifically, the results obtained in an example of the present invention indicated that, when the expression of the SIRT7 gene in cancer cells was inhibited by treating the cancer cells with SIRT7 siRNA, the expressions of cyclin D1 and CDK2 were also inhibited. Accordingly, the present inventors could confirm that SIRT7 causes cancer by causing abnormalities in the cell cycle and growth of cells through the regulation of cyclin D1 and CDK2. Further, the present inventors could confirm that when the expression of SIRT7 in cells is inhibited, the onset of cancer can be prevented or cancer can be treated.

In addition, as described in examples of the present invention, inhibition of the expression of SIRT7 can inhibit tumor growth by influencing the cell cycle to arrest the cells at G1/S phase, and can deregulate cell cycle regulatory proteins by induction of p21$^{WAF1/Cip1}$ and inhibition of cyclin D1. Further, it could be seen that inhibition of the expression of SIRT7 functions to significantly up-regulate the expression of LC3B-II and pro-autophagic Beclin-1. Therefore, the inventive pharmaceutical composition for preventing or treating cancer may comprise any substance capable of inhibiting the expression of SIRT7. Preferably, the composition of the present invention may comprise, as an active ingredient, one or more selected from among chemical substances, nucleotides, antisense RNA, siRNA oligonucleotides, and natural extracts. More preferably, the composition for preventing or treating cancer of the present invention may comprise, as an active ingredient, an antisense or siRNA (small interference RNA) oligonucleotide having a sequence complementary to the nucleotide sequence of the SIRT7 gene of the present invention. Even more preferably, the composition of the present invention may comprise, as an active ingredient, an oligonucleotide having a nucleotide sequence of ACGG-GAACAUGUACAUUGATT (SEQ ID NO: 3) or UCAAU-GUACAUGUUCCCGUGG (SEQ ID NO: 4), which is an siRNA against SIRT7. As used herein, the term "antisense oligonucleotide" refers to a DNA, an RNA, or a derivative thereof, which contains a nucleotide sequence complementary to the sequence of a specific mRNA and functions to bind to a complementary sequence in the mRNA to inhibit the translation of SIRT7 to protein. As used herein, the term "antisense sequence" refers to a DNA or RNA sequence that is complementary to SIRT7 mRNA and can bind to SIRT7 mRNA and can also inhibit the function of SIRT7 mRNA; either its translation into protein, its translocation into the cytoplasm, maturation, or any other activity necessary to its overall biological function. Further, the antisense nucleotide may be modified at one or more base, sugar or backbone positions to improve the desired effect (De Mesmaeker et al., Curr. Opin Struct Biol., 5, 3, 343-55, 1995). The nucleotide backbone may be modified with phosphorothioate, phosphotriester, methylphosphonate, single-chain alkyl, cycloalkyl, single-chain heteroatomic, or heterocyclic sugar-sugar bonding. Also, the antisense nucleotide may include one or more substituted sugar moieties. The antisense nucleotide may include a modified base. Examples of the modified base include hypoxanthine, 6-methyladenine, 5-methylpyrimidine (especially, 5-methylcytosine), 5-hydroxymethylcytosine (HIMC), glycosyl HMC, gentiobiosyl HMC, 2-aminoadenine, 2-thiouracil, 2-thiothymine, 5-bromouracil, 5-hydroxymethyluracil, 8-azaguanine, 7-deazaguanine, N6-(6-aminohexyl)adenine, 2,6-diaminopurine, etc. Also, the antisense nucleotide of the present invention may be chemically linked to one or more moieties or conjugates that improve the activity and cell adhesion of the antisense nucleotide. The moiety may be a lipid-soluble moiety, such as cholesterol moiety, cholesteryl moiety, cholic acid, thioether, thiocholesterol, aliphatic chain, phospholipid, polyamine, polyethylene glycol chain, adamantane acetic acid, palmityl moiety, octadecylamine, and hexylamino-carbonyl-oxycholesterol moiety, but is not limited thereto. Methods for preparing oligonucleotides having lipid-soluble moieties are well known in the art (U.S. Pat. Nos. 5,138,045, 5,218,105 and 5,459,255). The modified nucleotide may have increased stability against nucleases and can increase the binding ability of the antisense nucleotide to bind to its target mRNA.

The antisense oligonucleotide may be synthesized in vitro according to a conventional method and administered in vivo or it may be synthesized in vivo. An example of synthesizing the antisense oligonucleotide in vitro is performed using RNA polymerase I. An example of synthesizing the antisense oligonucleotide in vivo is performed using a vector having the origin of the multiple cloning site (MCS) in an opposite direction so that the antisense RNA is transcribed. Preferably, the antisense RNA may have a translation stop codon within its sequence in order to prevent its translation into a peptide sequence.

As used herein, the term "siRNA" refers to a nucleotide molecule capable of mediating RNA interference or gene silencing (see WO 00/44895, WO 01/36646, WO 99/32619, WO 01/29058, WO 99/07409 and WO 00/44914). Since siRNA can suppress the expression of the target gene, it provides an effective way of gene knockdown or genetic therapy.

The siRNA molecule that is used in the present disclosure may have a structure in which its sense strand (a sequence corresponding to the SIRT7 mRNiA sequence) and its antisense strand (a sequence complementary to the SIRT7 mRNA sequence) form a double strand. Alternatively, it may have a single-stranded structure having self-complementary sense and antisense strands. Further, the siRNA is not limited to those in which double-stranded RNA moieties constitute complete pairs, but includes unpaired moieties such as mismatch (corresponding bases are not complementary), bulge (having no base in one chain), etc. The terminal end of the siRNA may be either blunt or cohesive as long as it is capable of suppressing the expression of the SIRT7 gene via RNAi. The cohesive end may be either 3'-overhang or 5'-overhang.

In the present invention, the siRNA molecule may have a short nucleotide sequence inserted between the self-complementary sense and antisense strands. In this case, the siRNA molecule formed by the expression of the nucleotide sequence forms a hairpin structure via intramolecular hybridization, resulting in a stem-and-loop structure. The stem-and-loop structure is processed in vitro or in vivo to give an activated siRNA molecule capable of mediating RNAi.

Methods for preparing siRNA include a method in which siRNA is synthesized in vitro, and then transformed into cells, and a method in which an siRNA expression vector or PCR-derived siRNA expression cassette designed to express siRNA in cells is transformed or transfected into cells.

The inventive composition comprising a gene-specific siRNA may comprise an agent for promoting the intracellular introduction of siRNA. The agent for promoting the intracellular introduction of siRNA may generally be an agent for promoting the introduction of nucleic acids. For example, liposomes may be used alone or in combination with a lipophilic carrier selected from among sterols including cholesterol, cholate and deoxycholic acid. For the intracellular introduction of siRNA, other agents may also be used, including cationic polymers, such as poly-L-lysine, spermine, polysilazane, PEI (polyethylenimine), polydihydroimidazolenium, polyallylamine, chitosan, etc., or anionic polymers, such as succinylated PLL, succinylated PEI, polyglutamic acid, polyaspartic acid, polyacrylic acid, polymethacrylic acid, dextran sulfate, heparin, hyaluronic acid, etc.

Further, when an antibody specific to the SIRT7 protein is used as a substance for reducing the expression and activity of the SIRT7 protein, the antibody can be coupled (e.g., covalently bonded) directly to existing therapeutic agents or can be coupled indirectly via a linker. Examples of therapeutic agents that may be coupled with the antibodies include, but are not limited to, radionucleotides, such as 131I, 90Y, 105Rh, 47Sc, 67Cu, 212Bi, 211At, 67Ga, 125I, 186Re, 188Re, 177Lu, 153Sm, 123I, and 111In; biological response modifiers or biological response modifying drugs, such as methotrexate, adriamycin, and lymphokines including interferons; toxins, such as ricin, abrin, and diphtheria; heterofunctional antibodies, that is, complexes formed by conjugating heterotype antibodies with each other, which are able to bind both to cancer cells and to effector cells (e.g., killer cells such as T cells); and natural, that is, non-related or non-complexed antibodies.

The pharmaceutical composition according to the present invention may further comprise a pharmaceutically acceptable carrier. As used herein, the term "pharmaceutically acceptable" refers to a physiologically acceptable composition which, when administered to human, will generally not cause allergic reactions, such as gastrointestinal disturbance, dizziness, and similar reactions. Examples of the pharmaceutically acceptable carrier include carriers for oral administration, such as lactose, starch, cellulose derivatives, magnesium stearate, and stearic acid, and carriers for parenteral administration, such as water, suitable oil, saline solution, aqueous glucose, and glycol. The composition of the present invention may further comprise a stabilizer and a preservative. Suitable stabilizers include antioxidants, such as sodium bisulphite, sodium sulphite and ascorbic acid. Suitable preservatives include benzalkonium chloride, methyl- or propyl-paraben, and chlorobutanol. Other pharmaceutically acceptable carriers can be found in Remington's Pharmaceutical Sciences, 19th ed., Mack Publishing Company, Easton, Pa., 1995.

The pharmaceutical composition according to the present invention can be formulated into a suitable form together with the above pharmaceutically acceptable carrier according to any method known in the art. Specifically, the inventive pharmaceutical composition can be formulated into various parenteral or oral dosage forms according to a conventional method. The parenteral dosage formulations typically include an injectable formulation, preferably, an isotonic solution or a suspension. The injectable formulation may be prepared using a suitable dispersing agent, wetting agent or suspending agent according to any method known in the art. For example, the injectable formulation can be prepared by dissolving necessary components in saline or buffer. Also, the oral dosage formulations include, but are not limited to, powders, granules, tablets, pills and capsules.

The pharmaceutical composition formulated as described above may be administered in an effective amount by various routes, including oral, transdermal, subcutaneous, intravenous and intramuscular routes. The term "administration", as used herein, refers to the introduction of a predetermined substance into a patient using any suitable method. The substance may be administered via any general route, as long as it can reach target tissue.

As used herein, the term "effective amount" refers to an amount sufficient to achieve prevention or treatment when administered to a patient. The dose of the pharmaceutical composition of the present invention may vary depending on various factors, such as disease type and severity, age, body weight, sensitivity to drugs, type of current therapy, mode of administration, target cell, etc., and may be easily determined by those of ordinary skill in the art. The pharmaceutical composition of the present invention may also be administered in combination with conventional pharmaceutical agents, sequentially or simultaneously with the conventional pharmaceutical agents, and in single dose or multiple doses. Preferably, with all of the factors taken into account, the minimum dose required to achieve the maximum effect without side effects can be administered. Preferably, the composition may be administered several times a day at a dose of 1-10000 μg/kg weight/day, and more preferably 10-1000 mg/kg weight/day.

EXAMPLES

Hereinafter, the present invention will be described in further detail with reference to examples. It will be obvious to a person having ordinary skill in the art that these examples are illustrative purposes only and are not to be construed to limit the scope of the present invention.

In the present invention, it was found that the SIRT7 gene can be used as a cancer diagnostic marker. Specifically, in an example of the present invention, it was shown that the expression level of the SIRT7 gene was significantly higher in liver cancer tissue (cells) than in normal tissue (cells).

This result suggests that, when the expression level of the SIRT7 gene is higher than normal levels, liver cancer will develop. Therefore, the present invention may provide a liver cancer diagnostic marker composed of the SIRT7 gene or the SIRT7 protein encoded by the gene.

The present invention is based on the use of the SIRT7 gene as a cancer marker. Specifically, the expression of the SIRT7 expression may be indicative of the development proliferative activity of cancer cells, the metastatic activity of cancer, or the metastatic activity of the cell cycle.

Therefore, the present invention includes the use of SIRT7 as a cancer diagnostic marker, and a cancer (cell cancer) diagnostic method comprising measuring the expression level of SIRT7.

In addition, based on the function of SIRT7 as a marker of cancer-related diseases, the function of an inhibitor of the expression or activity of SIRT7, for example, SIRT7 RNAi or SIRT7 antibody, can be predicted. Thus, the present invention includes the anticancer use of an inhibitor of the expression or activity of SIRT7.

Molecular Mechanisms of SIRT7-miRNA

Meanwhile, the present inventors first elucidated SIRT7 expression-related mechanisms occurring in hepatocellular carcinomas (HCC), in addition to the novel use of SIRT7 as a cancer marker whose expression is up-regulated in hepatocellular carcinomas.

The present invention includes these SIRT7 expression-related molecular mechanisms as follows.

Inhibition of SIRT7 expression influences the cell cycle to arrest cells in the G1/S phase, thereby inhibiting tumor growth.

Inhibition of SIRT7 expression deregulates cell cycle regulatory proteins by induction of p21$^{WAF1/Cip1}$ and inhibition of cyclin D1.

Inhibition of SIRT7 expression significantly up-regulates the expression of LC3BII and pro-autophagic Beclin-1.

The expression of SIRT7 in cancer tissue is regulated by a specific miRNA, and particularly, the present invention is directed to particular miRNAs capable of regulating the expression of the SIRT7 gene and to the use thereof.

miRNA (microRNA) is a 21-25 nt single-stranded RNA molecule that regulates the gene expression of eukatyotes and is made by two-step processing. Primary miRNA is processed into an about 70-90 nt stem-loop structure (i.e., pre-miRNA) by RNaseIII type enzyme (Drosha) in the nucleus, and then cleaved by the enzyme Dicer in the cytoplasm into a 21-25 nt mature miRNA. The mature miRNA is processed into a longer transcript having a length of ~22 nts. Pri-miRNA can be transcribed by RNA Pol II as independent transcriptional units or can originate from spliced-out introns of host genes. Currently, more than 300 human miRNAs are known, but only several miRNAs have any allotted biological function. Studies on specific miRNAs are required to understand the pervasiveness and importance of miRNA-mediated gene regulation. The present invention first suggests the function of a particular miRNA that regulates the expression of the SIRT7 gene that is associated with cancer formation and development. In one example of the present invention, miRNA expression profiling analysis was performed to identify miR-NAs that are abnormally regulated in human HCC.

miR-125a-5p and miR-125b

The present invention is directed to specific miRNAs that regulate the expression of the oncogene SIRT7. The specific miRNAs may preferably be miR-125a-5p, miR-125b, miR-148a and miR-152. Most preferably, the miRNAs are miR-125a-5p and miR-125b. miR-125a-5p may have a nucleotide sequence of 5'-ucccugagacccuuuaaccuguga-3' (SEQ ID NO: 7), and miR-125b may have a nucleotide sequence of 5'-ucccuggacccuaacuuguga-3' (SEQ ID NO: 8). miR-125a-5p and miR-125b in the present invention include an about 17-24 nt nucleic acid molecule produced from Pri-miRNA, pre-miRNA, mature-miRNA or functional equivalents thereof.

The miRNA binds complementarily to its target mRNA and acts as a post-transcriptional gene suppressor. The miRNA, miR-125a-5p and miR-125b of the present invention are comparable with short-interference RNA (siRNA). Like SIRT7 siRNA, miR-125a-5p, miR-125b, miR-148a and miR-152 can inhibit the expression of endogenous SIRT7.

microRNA miR-125a-5p and miR-125b of the present invention bind to the 3' untranslated region (3'UTR) of SIRT7 to lower the stability or translation efficiency of mRNA to thereby inhibit the expression of the target gene SIRT7.

Specifically, microRNA miR-125a-5p and miR-125b of the present invention have the following functions.

(1) miR-125a-5p and miR-125b induce the G1 arrest of the cell cycle.

Particularly, the miRNAs of the present invention influence the cell cycle to regulate the expression of the SIRT7 gene and control the growth of liver cancer cells.

The cell cycle occurs in a specific order, and if this order is reversed, the cell cycle will be difficult to maintain. This order is correctly maintained by Cyclin and Cdk. In the initial stage of the G1 phase of the cell cycle, Cdk4, 6, 8 or the like is activated depending on the type of cell, and in the late stage of the G1 phase and the initial stage of the S stage, Cdk2 acts. G2-to-M progression requires the action of Cdk1 (Cdc2). The activation of Cdk necessarily requires binding to cyclin. Specifically, Cdk4, 6 and 8 are activated by binding to cyclin D, and Cdk2 binds to cyclin A and E. In addition, Cyclin G, F and the like are known, but the function thereof in the progression of the cell cycle is still unclear. Because a cyclin-Cdk complex specific for each phase of the cell cycle is activated and proteins that are phosphorylated specifically by the respective Cdks are involved in the progression of the cell cycle, the cell cycle may also be named "Cdk cycle". Cdk is necessary for cyclin activation. Activated Cdk-cyclin consists of a regulation unit of cyclin and an activation unit of Cdk.

Methods for regulating Cdk by cyclin can be classified into two methods. In the first method, cyclin binds to Cdk to induce the structural change of the protein so that the arrangement of ATP phosphate groups changes such that they are easily delivered to the substrate protein. In addition, the position of T loops that prevent the protein substrate from access to Cdk changes to facilitate access of the substrate. The reason why Cdk is activated only in a specific phase of the cell cycle is because of cyclin synthesis that occurs specifically in the cell cycle.

The synthesis of cyclin D reaches a peak in the G1 metaphase and is induced mainly by mitogens of cell growth factors. Cyclin D is divided into three subtypes (D1, 2 and 3), and the expression level thereof varies depending on the type of cell. When the synthesis of cyclin D is inhibited, the G1 arrest of the cell cycle occurs, and when cyclin D is overexpressed, the G1 phase becomes shorter and the cell cycle is initiated even in the absence of mitogens.

Particularly, the present invention is related to the induction of p21$^{WAF1/Cip1}$ and the inhibition of cyclin D1 protein, which are involved in G1 arrest. Related specific mechanisms are as follows.

(2) Expression of miR-125a-5p and miR-125b is increased by p53 activity to inhibit tumor growth.

p53 is an about 53-KDa phosphorylated protein that is encoded by 11 exons located on chromosome 17q13 and belongs to a highly conserved gene family together with p63 and p73. p53 responds to signals that damage intracellular DNA, whereby it regulates the expression of various downstream genes to regulate. Also, it induces cell death to protect cells from malignant transformation.

The p53 protein is present in normal cells at very low levels, because it binds to HDM2 (human double minute 2) immediately after synthesis so that it is degraded rapidly. However, when DNA damage is applied to cells, p53 is stabilized and accumulated in the nucleus to form a tetramer that binds to a p53-binding site having a highly conversed nucleotide sequence of 5-PuPuPuC(A/T)(T/A)GPyPyPy-3', which is present on the promoters of several genes. p53 that did bind to DNA activates the transcription of several genes which are involved mainly in regulation of the cell cycle, recovery from DNA damage, and control of cell death, and it also inhibits the expression of the target gene.

G1/S transition in the cell cycle of normal cells is controlled by the pRb-E2F system. During the initial stage of G1, pRb binds to E2F protein together with p130 and p107 to thereby inhibit the transcription activity of E2F. However, in the late stage of G1, pRb is phosphorylated by a cyclin-CDK (cyclindependent kinase) complex so that E2F is released from pRb, and the activated E2F activates the expression of several genes that are involved in DNA synthesis, thereby inducing the progression of the cell cycle from G1 to S phase.

When DNA damage is applied to cells, the expression of p53 increases rapidly, and as a result, the expression of p21$^{WAF1/CIP1}$ that is a target gene downstream of p53 is induced. p21 inhibits the activity of the cyclin-CDK complex to inhibit the phosphorylation of pRb, and for this reason, E2F remains bound to pRb in an inactivated state. Thus, the cell cycle is arrested in G1 phase. p21 also interferes with DNA replication by inhibiting the activity of PCNA (proliferating cell nuclear antigen) acting as a co-factor of DNA polymerase δ and ε.

The expression of miR-125a-5p and miR-125b of the present invention is increased by the activity of p53, and miR-125a-5p and miR-125b induce the expression of p21$^{WAF1/CIP1}$ to arrest the cell cycle in G1 and interfere with DNA replication to thereby inhibit the growth of liver cancer cells.

(3) Expression of miR-125a-5p and miR-125b is reduced by promoter methylation of promoter.

The expression of microRNA of the present invention is also regulated by epigenetic factors. Specifically, it is regulated by DNA methylation rather than by historic modification.

DNA methylation is one of the most frequent genetic alterations found in tumors and frequently occurs in CpG islands whose nucleotide sequence consists mainly of cytosine and guanine. It occurs when a methyl group is attached to 5-cytosine by methyl transferase.

This DNA methylation functions to inhibit the transcription of a gene in the promoter region. The transcribed gene undergoes post-translational regulation by the stability and translation of the mRNA.

In other words, the expression of miR-125a-5p and miR-125b of the present invention is reduced by promoter methylation, and thus the expression of miR-125a-5p and miR-125b can be stimulated by inhibiting the promoter methyation.

Meanwhile, the present invention is also directed to the above-described molecular mechanism in which miRNA miR-125a-5p and miR-125b participate in transcriptional circuits that control the expression of the SIRT7 gene and the growth of liver cancer cells.

Moreover, through this molecular mechanism, it can be seen that miR-125a-5p and miR-125b of the present invention are regulators of SIRT7 in hepatocarcinogenesis, and thus miR-125a-5p and miR-125b are direct suppressors of endogenous SIRT7 and can function as tumor suppressors in hepatocarcinogenesis.

The function of microRNA in the development of cancer is determined according to a gene targeted by the microRNA. The present invention is directed to a tumor-suppressing microRNA that targets the oncogene SIRT7.

Diagnostic Use

Thus, in one aspect, the present invention is directed to a method of examining the expression profiling of miR-125a-5p or miR-125b to provide information needed to diagnose or prognose SIRT7-expressing cancer.

In other words, based on the first finding that miR-125a-5p or miR-125b is associated with the expression of SIRT7, the development or prognosis of SIRT7-expressing cancer, for example, liver cancer, can be predicted by examining the expression profiling of miR-125a-5p or miR-125b.

"SIRT7-expressing cancer" is not limited to a particular kind, as long as it is cancer in which the SIRT7 gene, but it is most preferably liver cancer. The liver cancer includes primary liver cancers or metastatic liver cancers. The primary liver cancers include hepatocellular carcinoma and biliary tract cancer. The biliary tract cancer is cancer occurring in the biliary tract through which bile is transported, and hepatocellular carcinoma is liver cancer occurring in patients with chronic liver diseases such as cirrhosis. Hepatocellular carcinoma is the most frequent liver cancer in people. In addition, cancers may be malignant tumors or primary tumors thereof.

The development or progression of liver cancer can be monitored by the expression profiling of miR-125a-5p or miR-125b. Comparison can be performed based on the number or amount of miRNAs in a sample, or any combination thereof. The degree of overexpression of SIRT7 can be determined by measuring the amount of down-regulated miRNAs, and based on the results of the measurement, the development or prognosis of liver cancer can be predicted.

In addition, the present invention includes any analysis methods and systems such as kits, which can be used for diagnosis of liver cancer.

Anticancer Use

Moreover, in another aspect, the present invention is directed to the anticancer use of miR-125a-5p and miR-125b against SIRT7-expressing cancer by stimulating the expression or activity of miR-125a-5p and miR-125b to inhibit the expression of SIRT7.

In one embodiment, the present invention provides a method of treating liver cancer or the like by transfecting SIRT7-expressing cancer cells with miR-125a-5p and/or miR-125b, or mimics thereof, to allow them to bind to the 3'-UTR of SIRT7 mRNA.

As used herein, the "transfection" means introducing an foreign substance into eukaryotic cells by a viral vector or other delivery means. Transfection of animal cells typically involves opening transient pores or "holes" in the cell plasma membrane, to allow the uptake of material. Genetic material, or even proteins such as antibodies, may be transfected into cells. In addition to electroporation, transfection can be carried out by mixing a cationic lipid with the material to produce liposomes, which fuse with the cell plasma membrane and deposit their cargo inside.

One method is transfection by calcium phosphate. HEPES-buffered saline solution (HeBS) containing phosphate ions is combined with a calcium chloride solution containing the material to be transfected. When both solutions are combined, a fine precipitate of the positively charged calcium and the negatively charged phosphate will form, binding the material to be transfected on its surface. The suspension of the precipitate is then added to the cells to be transfected. The cells absorb the material to be transfected, together with a portion of the precipitate. Other methods use highly branched compounds (e.g. dendrimers) to bind the genetic material (miRNA) of the present invention and get it into the cell. Another method is the inclusion of the genetic material to be transfected in liposomes, i.e. small, membrane-bounded bodies that are in some ways similar to the structure of a cell and can actually fuse with the cell membrane, releasing the genetic material into the cell. For eukaryotic cells, lipid-cation based transfection is more typically used, because the cells are more sensitive. Another method is the use of cationic polymers such as DEAE-dextran or polyethylenimine. The negatively charged genetic material binds to the polycation and the complex is taken up by the cell via endocytosis.

A direct approach to transfection is the gene gun, where the genetic material is coupled to a nanoparticle of an inert solid (commonly gold) which is then "shot" directly into the target cell. The genetic material can also be introduced into cells using viruses as a carrier. In such cases, the technique is called viral transduction, and the cells are said to be transduced. Other methods of transfection include nucleofection, electroporation, heat shock, magnetofection and proprietary transfection reagents such as Lipofectamine, Dojindo Hilymax, Fugene, jetPEI, Effectene or DreamFect.

Formation of double-stranded RNA by binding of miRNA in transfected cells is performed either by blocking the protein translation system through a process similar to RNA interference (RNAi) while causing the degradation of mRNA transcripts, or by inhibiting protein translation without causing the degradation of mRNA, thereby inhibiting the expression of the target gene SIRT7.

In another embodiment of anticancer use, the present invention provides an anticancer composition against SIRT7-expressing cancer, which comprises, as an active ingredient, an agent for promoting the expression or activity of miR-125a-5p or miR-125b.

As used herein, the term "agent for promoting" refers to a substance that promotes, enhances or increases the expression or activity of the target gene. The mechanism of action of the agent for promoting is not specifically limited. Examples thereof include organic or inorganic compounds, proteins, carbohydrates, polymer compounds such as lipids, and a composite of various compounds. For example, the agent for promoting miR-125a-5p or miR-125b may include a substance that promotes, enhances or increases the expression or activity of these miRNAs. As evident to those skilled in the art, it can be chemically or biochemically modified, or can be formulated into compositions that may be administered to target cells by any means or an expression structure.

In some embodiments, a miRNA molecule or a miRNA precursor molecule is expressed from transcriptional units inserted into RNA vectors (generally also referred to as recombinant vectors or expression vectors). The nucleic acid molecule encoding the miRNA can be delivered into cells by a vector so as to target a specific gene. Examples of recombinant vectors include DNA plasmids or viral vectors. Various expression vectors are known in the art. Selection of suitable expression vectors may be based on various factors, including, but not limited, the cell type in which they are to be expressed.

In addition, a number of suitable methods are known in the art. Generally, cells that express the target gene are transfected. For transfection, various methods may be used, such as electroporation, or the use of cationic lipids or cationic polymers as helpers for transfection. Then, the cells are cultured under suitable conditions that allow the expression of the target gene. Then, the expression of the target gene is measured using a suitable technique, for example, RT-PCR or measurement of the amount of a reporter gene. Generally, any kind of cells may be used for transfection, but in a preferred embodiment, the cells may be eukaryolic cells, preferably animal cells, more preferably mammalian cells, and most preferably human cells.

The composition according to the present invention should comprise a therapeutically effective amount of miR-125a-5p and/or miR-125b, or mimics thereof, so as to down-regulate the expression of SIRT7. The therapeutically effective amount can be given by a known administration route. The composition according to the present invention is applied such that miR-125a-5p and/or miR-125b, or mimics thereof can be transfected into liver cells expressing SIR17. The composition of the present invention may contain or use any means for transfecting a genetic substance into target cells. Preferably, the composition may comprise a cationic lipid and may further comprise a cationic amphipathic substance such that the miRNAs and mimics thereof can be released into SIRT7-expressing cells.

In addition, the nucleic acid molecule and promoting agent of the present invention may be formulated into an anticancer pharmaceutical composition according to a conventional pharmaceutical technique.

The composition may comprise an active agent or a pharmaceutically acceptable salt of the active agent. The composition may be administered simultaneously or continuously. The composition may comprise, in addition to an active substance, a pharmaceutically acceptable excipient, carrier, buffer, stabilizer or other substances well known in the art. Such materials should be non-toxic and should not interfere with the efficacy of the active ingredient. The carrier may take a wide variety of forms depending on the form of preparation desired for administration, e.g. topical, intravenous, oral, intrathecal, epineural or parenteral. Generally, formulations for oral or parenteral administration can be prepared by mixing the active ingredient with diluents or excipients such as fillers, extenders, binders, wetting agents, disintegrating agent or surfactants. The dose and scheme effective for administration can be empirically determined and can be easily determined by those skilled in the art. A single or multiple dosage may be used.

In addition, it is contemplated that yet additional therapies may be employed in the method of the present invention. The one or more other therapies may include, but are not limited to, administration of radiation therapy, surgical therapy, immune therapy, cytokine(s), growth inhibitory agent(s), chemotherapeutic agent(s), cytotoxic agent(s), tyrosine kinase inhibitors, ras farnesyl transferase inhibitors, angiogenesis inhibitors, and cyclin-dependent kinase inhibitors.

The chemotherapeutic agents include alkylating agents, anti-metabolic agents, plant alkaloids, topoisomerase inhibitors, and anticancer agents. All of these drugs affect cell division or DNA synthesis and function in some way. Some agents do not interfere with DNA, like tyrosine kinase inhibitors (Gleevec).

The use of miR-125a-5p or miR-125b according to the present invention is expanded to a genetic approach to the up-regulation or down-regulation of miR-125a-5p or miR-125b that is associated with the expression of SIRT7. In a similar aspect, the present invention is directed to a method of regulating the expression of liver cancer-related SIR17 gene using miR-125a-5p and/or miR-125b. In an embodiment, the method comprises bringing cells into contact with the miRNA or a vector encoding the miRNA that targets the SIRT7 gene. The function or activity of SIRT7 can be controlled by targeting the SIRT7 gene.

miR-125a-5p or miR-125b regulates the expression of SIRT7 by its direct interaction with the 3-UTR region of the SIRT7 gene.

Specifically, miR-125a-5p or miR-125b can inhibit or knock-out the translation of SIRT7 RNA to induce post-transcriptional gene silencing to thereby control the expression of the target mRNA. Thus, when the activity of miR-125a-5p or miR-125b is enhanced, the expression of SIRT7 can be inhibited, thereby inhibiting the growth of liver cancer cells.

Screening

Meanwhile, in still another aspect, based on the above-described finding, the present invention is directed to a method for screening a liver cancer therapeutic substance for inhibiting the expression of SIRT7.

In one embodiment the screening method comprises the steps of: (a) treating an animal cell, which express miR-125a-5p or miR-125b, with an anticancer candidate substance; and (b) selecting the anticancer candidate substance as a substance for treating liver cancer when the expression of miR-125a-5p in the animal cells was increased compared to that in a control group not treated with the anticancer candidate substance.

Animal cells that express miR-125a-5p or miR-125b include, for example, hepatocellular carcinoma cells (HCC cells), liver cancer cells, or artificially produced cancer cells. Preferably, the cells are human hepatocellular carcinoma cells (HCC cells). The cells are cultured in media and conditions, which can be generally selected by those skilled in the art.

In the method of the present invention, measurement of the expression of miR-125a-5p or miR-125b does not limit the configuration of biomarkers, including RNA, DNA, protein or the like.

The expression of various biomarkers in a sample can be analyzed by a number of methodologies, many of which are known in the art and understood by the skilled artisan, including but not limited to, immunohistochemical and/or Western analysis, quantitative blood based assays (as for example Serum ELISA) (to examine, for example, levels of protein expression), biochemical enzymatic activity assays, in situ hybridization of mRNA, Northern analysis and/or PCR analysis of mRNAs, as well as any one of the wide variety of assays that can be performed by gene and/or tissue array analysis.

For example, the method may comprise a protocol that examines mRNA expression in a tissue or cell sample. Methods for evaluating mRNA in cells are known and include, for example, hybridization assays utilizing complementary DNA probes, and various RNA amplification assays (e.g., RT-PCR utilizing complementary primers). In addition, the method may comprise a protocol that examines or detects mRNA in a tissue or cell sample by microarray technology. Microarray technology uses RNA hybridization technology and computer technology to evaluate the mRNA expression profile of several thousands of genes in a single experiment.

I. Use of SIRT7 as Novel Cancer Therapeutic Target

Data were calculated as mean±SD or analyzed using unpaired two tailed Student's t test [Prism 4.00 (GraphPad Software)] P<0.05 was considered statistically significant.

Materials and Methods

I-1. Cell Culture, Drug Treatment and plasmid

This study was approved by the Institutional Review of Board (IRB) of the Medical College, the Catholic University of Korea (IRB approval number: CUMC09U111). 35 HCC tissues and 27 non-tumor liver tissues were obtained from the College of Medicine, Yonsei University after obtaining IRB approval. Human hepatocellular carcinoma cell lines (SNU-182, -354, -368, -387, -423, -449 and -475) were purchased from KCLB (Korean Cell Line Bank, Seoul, South Korea), and Hep3B, HepG2 PLC/PRF/5 and normal liver cell THLE-3 were purchased from ATCC (Manassas, Va., USA). Each of the cell lines was grown in RPMI1640 media supplemented with 10% FBS (fetal bovine serum; Sigma, St Louis, Mo.) and 100 units/ml of each of penicillin and streptomycin. Cultures were incubated in a humidified 5% $CO_2$ incubator at 37° C. In the mitotic division stage, Hep3B and SNU-449 cells were synchronized at the metaphase/anaphase by nocodazole treatment (100 ng/ml for 18 hours; Sigma). pME18S-HDAC1 and pME18S-HDAC2 plasmids were obtained from Dr. Edward Seto (H. Lee Moffitt Cancer Center & Research Institute). As wild-type and dominant negative (R248W) p53 expression plasmids, pCMVneo-bam wt-p53 (encoding human wild type p53) and pCMV-Neo-Bam mt-p53 were used. The full-length cDNA of each of HDAC6 and SIRT1 was inserted into pcDNA3.1/His and pcDNA3.1/Myc-His.

I-2. SIRT7 (Sirtuin7) Gene Silencing by siRNA

SIRT7-specific siRNA was designed and purchased from Silencer Pre-designed siRNAs (www.ambion.com), and the siRNA that targets the SIRT7 gene was transfected into Hep3B, SNU-368 and SNU-449 cells.

The sequences of the siRNA are as follows:

```
si-SIRT7-sense
                               (SEQ ID NO: 3)
ACGGGAACAUGUACAUUGAtt si-SIRT7-anti sense
                               (SEQ ID NO: 4)
UCAAUGUACAUGUUCCCGUgg si-Cont-sense
                               (SEQ ID NO: 5)
CCUACGCCACCAAUUUCGUtt si-Cont-anti sense
                               (SEQ ID NO: 6)
ACGAAAUUGGUGGCGUAGGtt
```

I-3. Microarray Analysis of Whole Genome Expression

For each of experimental conditions, total RNA was extracted from 3 independent sets of the corresponding cell line using TRIzol reagent (Invitrogen), followed by clean up on Ambion columns (Illumina Total-Prep RNA Amplification Kit, Ambion). Then, RNA pools were obtained by mixing equal quantities of total RNA from three independent RNA extractions.

Biotin-labeled cRNA targets were synthesized starting from 1.5 μg of total RNA. Double stranded cDNA synthesis was performed using the Illumina® TotalPrep RNA Amplification Kit (Ambion), and biotin-UTP-labeled antisense RNA was transcribed in vitro using the Ambion Kit. All steps of the labeling protocol were performed according to Ambion's instructions (http://www.ambion.com/techlib/prot/fm_IL1791.pdf).

The size and the accuracy of targets were checked using the Experion electrophoresis system (Biorad Laboratories., Hercules, Calif.), prior to and after cRNA purification. After purification, targets were diluted in hybridization buffer at 240 ng/μl, and hybridization was allowed to proceed at 58° C. for 20 hours.

For microarray analysis, the Illumina HumanHT-12 v4 Sentrix Expression BeadChip (Illumina, San Diego, Calif.) was used. Hybridization of labeled cRNA to the BeadChip, washing, and scanning were performed as described in the Illumina BeadStation 500x manual. Array signals were developed by incubation with streptavidin-Cy3 for 10 min. The HumanHT-12 v4 Sentrix Expression BeadChip was washed, and then dried by centrifugation for 4 min at 275× g. The arrays were scanned on an Illumina BeadArray reader (a confocal-type imaging system using laser illumination at 532 (Cy3) nm). Data from each sample were extracted using Genome Studio software (Illumina) using default parameters and then analyzed using GenePix® Pro 5.1 software (Axon Instruments., Union, Calif.). The primary microarray data are available in the GEO database (GSE31338).

I-4. MTT Assay for Cell Viability

Hep3B, SNU-368 and SNU-449 cells were seeded onto 12-well plates at a density of 5000 cells/well, cultured for 24 hours, and then transfected with siRNAs. Cell proliferation was measured using a methylthiazolyl blue tetrazolium bromide (3-(4,5-dimethylthiazol-2-yl)-2, 5-diphenytetrazolium, Calbiochem) by a colorimetric dye assay. At each time point, cells were incubated with the MTT dye (5 mg/ml in 1 ml of RPMI1640) for 3 hours at 37° C. The formazan crystals were dissolved by adding 500 μl DMSO to each well, and absorbance was read at 570 nm using the VICTOR3™ Multilabel Plate Readers (PerkinElmer, Foster City, Calif., USA). All measurements were performed in triplicate and each experiment was repeated at least three times.

I-5. Western Blot Analysis

Whole-cell extracts were prepared with radioimmunoprecipitation (RIPA) lysis buffer containing protease inhibitors. Protein concentrations were then determined using a BCA protein assay kit. RIPA lysates containing 10 µg of protein were separated by SDS-PAGE and transferred onto PVDP (polyvinylidene difluoride) membranes. Lysates prepared from cells and stomach cancer and corresponding normal tissues were analyzed by Western blotting using the following antibodies: anti-HDAC2, -HDAC6, -SIRT1, -p53, -acetyl-p53, -CDK4, -GAPDH, -p16, -alpha tubulin, and acetyl-alpha tubulin (Santa Cruz Biotechnology Inc., CA), anti-p15, -p18, -p21, p27, -cyclin D1/D3/A/B1/B, -cdc2, -Beclin1, -LC3B, and -HDAC1 (Cell Signaling Technology Inc. Danvers, Mass.).

The ECL plus Western blotting detection system was used to detect bound antibodies. The intensities of Western blot bands were quantified using an LAS 3000 densitometer.

I-6. Subcellular Fractionation and SIRT7 Enzyme Analysis

Hep3B cell fractional ion into cytosol and nuclear fractions was performed using a nuclear/cytosol fractionation kit (BioVision). The deacetylation activity of Sirt7 protein immunoprecipitated from the nuclear fraction was evaluated using acetylated p53 peptide (p53-382/diAc) and Sirt1 Fluorometric Drug Discovery kit (AK-555) according to the manufacturer's (BIOMOL) protocol.

I-7. Cell Cycle Analysis

For cell cycle analysis, $4\times10^5$ cells were plated in 60-mm dishes and transiently transfected with control siRNA or SIRT7-specific siRNA or mature 'miRNA mimic. After transfection, the cells were collected by trypsinization, fixed in 70% ethanol, washed in PBS, and resuspended in 200 µl of PBS containing 1 mg-ml RNase, 0.05% Triton X100 and 50 µl/mL propidium iodide (BD biosciences, San Jose, Calif., USA). Then, the cells were incubated in the dark for 30 min at room temperature, and analyzed by flow cytometry. The data were analyzed using CellQuest Pro software (BD Biosciences).

Example I

Example I-1

Examination of Relationship of SIRT7 Expression in HCC

The expression of the SIRT7 gene in HCC groups was analyzed. From a cohort group of HCC patients available in the NCBI (National Center for Biotechnology Information) gene expression omnibus (GEO) database (accession numbers GSE25097, GSE14520, and GSE17856) and the data given as dispersion, the expression of the SIRT7 gene was analyzed.

As a result, as shown in FIG. 1A, the SIRT7 expression clearly increased from pre-malignant lesions (low- and high dysplastic nodules) to distinct cancer (Edmondson grades 1-3), and the SIRT7 gene expression was significantly up-regulated in all the three different HCC groups (see FIG. 1B). The increased expression of the SIRT7 protein was also confirmed by Western blotting of 10 randomly selected human HCC tissues (see testing set in FIG. 1C).

Also, in order to examine the molecular function of SIRT7 in carcinogenesis in the liver, SIRT7 knockdown was induced by RNA-interference, and an MTT cell proliferation assay was performed. As a result, it was shown that SIRT7 knockdown resulted in a significant decrease in the expression of SIRT7 protein and also resulted in a decrease in the proliferation rate of Hep3B, SNU-368 and SNU-449 liver cancer cells (see FIGS. 1D to 1F).

From these results, the present inventors could confirm that the development and progression of liver cancer can be determined by analyzing the expression of SIRT7. Particularly, it could be seen that, as liver cancer developed or the degree of progression thereof increased, the expression of SIRT7 increased compared to normal levels.

In addition, based on the fact that the proliferation rate of liver cancer cells is decreased when the expression of SIRT7 or the activity of SIRT7 protein is inhibited, the present inventors could see that inhibition of the expression of SIRT7 or inhibition of the expression of SIRT7 protein can be a novel therapeutic method capable of preventing and treating liver cancer.

Example I-2

Examination of Rule of SIRT7 in Liver Cancer Cells

The effect of SIRT7 inhibition on the inhibition of cancer growth as confirmed in Example I-1 can be partially demonstrated by the disruption of cell growth regulation, such as cell cycle arrest, cell aging or cell death in SIRT7 targeting. Thus, in the present invention, the influence of SIRT7 on cell cycle regulation and cell death mechanisms was analyzed by the following experiment.

I-2-1: Role of SIRT7 in Cell Cycle

To identify a molecular target associated with oncogenic SIRT7 activity, the analysis of whole genome expression was applied to Mock (empty vector)-treated Hep3B cells and SIRT7 shRNA-transfected Hep3B cells.

As a result, it was shown that SIRT7 knockdown restored the expression of $p21^{WAF1/Cip1}$ and influenced the expression of genes that are involved in cell growth and cell death pathways. In addition, the induction of $p21^{WAF1/Cip1}$ and the inhibition of G1/S-specific cyclin were observed in the SIRT7 siRNA-transfected Hep3B cells, suggesting that SIRT7 deregulates cell cycle regulatory proteins to interfere with G1/S phase.

Thus, in the present invention, in order to clarify the role of SIRT7 in the cell cycle, SIRT7 siRNA-transfected Hep3B and SNU-449 cells were treated with nocodazole. This treatment synchronizes the cells in G2/M phase. After separation from nocodazole blocks, the ratio of the cells in G1-phase was measured by flow cytometry.

Figure 2:
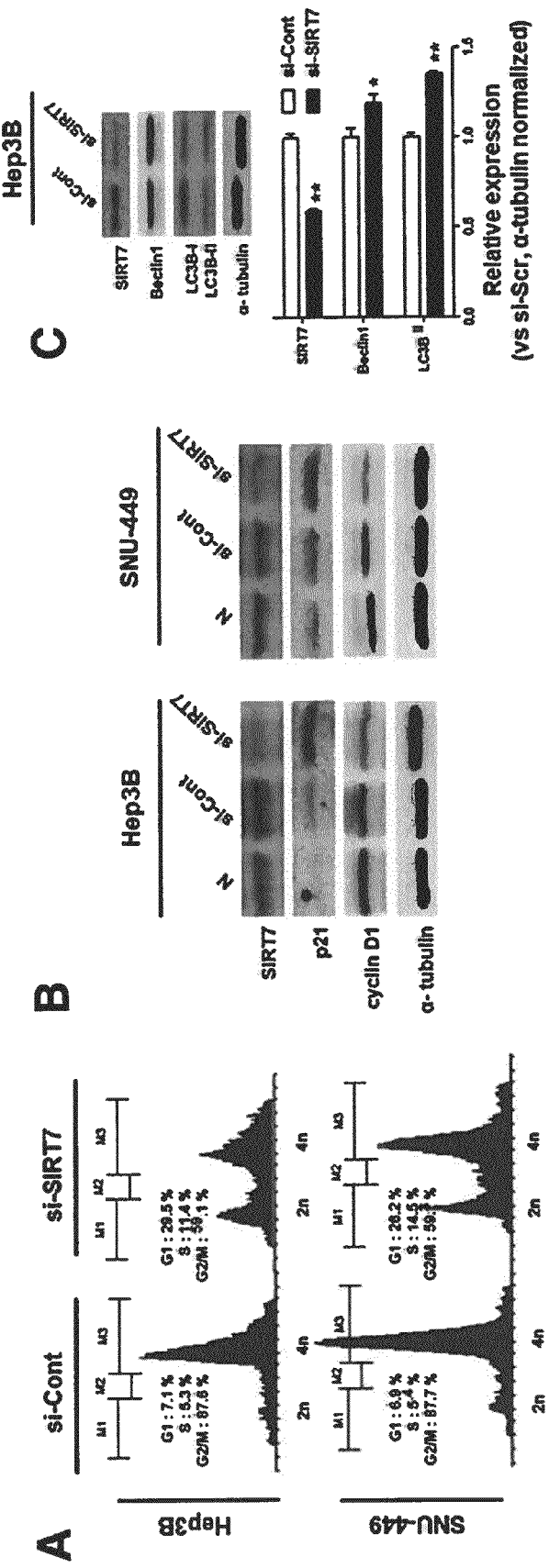
FIG. 2 shows experimental results indicating that the progression of liver cancer can be inhibited when SIRT7 is inhibited.

As a result, as shown in FIG. 2, SIRT7 knockdown resulted in a significant increase in liver cancer cells in G1/S phase and delayed cell cycle transition. This suggests that, as a result of SIRT7 knockdown, the inhibition of proliferation of liver cancer cells or the delay of growth thereof occurs, at least partially due to cell cycle interference.

Additionally, the present inventors analyzed the influence of inhibition of the activity or expression of SIRT7 on the expression of p21 and cyclin D1 in Hep3B cells and SNU-449 cells. As a result, it could be seen that inhibition of the expression of SIRT7 selectively induced the expression of $p21^{WAF1/Cip1}$ and, at the same time, inhibited the expression of cyclin D1 among G1/S cell cycle regulatory proteins (see FIG. 2B). Such results indicate that SIRT7 in liver cancer cells actively inhibits cell cycle checkpoints such as $p21^{WAF1/Cip1}$ and regulates the activity of cyclin D1 to promote G1/S transition.

Based on the gene expression analysis, the influence of SIRT7 on the expression of LC3B-II and autophagy regulatory protein Beclin-1 was analyzed. As a result, as can be seen in FIG. 2C, inhibition of the expression of SIRT7 up-regulated the expression of LC3B-II and pro-autophagic protein Beclin-1.

Such results suggest that abnormal regulation of SIRT7 causes the deregulation of cell cycle regulatory proteins in hepatocarcinogenesis and causes mitogenic stimulation by autophagy-related protein.

I-2-2: Role of SIRT7 on Protein Synthesis System

Recent studies showed that SIRT7 can be a positive regulator of an RNA polymerase I transcription system and appears at high levels in metabolically activated tissues such as liver, spleen, testicles, and carcinoma types. Because modification of a protein synthesis system, such as ribosome production, is an essential cellular process that is controlled by the progression of malignant tumor, the biological function of SIRT7 in the protein synthesis system of liver cancer cells was analyzed. As a result, it was shown that the expressed SIRT7 protein is present in the nuclear fraction of cells and that SIRT7 is nucleolar sirtuin of liver cancer cells (see FIG. 3A).

Further, it was shown that the deacetylation activity of SIRT7 on p53 as a substrate significantly increased in an immunoprecipitate of an SIRT7 antibody against the nuclear fraction of Hep3B cells. In addition, the ectopic protein synthesis of Hep3B cells was evaluated and compared with that of SIRT7-inactivated Hce3B cells, because ribosomal gene (rDNA) is associated with the ability of cells to translate mRNA. For analysis, Hep3B, SNU-368, SNU-449 and Huh7 cells were transfected with various expression plasmids, including pME18SHDAC2 (HDAC2 expression vector), pcDNA3.1_HDAC6 (HDAC6 expression vector), pcDNA3.1_SIRT1 (SIRT1 expression vector) and pCMV-Neo-Bam p53-wt (wild type p53 expression vector). Then, whether the expressions of the proteins by the expression vectors are influenced by SIRT7 was analysed.

Figure 3:
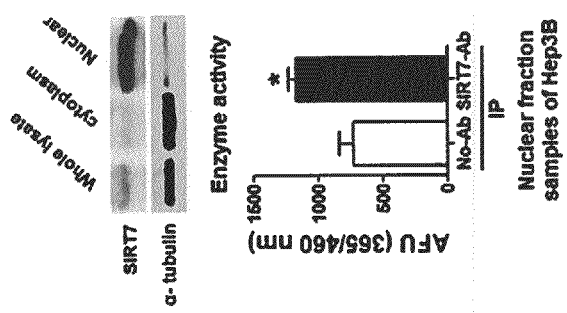
FIG. 3A shows the results of examining the intracellular position of SIRT7.
FIG. 3B shows the results of Western blot analysis performed to examine the effect of inhibition of the expression of SIRT7 on the expression of ectopic protein synthesis machineries in liver cancer cell lines.
Figure 3:
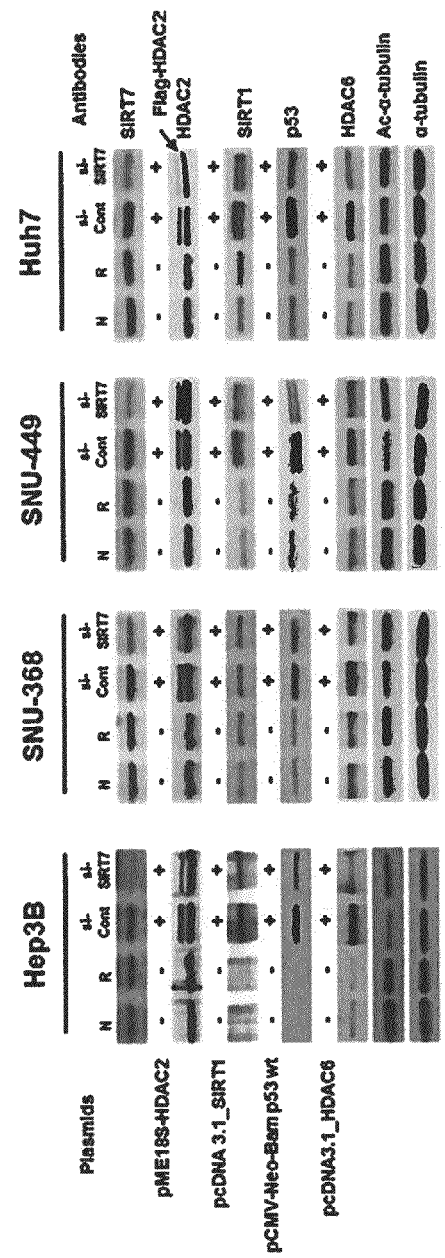

As a result, as can be seen in FIG. 3B, all the ectopic plasmids were successfully expressed. In addition, the expression of the proteins was analyzed by immunoblotting with antibodies, and as a result, it was shown that the expression of the proteins was inhibited when the expression of SIRT7 was inhibited by treatment with si-SIRT7. Additionally, the influence of SIRT7 on the ectopic expression of deacetylase that is potential alpha-tubulin deacetylase was analyzed, and as a result, it was shown that the ectopic expression of HDAC6 resulted in a decrease in acelylated endogenous alpha-tubulin, whereas the inhibition of SIRT7 expression resulted in a decrease in HDAC6 expression and restored acetylated alpha-tubulin.

Example I-3

Examination of the Effect of Inhibition of SIRT7 on Treatment of Liver Cancer

I-3-1: Analysis of the Influence of SIRT7 on Proliferation of Liver Cancer Cells Further, the present inventors performed the following experiment in order to verify whether the inhibition of SIRT7 expression can treat liver cancer. Specifically, in a Hep3B cell line in which the expression of SIRT7 was inhibited with siRNA, the cell number was measured with time. For an accurate experiment, the cell number was measured in three Hep3B cell groups (KD1, KD2 and KD3) in which the expression of SIRT7 was inhibited with each of three siRNAs. As a control group, a Hep3B cell group introduced with each of mock1 and mock2 was used.

Figure 4:
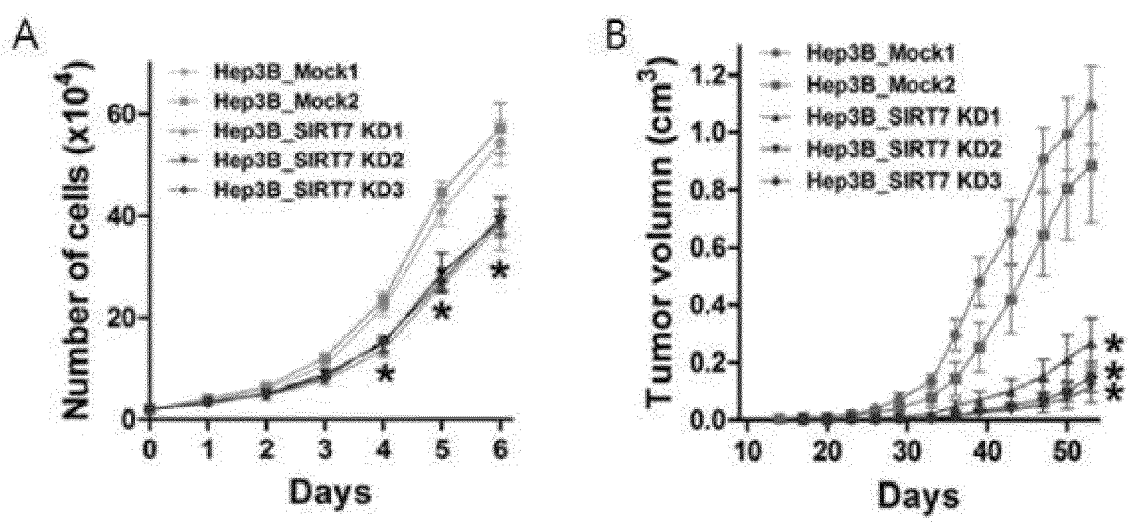
FIG. 4 shows the effect of inhibition of SIRT7 expression on the treatment of liver cancer.

As a result, as shown in FIG. 4A, the cell number of the Hep3B cell groups in which SIRT7 expression was inhibited with siRNA was decreased compared to that of the control Hep3B cell group introduced with mock1 or mock2.

Such results suggest that, when the expression of SIRT7 is inhibited, the proliferation of liver cancer cells can be inhibited, thereby inhibiting the progression or development of liver cancer.

I-3-2: Analysis of Influence of SIRT7 in Liver Cancer Mouse Model

In addition, the present inventors performed an in vivo experiment in order to verify whether the inhibition of SIRT7 expression has the effect of preventing or treating liver cancer. Specifically, each of siRNA-SIRT7s (KD1, KD2 and KD3) as used in Example I-3-1 was injected into liver cancer mice. In a control group, mice injected with each of mock1 and mock2 were used. The size of tumors in the test group and control group mice was measured using calipers for 50 days, and the volume of the tumor was calculated using the following equation:

$$\text{Tumor volume (cm}^3\text{)} = 0.52 \times (W)^2 \times (L)$$

wherein L is the rumor length, and W is tumor width. The results of the measurement were expressed as mean ±SEM, and the data were analyzed using Student's Test (p<005 versus Hep3B_Mock1).

As a result, as can be seen in FIG. 4B, the tumor volume of the mice in which the expression of SIRT7 was inhibited was at least four times smaller than that of the mice in which SIRT7 was expressed.

Putting these results together, it can be seen that SIRT7 can be used as a diagnostic biomarker capable of diagnosing the onset of liver cancer and that an inhibitor capable of inhibiting the expression or activity of SIRT7 can be used as an agent for treating liver cancer.

II. Method for Treatment of SIRT7-Expressing Cancer

The present invention relates to the use of miR-125a-5p and miR-125b to control of the expression of the cancer marker SIRT7, and more particularly to the use of the miRNAs as a target for the diagnosis and treatment of liver cancer. The analysis of these miRNAs can provide information for the prediction of liver cancer development and proliferation, cancer metastasis, or cell cycle transition.

Materials and Methods

II-1. Cell Culture, Drug Treatment and Plasmid

This study was approved by the Institutional Review of Board (IRB) of the Medical College, the Catholic University of Korea (IRB approval number: CUMC09U111). 35 HCC tissues and 27 non-tumor liver tissues were obtained from the College of Medicine, Yonsei University after obtaining IRB approval.

Human hepatocellular carcinoma cell lines (SNU-182, -354, -368, -387, -423, -449 and -475) were purchased from KCLB (Korean Cell Line Bank, Seoul, South Korea), and Hep3B, HepG2 PLC/PRF/5 and normal liver cell line THLE-3 were purchased from ATCC (Manassas, Va., USA). Each of the cell lines was grown in RPMI1640 media supplemented with 10% FBS (fetal bovine serum; Sigma, St Louis, Mo.) and 100 units/ml of each of penicillin and streptomycin. Cultures were incubated in a humidified 5% $CO_2$ incubator at 37° C.

In the mitotic division stage, Hep3B and SNU-449 cells were accumulated at the metaphase/anaphase by nocodazole treatment (100 ng/ml for 18 hours; Sigma). pME18S-HDAC1 and pMF18S-HDAC2 plasmids were obtained from Dr. Edward Seto (H. Lee Moffitt Cancer Center & Research Institute). As wild-type and dominant negative (R248W) p53 expression plasmids, pCMVneo-bam wt-p53 (encoding human wild type p53) and pCMV-Neo-Bam mt-p53 were used. The full-length cDNA of each of HDAC6 and SIRT1 was inserted into pcDNA3.1/His and pcDNA3.1/Myc-His.

II-2. Luciferase Reporter Assay

A psiCHECK-2 vector (Promega, Madison, Wis., USA) was used for cloning of SIRT7 mRNA into the 3' UTR. The vector includes the multiple cloning region downstream of the stop codon of SV40 promoter-derived Renilla luciferase gene. Based on the Renilla luciferase activity, the effect of the 3' UTR on transcriptional stability and translational efficiency was evaluated. The psiCHECK-2 vector also includes firefly luciferase gene that is constitutively expressed. Transfection was normalized using firefly luciferase.

Primer sequences used for the site-specific mutation of the SIRT7 reporter vector are as follows:

```
SIRT7-3UTR-F
                                            (SEQ ID NO: 9)
CCGCTCGAGCGGTCACGTGCTCGATGAAGAACAG

SIRT7-3UTR-R
                                            (SEQ ID NO: 10)
ATTTGCGGCCGCTTTAGCCAGTGCAGAAACGTTTAATAG

SIRT7-3UTR-125 mt-F
                                            (SEQ ID NO: 11)
CGCTCACCAGGCCAGTGAGTGCGCCTCACCGTATTTC

SIRT7-3UTR-125 mt-R
                                            (SEQ ID NO: 12)
AAATACGGTGAGGCGCACTCACTGGCCTGGTGAGCG

SIRT7-3UTR-148 mt-F
                                            (SEQ ID NO: 13)
CCTTGAGGAAGCCCCTTCGTGTGCTGCGGTTGTACCC

SIRT7-3UTR-148 mt-R
                                            (SEQ ID NO: 14)
GGGTACAACCGCAGCACACGAAGGGGCTTCCTCAAGG

SIRT7-3UTR-193 mt-F
                                            (SEQ ID NO: 15)
CCTTTCCTCGCTCACCAGCGGTGTCTCAGGGCCTCACCG

SIRT7-3UTR-193 mt-R
                                            (SEQ ID NO: 16)
GGTGAGGCCCTGAGACACCGCTGGTGAGCGAGGAAAGG
```

24 hours before transfection, Hep3B cells were seeded into each well of 12-well plates, and each well was transfected with a mixture of 250 ng 3' UTR luciferase reporter vector and 200 nM miRNA mimic. 24 hours after transfection, the cells were lysed, and luciferase activity was measured on a luminometer (Victor3, PerkinElmer Inc., Foster City, Calif., USA) by Dual-Luciferase Reporter Assay System (Promega).

The ratio of Renilla luciferase to firefly luciferase was calculated.

II-3. SIRT7 (Sirtuin7) Gene Silencing by Small-Interference RNA (siRNA)

SIRT7-specific siRNA was designed and purchased from Silencer Pre-designed siRNAs (www.ambion.com), and the siRNA that targets the SIRT7 gene was transfected into Hep3B, SNU-368 and SNU-449 cells.

The sequences of the siRNA are as follows:

```
si-SIRT7-sense
                                            (SEQ ID NO: 3)
ACGGGAACAUGUACAUUGAtt si-SIRT7-anti sense
                                            (SEQ ID NO: 4)
UCAAUGUACAUGUUCCCGUgg si-Cont-sense
                                            (SEQ ID NO: 5)
CCUACGCCACCAAUUUCGUtt si-Cont-anti sense
                                            (SEQ ID NO: 6)
ACGAAAUUGGUGGCGUAGGtt
```

II-4. RNA Isolation and RT-PCR Analysis

For RT-PCR analysis of mature miRNA, total RNA was isolated from each cell line using Trizol reagent (Invitrogen). Using Taqman MicroRNA Reverse Transcription Kit (Applied Biosystems), 0.1 μg of total RNA was reverse-transcribed into cDNA. Comparative RT-PCR was performed in triplicate using Qarta PCR Master Mix (qARTA Bio., Fremont, Calif., USA) in Bio-Rad iQ5 real-time PCR system. Mature miRNA mimic and mature miRNA-specific primer sequences used in RT-PCR are as follows:

```
Mature miRNA
hsa-miR-125a-5p (MIMAT0000443)
                                            (SEQ ID NO: 17)
UCCUGAGACCCUUUAACCUGUGA hsa-miR-125b (MIMAT0000423)
                                            (SEQ ID NO: 18)
UCCCUGAGACCCUAACUUGUGA hsa-miR-148a (MIMAT0000243)
                                            (SEQ ID NO: 19)
UCAGUGCACUACAGAACUUUGU hsa-miR-152 (MIMAT0000438)
                                            (SEQ ID NO: 20)
UCAGUGCAUGACAGAACUUGG hsa-miR-193a-3p (MIMAT0000459)
                                            (SEQ ID NO: 21)
AACUGGCCUACAAAGUCCCAGU Primer (real time PCR)
U6 snRNA-RT:
                                            (SEQ ID NO: 22)
GTCGTATCCAGTGCAGGGTCCGAGGTATTCGCACTGGATACGACAAAAAT
ATGG hsa-miR-125a-5p-RT:
                                            (SEQ ID NO: 23)
GTCGTATCCAGTGCAGGGTCCGAGGTATTCGCACTGGATACGACTCACAG hsa-miR-125b-RT:
                                            (SEQ ID NO: 24)
GTCGTATCCAGTGCAGGGTCCGAGGTATTCGCACTGGATACGACTCACAA hsa-miR-148a-RT:
                                            (SEO ID NO: 25)
GTCGTATCCAGTGCAGGGTCCGAGGTATTCGCACTGGATACGACACAAAG hsa-miR-152-RT:
                                            (SEQ ID NO: 26)
GTCGTATCCAGTGCAGGGTCCGAGGTATTCGCACTGGATACGACCCAAGT hsa-miR-193a-3p-RT:
                                            (SEQ ID NO: 27)
GTCGTATCCAGTGCAGGGTCCGAGGTATTCGCACTGGATACGACACTGGG U6 snRNA-F:
                                            (SEQ ID NO: 28)
GGCTGCCGAAGGATGACACGC hsa-miR-125a-5p-F:
                                            (SEQ ID NO: 29)
TCCTGAGACCCTTTAACCTGTGA hsa-miR-125b-F:
                                            (SEQ ID NO: 30)
TCCCTGAGACCCTAACTTGTGA
```

-continued hsa-miR-148a-F:
TCAGTGCACTACAGAACTTTGT
(SEQ ID NO: 31)

hsa-miR-152-F:
TCAGTGCATGACAGAACTTGG
(SEQ ID NO: 32)

hsa-miR-193a-3p-F:
AACTGGCCTACAAAGTCCCAGT
(SEQ ID NO: 33)

Universal-R:
GTGCAGGGTCCGAGGT
(SEQ ID NO: 34)

Primer (MSP)
miR-125b-U-F
GGGAAAATGAGAGTTTTTAGTGTGT
(SEQ ID NO: 35)

miR-125b-U-R
CAATCTCAAAATTTAATATATCACT
(SEQ ID NO: 36)

miR-125b-M-F
GAAAATGAGAGTTTTTAGTGCGT
(SEQ ID NO: 37)

miR-125b-M-R
CAATCTCGAAATTTAATATATCGCT
(SEQ ID NO: 38)

Normalization to the U6 snRNA primer was performed, and the relative level of mature miRNA was calculated with $x=2^{-\Delta Ct}$, wherein $\Delta C=Ct_{Target\ miRNA}-Ct_{U6}$.

II-5. Microarray Analysis of Whole Genome Expression

For each of experimental conditions, total RNA was extracted from 3 independent sets of the corresponding cell line using TRIzol reagent (Invitrogen), followed by clean up on Ambion columns (Illumina Total-Prep RNA Amplification Kit, Ambion). Then, RNA pools were obtained by mixing equal quantities of total RNA from three independent RNA extractions.

Biotin-labeled cRNA targets were synthesized starting from 1.5 µg of total RNA. Double stranded cDNA synthesis was performed using the Illumina® TotalPrep RNA Amplification Kit (Ambion), and biotin-UTP-labeled antisense RNA was transcribed in vitro using the Ambion Kit. All steps of the labeling protocol were performed according to Amnion's instructions (http://www.ambion.com/techlib/prot/fm_IL1791.pdf).

The size and the accuracy of targets were checked using the Experion electrophoresis system (Biorad Laboratories., Hercules, Calif.), prior to and after cRNA purification. After purification, targets were diluted in hybridization buffer at 240 ng/µl, and hybridization was allowed to proceed at 58° C. for 20 hours. For microarray analysis, the Illumina HumanHT-12 v4 Sentrix Expression BeadChip (Illumina, San Diego, Calif.) was used. Hybridization of labeled cRNA to the BeadChip, washing, and scanning were performed as described in the Illumina BeadStation 500x manual. Array signals were developed by incubation with streptavidin-Cy3 for 10 min. The HumanHT-12 v4 Sentrix Expression Bead-Chip was washed, and then dried by centrifugation for 4 min at 275× g. The arrays were scanned on an Illumina BeadArray reader (a confocal-type imaging system using laser illumination at 532 (Cy3) nm). Data from each sample were extracted using Genome Studio software (Illumina) using default parameters and then analyzed using GenePix® Pro 5.1 software (Axon Instruments., Union, Calif.). The primary microarray data are available in the GEO database (GSE31338).

II-6. Analysis of Differential MicroRNA Expression Profiling of HCCs

The miRNA expression profiling of 8 normal liver tissues and 16 HCC tissues was performed using the GenoExplorer Microarray Platform (GenoSensor Corp., Tempe, Ariz.) including 1,371 miRNA sequences selected from the public database miRBase v16.

10 µg of total RNA was isolated from normal liver tissue and HCC tissue, labeled, and hybridized to microRNA chips for analysis under optimized conditions. The arrays with hybridized targets were scanned using an Axon scanner, and the scanned images were analyzed using GenePix Pro 5.0 software (Axon Instruments). Spots of poor quality determined by visual inspection were removed from further analysis. The resulting data, the average of 3 mean fluorescence signal intensities for each probe, collected from each array was submitted to the GenePlex 3.0 database (Istech Inc. Seoul, Korea).

Data were normalized using the method of quantile normalization and class-specific filtering. 510 miRNAs were used in hierarchical clustering. Pearson's correlation coefficient was calculated using Cluster and TreeView program (Stanford Univ.).

II-7. MTT Assay for Cell Viability

Hep3B, SNU-368 and SNU-449 cells were seeded onto 12-well plates at a density of 5000 cells/well, cultured for 24 hours, and then transfected with siRNAs.

Cell proliferation was measured using an MIT [methylthiazolyl blue tetrazolium bromide (3-(4,5-dimethylthiazol-2-yl)-2,5-diphenytetrazolium, Calbiochem)] by a colorimetric dye assay. At each time point, cells were incubated with the MTT dye (5 mg/ml in 1 ml of RPMI1640) for 3 hours at 37° C.

The formazan crystals were dissolved by adding 500 µl DMSO to each well, and absorbance were read at 570 nm using the VICTOR3™ Multilabel Plate Readers (PerkinElmer, Foster City, Calif., USA). All measurements were performed in triplicate and each experiment was repeated at least three times.

II-8. Western Blot Analysis

Whole-cell extracts were prepared with radioimmunoprecipitation (RIPA) lysis buffer containing protease inhibitors. Protein concentrations were then determined using a BCA protein assay kit. RIPA lysates containing 10 µg of protein were separated by SDS-PAGE and transferred onto PVDf (polyvinylidene difluoride) membranes.

Lysates prepared from cells and stomach cancer and corresponding normal tissues were analyzed by Western blotting using the following antibodies: anti-HDAC2, -HDAC6, -SIRT1, -p53, -acetyl-p53, -CDK4, -GAPDH, -p16, -alpha tubulin, and acetyl-alpha tubulin (Santa Cruz Biotechnology Inc., Calif.), anti-p15, -p18, -p21, -p27, -cyclin D1/D3/A/B1/E, -cdc2, -Beclin1, -LC3B, and -HDAC1 (Cell Signaling Technology Inc, Danvers, Mass.).

The ECL plus Western blotting detection system (Amersham biosciences) was used to detect bound antibodies. The intensities of Western blot bands were quantified using an LAS 3000 densitometer (Fuji Photo Film Co., Japan).

II-9. Subcellular Fractionation and SIRT7 Enzyme Analysis

Hep3B cell fractionation into cytosol and nuclear fractions was performed using a nuclear/cytosol fractionation kit (BioVision).

The deacetylation activity of Sirt7 protein immunoprecipitated from the nuclear fraction was evaluated using acelylated p53 peptide (p53-382/diAc) and Sirt1 Fluorometric Drug Discovery kit (AK-555) according to the manufacturer's (BIOMOL) protocol.

II-10. Cell Cycle Analysis

For cell cycle analysis, $4\times10^5$ cells were plated in 60-mm dishes and transiently transfected with control siRNA or SIRT7-specific siRNA or mature miRNA mimic.

After transfection, the cells were collected by trypsinization, fixed in 70% ethanol, washed in PBS, and resuspended in 200 µl of PBS containing 1 mg/ml RNase, 0.05% Triton X100 and 50 µl/mL propidium iodide (BD biosciences, San Jose, Calif., USA). Then, the cells were incubated in the dark for 30 min at room temperature, and analyzed by flow cytometry. The data were analyzed using CellQuest Pro software (BD Biosciences).

II-11. Mutation Assay

Genomic DNA from each of HCC tissues and corresponding non-tumor liver tissues was amplified with 6 sets of primers covering the coding region (exons 4-9) of p53 gene. Each PCR reaction was performed under standard conditions in 10 µl of a reaction mixture containing 20 ng of template DNA, 0.5 µmole of each primer, 0.2 µmole of deoxynucleotide triphosphate, 1.5 mM $MgCl_2$, 0.4 units of Taq polymerase, 0.5 µl of dCTP (Ameroharm, Buckinghamshire, UK) and 1 µl of 10× buffer. Each reaction was subjected to PCR under the following conditions: initial denaturation at 94° C. for 12 min; and then 35 cycles, each consisting of denaturation at 94° C. for 40sec, annealing at 52~57° C. for 40 sec, and extension at 72° C. for 40 sec; and then final extension at 72° C. for 5 min.

After amplification, the PCR products were denatured in a 1:1 dilution of a sample buffer containing 98% formamide/5 mmol/L NaOH at 95° C. for 5 minutes. Then, each of the materials was loaded onto a single strand conformation polymorphism (SSCP) with 10% glycerol. After electrophoresis, the gel was transferred to 3 MM Whatman paper, and then dried, followed by exposure to Kodak X-OMAT film (Eastman Kodak, Rochester, N.Y.).

For direct sequencing, the PCR products amplified using the PCR primer sets were individually extracted with a miniprep kit (Qiagen) and sequences (Cosmogenetech, Seoul, Korea). The primer sequences are shown in Table 1 below.

TABLE 1

| Exons | Sense primer Antisense primer | PCR product size (bp) | Annealing temperature (° C.) |
|---|---|---|---|
| 5 | GCTGCCGTGTTCCAGTTGCT CCAGCCCTGTCGTCTCTCCA | 294 | 58 |
| 6 | GGCCTCTGATTCCTCAGTGA GCCACTGACAACCACCCTTA | 199 | 55 |
| 7 | TGCCACAGGTCTCCCCAAGG AGTGTGCAGGGTGGCAAGTG | 196 | 56 |
| 8 | CCTTACTGCCTCTTGCTTCT ATAACTGCACCCTTGGTCTC | 225 | 55 |

II-12. Methylation-Specific PCR (MSP)

DNA was extracted, treated with bisulfate using the EZ DNA methylation kit (Zymo Research), and purified using a QiaQuick DNA purification kit (Qiagen, Valencia, Calif.).

CpG islands in a target region for the miR-125b promoter were determined using promoter scan (http://bimas.dcrt.nih.gov/molbio/proscan/) and CpG Island Searcher (http://cent.hsc.use.edu/cpgislands2/epg.aspx). The region was found in several hundreds of base pairs of a transcription start point of a miR-125b precursor.

Methylation-specific PCR (MSP) was performed using primer sequences for methylated or unmethylated DNA, designed by MethPrimer (Supplementary Table S2). Briefly, 2 µl of bisulfate-treated genomic DNA was amplified. PCR was performed under the following conditions: 95° C. for 10 min, and then 40 cycles of 30 sec at 95° C/. 30 sec at 52° C. and 30 sec at 60° C. The resulting products were loaded on 2% agarose gel. Each sample was tested in duplicate.

Example II

Example II-1

Examination of Relationship of SIRT7 Expression in HCC

Figure 5:
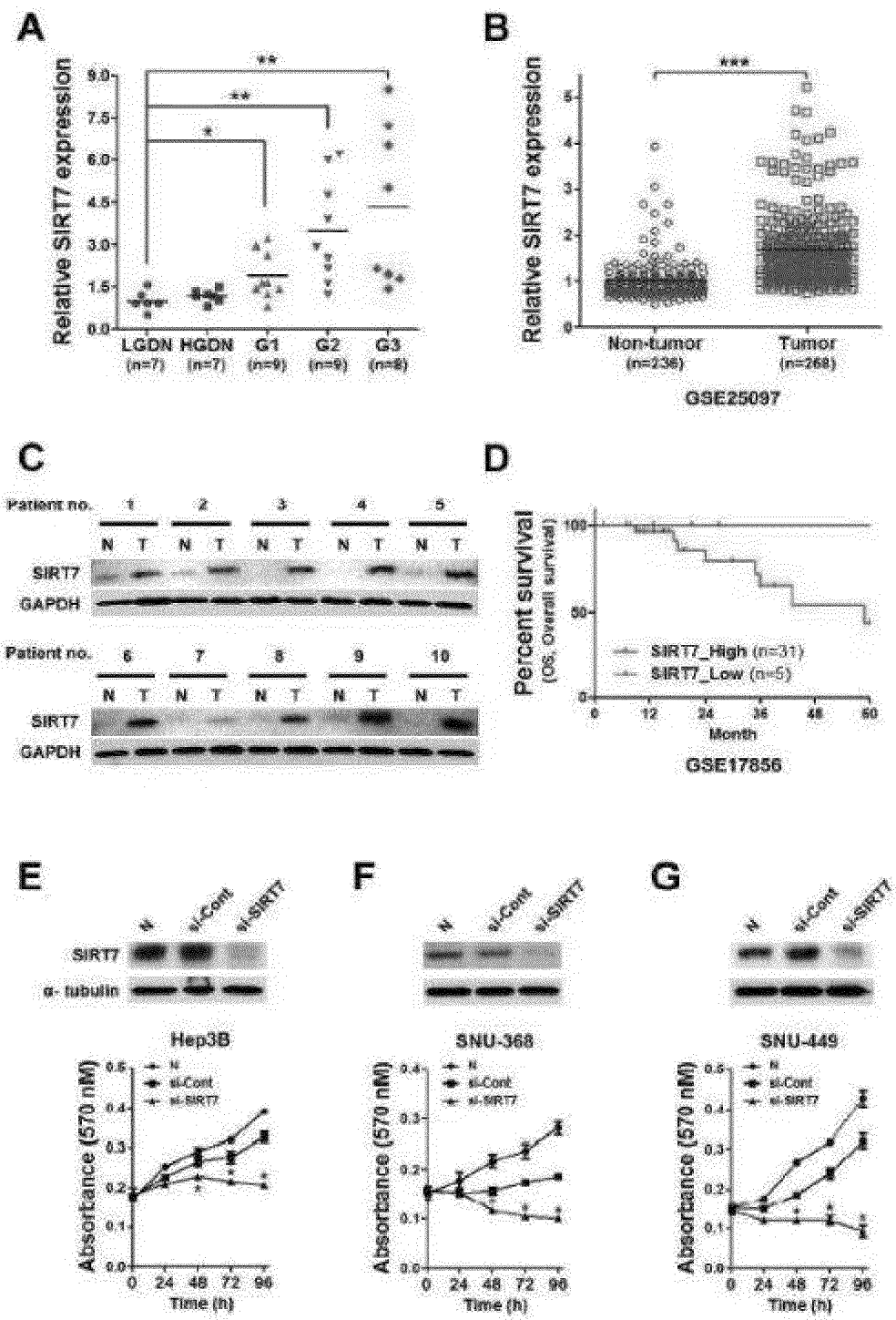
FIG. 5 shows the results related to of the association between human hepatocellular carcinoma (HCC) and SIRT7 expression.
Figure 6:
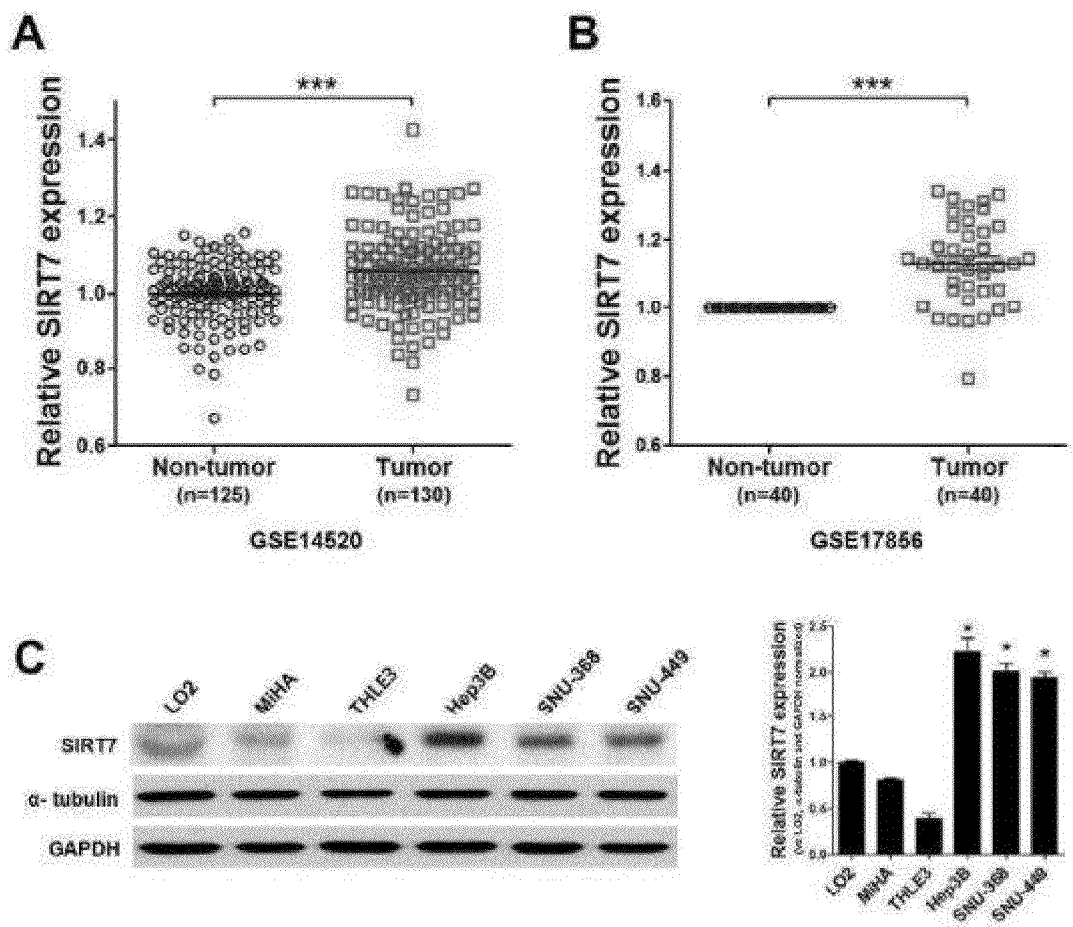
FIG. 6 shows the abnormal regulation of SIRT7 expression in HCC patients from the GEO database.

The expression of the SIRT7 gene in a HCC cohort was analyzed. From a cohort group of HCC patients available in the NCBI (National Center for Biotechnology Information) gene expression omnibus (GEO) database (accession numbers GSE25097, GSE14520, and GSE17856) and the data given as dispersion, the expression of the SIRT7 gene was analyzed. The results of the analysis are shown in FIGS. 5 and 6.

As shown in FIG. 5A, the SIRT7 expression gradually increased from pre-malignant lesions (low- and high-grade grade dysplastic nodules) to distinct cancer (Edmondson grades 1-3), and the SIRT7 gene expression was significantly up-regulated in all the three different HCC groups (see FIGS. 5B, 6A and 6B). The increased expression of the SIRT7 protein was also confirmed by Western blotting of 10 randomly selected human HCC tissues (see testing set in FIG. 5C). Human liver cancer cell lines also showed high expression levels of the SIRT7 protein compared to normal liver cell lines LO2, MiHA and THLE-3 (see FIG. 6C). Particularly, the Kaplan-Meier survival curve of HCC patients showed that the over-5-year survival rate of HCC patterns with high SIRT7expression was lower than that of HCC patients with low SIRT7 expression (see FIG. 5D).

In order to examine the molecular function of SIRT7 in carcinogenesis in the liver, SIRT7knockdown was induced by RNA-interference, and an MTT cell proliferation assay was performed. As a result, it was shown that SIRT7 knockdown resulted in a significant decrease in the expression of SIRT7 protein and also resulted in a decrease in the proliferation rate of Hep3B, SNU-368 and SNU-449 liver cancer cells (see FIGS. 5E to 5G).

Such anti-growth effects can be partially demonstrated by the disruption of cell growth regulation, such as cell cycle arrest, cell aging or cell death in SIRT7 targeting. Thus, the effect of SIRT7 inhibition on cell cycle regulation and cell death mechanisms was analyzed by the following experiment.

Example II-2

Identification of Gene Target that is Transcriptionally Silenced by SIRT7, Using Whole-Genome Scan II-2-1. SIRT7 in Cell Cycle In order to identify a molecular target associated with oncogenic SIRT7 activity, the analysis of whole genome expression was applied to Mock (empty vector)-treated Hep3B cells and SIRT7 shRNA-transfected Hep3B cells.

Figure 8:
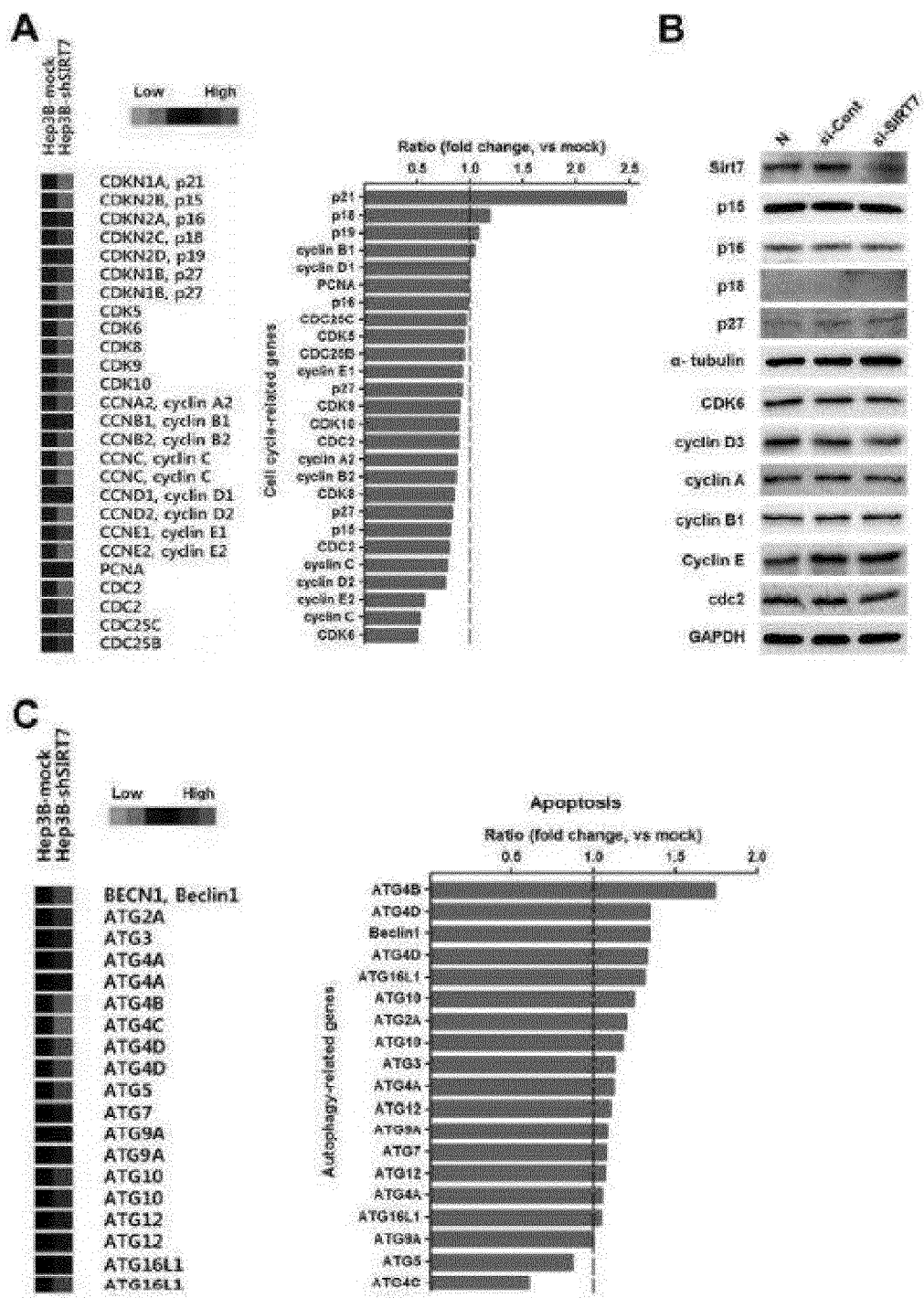
FIG. 8 shows the results of whole-genome scan for identifying a gene target that is transcriptionally silenced by oncogenic gene SIRT7.

As a result, it was shown that SIRT7 knockdown restored the expression of p21$^{WAF1/Cip1}$ and influenced the expression of genes that are involved in cell growth and cell death pathways (see FIGS. 8A and 8C). In addition, the induction of p21$^{WAF1/Cip1}$ and the inhibition of G1/S-specific cyclin were observed in the SIRT7 siRNA-transfected Hep3B cells, suggesting that SIRT7 deregulates cell cycle regulatory proteins to interfere with G1/S phase.

In order to clarify the role of SIRT7 in the cell cycle, SIRT7 siRNA-transfected Hep3B and SNU-449 cells were treated with nocodazole. This treatment synchronizes the cells at G2/M phase. After separation from nocodazole blocks, the ratio of the cells in G1-phase was measured by flow cytometry.

Figure 7:
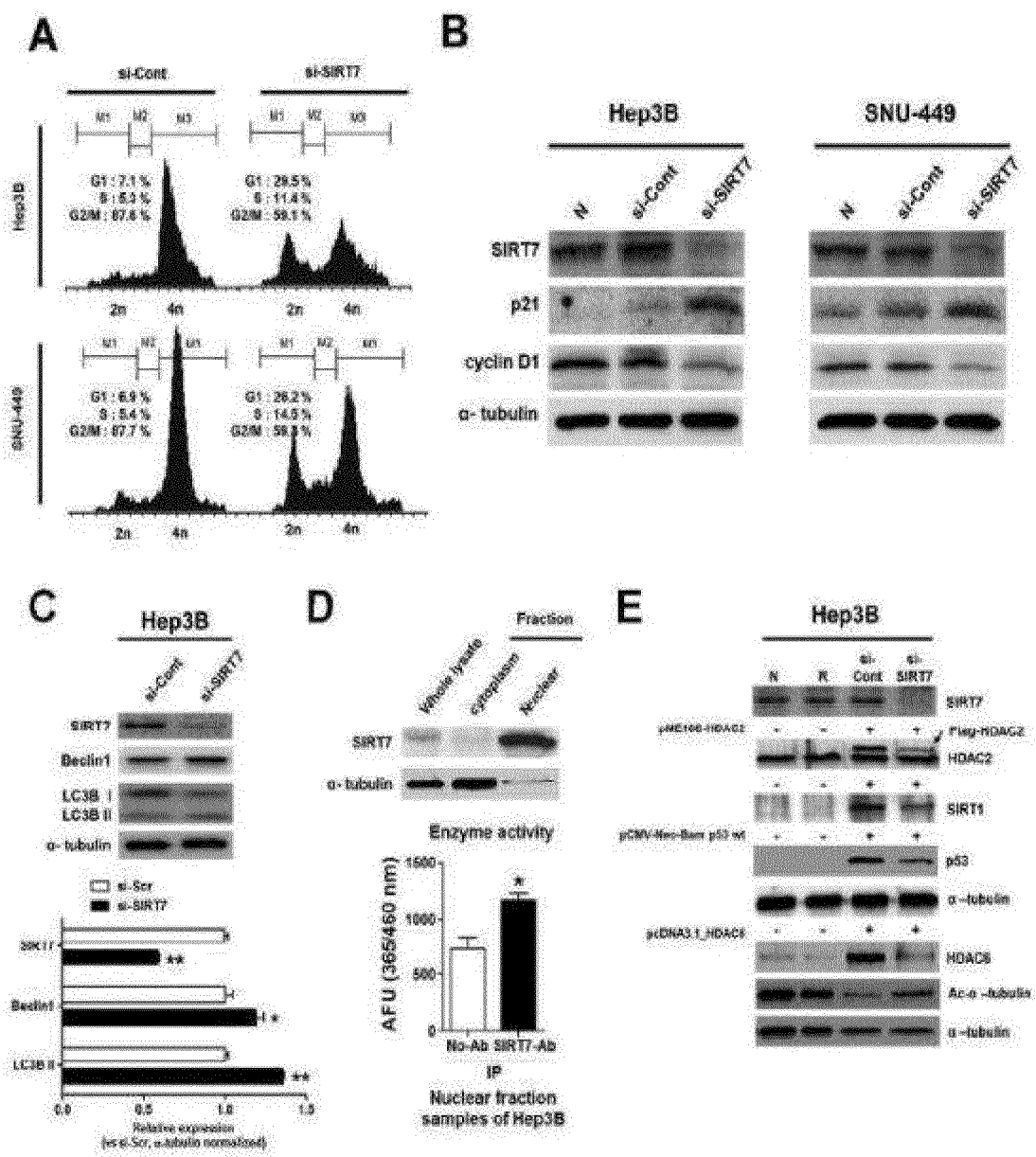
FIG. 7 shows a mechanism in which SIRT7 regulates the growth of hepatocellular carcinoma (HCC) by cell cycle regulatory proteins and autophagy-related proteins.
Figure 9:
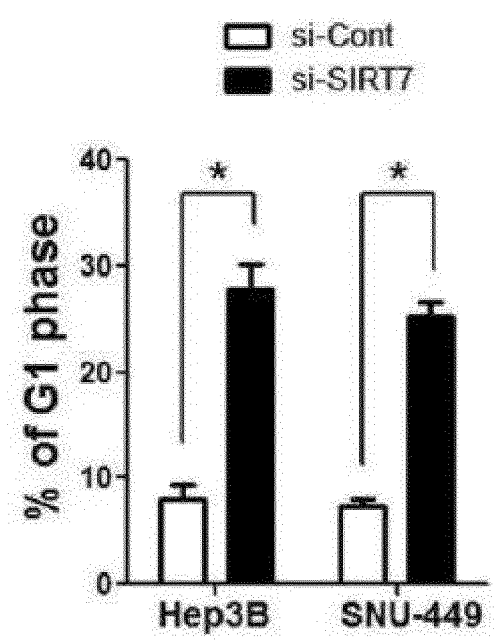
FIG. 9 shows the results of cell cycle profiling performed by nocodazole treatment.

As a result, as can be seen in FIG. 7A, SIRT7 knockdown resulted in a significant increase in liver cancer cells at G1/S phase and delayed cell cycle transition. This suggests that, as a result of SIRT7 knockdown, the inhibition of proliferation of liver cancer cells and/or the delay of growth thereof occurs, at least partially due to cell cycle interference (see FIG. 9).

Additionally, the present inventors have found that the inactivation of SIRT7 in Hep3B cells selectively induced the expression of p21$^{WAF1/Cip1}$ and, at the same time, inhibited the expression of cyclin D1 among G1/S cell cycle regulatory proteins (see FIGS. 7B and 8B). Such results indicate that SIRT7 in liver cancer cells actively inhibits cell cycle checkpoints such as p21$^{WAF1/Cip1}$ and regulates the activity of cyclin D1 to promote G1/S transition.

In addition, based on the analysis of gene expression, it can be seen that factors related to autophagic cell death were removed, including autophagy regulatory protein Beclin-1 and genes (i.e., ATGs) (see FIG. 8C). As shown in FIG. 7C, the inactivation of SIRT7 in Hep3B cells induced the expression of pro-autophagic protein Beclin-1 and conversion to LC3B-II.

In conclusion, abnormal regulation of SIRT7 causes the deregulation of cell cycle regulatory proteins in hepatocarcinogenesis and causes mitogenic stimulation by autophagy-related protein.

II-2-2. SIRT7 on Protein Synthesis System

Recent studies showed that SIRT7 can be a positive regulator of an RNA polymerase I transcription system and appears at high levels in metabolically activated tissues such as liver, spleen, testicles, and carcinoma types. Because modification of a protein synthesis system, such as ribosome production, is an essential cellular process that is controlled by the progression of malignant tumor, the biological function of SIRT7 in the protein synthesis system of liver cancer cells was analyzed.

First, the enzymatic activity and exclusive expression of SIRT7 in the nuclear fraction of Hep3B cells were detected, suggesting that SIRT7 is a nucleolar sirtuin of liver cancer cells (see FIG. 7D).

It was observed that the deacetylation activity of SIRT7 on p53 as a substrate significantly increased in an immunoprecipitate of an SIRT7 antibody against the nuclear fraction of Hep3B cells. In addition, the ectopic protein synthesis of Hep3B cells was evaluated and compared with that of SIRT7-inactivated Hep3B cells, because ribosomal gene (rDNA) is associated with the ability of cells to translate mRNA. Then, Hep3B cells were transfected with various expression plasmids, including pME18SHDAC2 (HDAC2 expression vector), pcDNA3.1-HDAC6 (HDAC6 expression vector), pcDNA3.1_SIRT1 (SIRT1 expression vector) and pCMV-Neo-Bam p53-wt (wild type p53 expression vector).

As can be seen in FIG. 7E, all the ectopic plasmids were expressed successfully and detected by immunoblotting with antibodies. However, SIRT7 inactivation inhibited the protein expression of the ectopic plasmids, indicating disruption of the protein synthesis system.

In order to further verify the effect of SIRT7 inactivation, transfection with a HDAC6 expression vector (pcDNA3.1_HDAC6) was performed, because HDAC6 is potential alpha-tubulin deacetylase.

As shown in FIG. 7E, the ectopic expression of HDAC6 resulted in a decrease in acetylated endogenous alpha-tubulin, whereas the inactivation of SIRT7 resulted in a decrease in HDAC6 expression and restored acetylaled alpha-tubulin. This suggests that the inaciivation of SIRT7 plays a positive role in the protein synthesis system of Hep3B cells.

Example II-3

Endogenous MicroRNAs for Controlling SIRT7 Regulation in Liver Cancer

The loss or gain of miRNA function contributes to the development of cancer by up-regulation and silencing. In order to identify a mechanism that induces SIRT7 expression in liver cancer cell, miRNA expression profiling analysis was performed to identify miRNAs that are abnormally regulated in human HCC.

Figure 10:
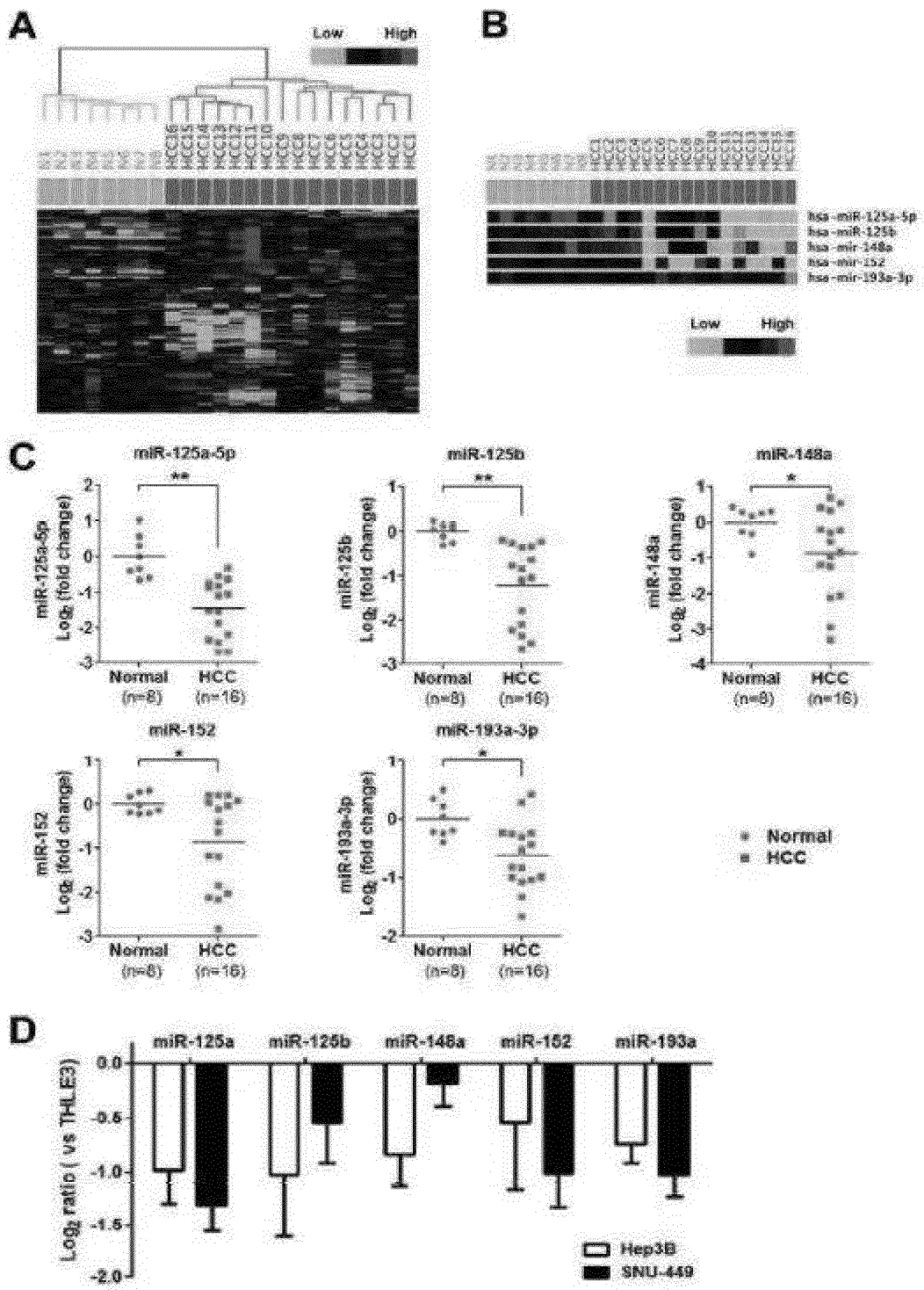
FIG. 10 shows the results of analyzing the expression profiling of different miRNAs in HCC and identifying miRNAs that target SIRT7.

As shown in FIG. 10A, two distinct cluster results were obtained by unsupervised hierarchical clustering analysis of 510 miRNAs selected by minimum filtering of 1,371 miRNAs of 8 non-tumor liver tissues and 16 HCCs, suggesting characteristic miRNA signals associated with liver carcinoma, particularly HCC.

Then, miRNAs that target SIRT7 were predicted using target prediction program miRanda (http://www.microrna.org). As a result, 5 miRNAs (miR-125a-5p, 125b, 148a, 152 and 193a-3p) which were significantly down-regulated in HCC were identified (sec FIG. 10B). As shown in FIG. 10C, the values of miRNA expression array data were significantly lower in HCC than in non-tumor liver tissue.

To examine the inhibition of the miRNAs in HCC, the RT-PCR analysis of the five miRNAs in Hep3B and SNU-449 cells was performed, and the results were compared with those in normal liver cell line THLE-3.

As expected, the expressions of all the five miRNAs in Hep3B and SNU-449 were significantly lower than those in THLE-3 (see FIG. 10D).

Example II-4

Examination of Functions of miR-125a-5p and miR-125b

Figure 11:
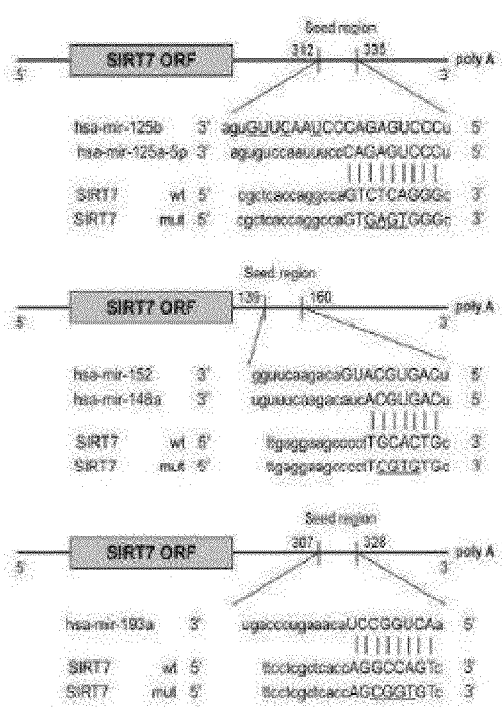
FIG. 11 shows the results of SIRT7 3'UTR targeting and miRNA expression in HCC patients.
Figure 11:
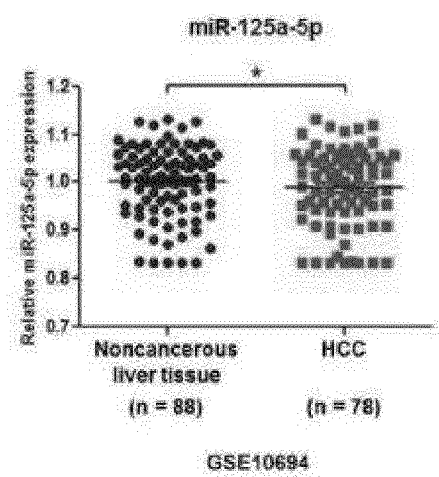
Figure 11:
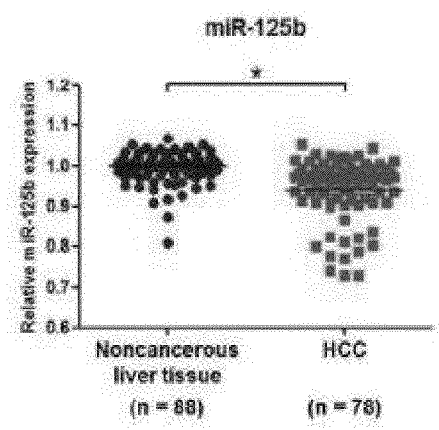

In order to examine whether such miRNAs interact directly with the 3-UTR region of the SIRT7 gene so that SIRT7 is selectively regulated, SIRT7 3-UTR was cloned into a reporter vector-linked luciferase open reading frame to construct psiCHECH2-SIRT7_3-UTR wild type (psiCHECK2-SIRT7-wt) vector. In addition, SIRT7 3-UTR with any mutation was cloned to construct mutant-type reporter vector (psiCHECK2-SIRT7-mt) (see FIG. 11A). Each of the vectors was co-transfected with each of the five different miRNAs into each of Hep3B and SNU-449 cell lines. The results of dual-luciferase reporter analysis of the psiCHECK2-SIRT7-wt plasmids having the five miRNAs were compared with those of the psiCHECK2-SIRT7-mt plasmids and graphically shown in FIGS. 12A and 12B.

As can be seen therein, miR-125a-5p, miR-125b, miR-148a and miR-152 could inhibit reporter gene activity in both the Hep3B and SNU-449 cell lines, whereas miR-193a-3p had no effect. This suggests that the four miRNAs can regulate the in vitro expression of SIRT7 in HCC cells.

In addition, whether the ectopic expression of the five miRNAs in liver cancer cells resembles the SIRT7-inactivating effect of siRNA was evaluated.

Figure 12:
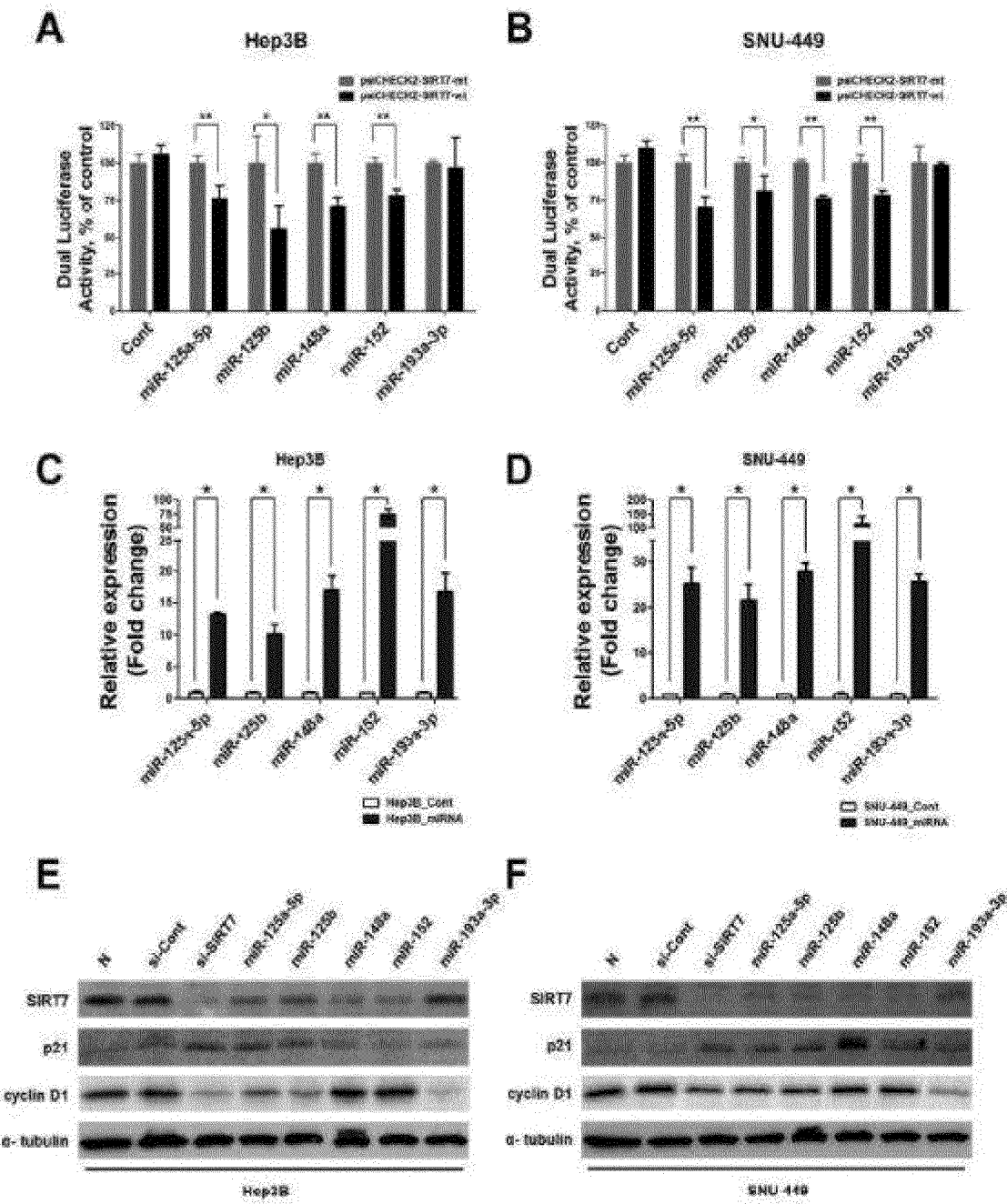
FIG. 12 shows experimental results indicating that miR-125a-5p and miR-125b are endogenous regulators of SIRT7 expression in hepatocarcinogenesis.

As a result, as shown in FIGS. 12C and 12D, high levels of endogenous miRNAs were detected in both the Hep3B and SNU-449 cell lines after ectopic of the five miRNAs.

These results were consistent with the luciferase analysis results, suggesting that miR-125a-5p, miR-125b, miR-148a and miR-152 can inhibit the expression of endogenous SIRT7 (see FIGS. 12E and 12F), like SIRT7 siRNA did in Hep3B and SNU-449 cells. However, only miR-125a-5p and miR-125b selectively restored $p21^{WAF1/Cip1}$ and inhibited cyclin D1, like SIRT7 siRNA did in Hep3B and SNU-449 cells. Particularly, when the expression data of miR-125a-5p and miR-125b in HCC patients from the GEO database (GSE10694) were evaluated, miR-125a-5p and miR-125b all showed the ability to significantly down-regulate SIRT7 expression in HCC compared to non-tumor liver tissue (see FIGS. 11B and 11C).

Although the reason why miR-148a and miR-152 did not influence the expression of such cell cycle regulatory proteins is not clear, such results suggest that miR-125a-5p and miR-125b are regulators against SIRT7 in hepatocarcinogenesis.

In addition, in order to verify that miR-125a-5p and miR-125b are endogenous regulators of SIRT7 in liver cancer cells, analysis was performed to examine whether the ectopic expression of miR-125a-5p and miR-125b delays cancer cell growth by cell cycle arrest, like the inactivation of SIRT7 in liver cancer cells.

Figure 13:
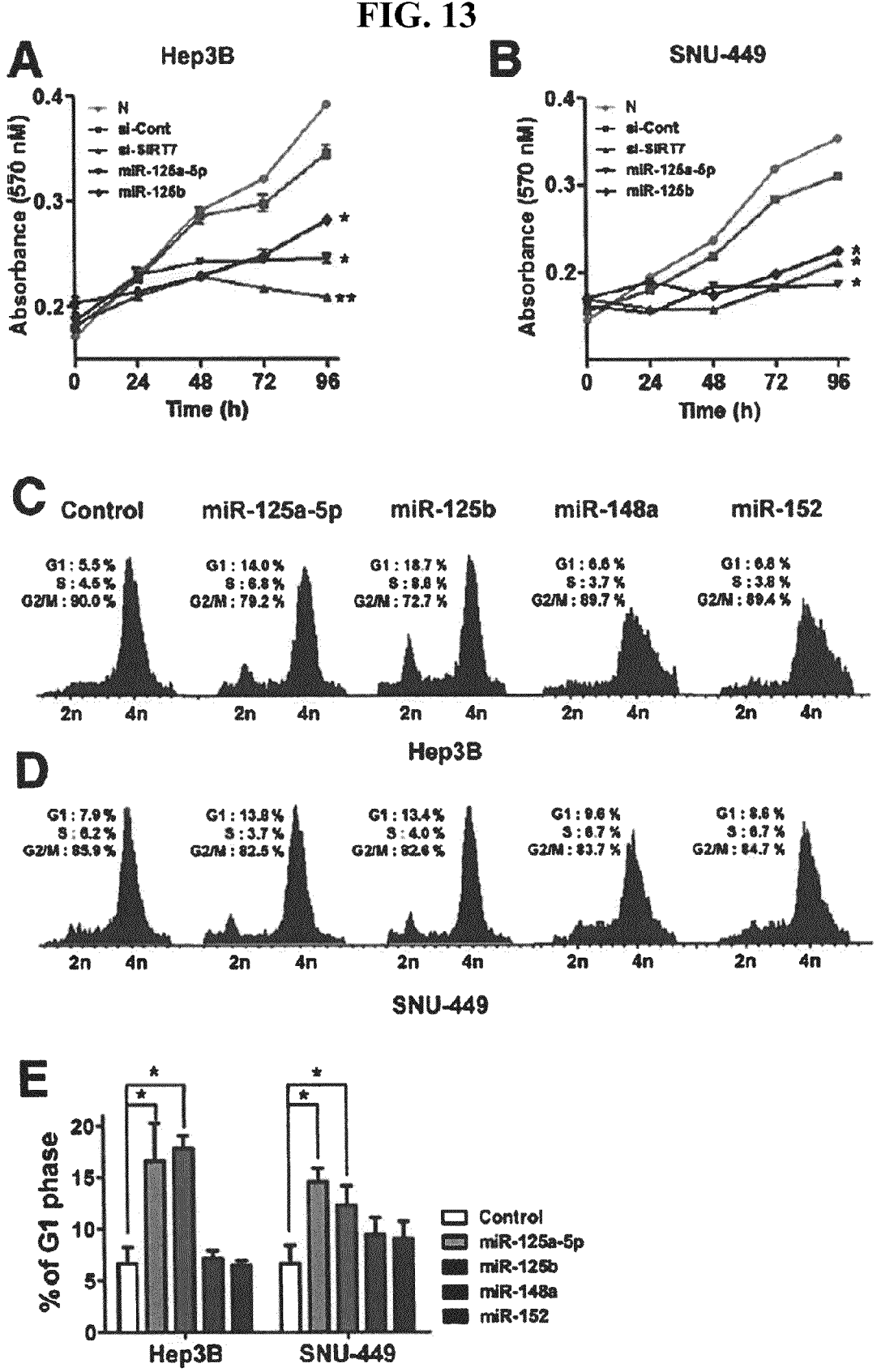
FIG. 13 shows experimental results indicating that miR-125a-5p and miR-125b are SIRT7 inhibitors and tumor suppressors in hepatocarcinogenesis.

It was shown by MTT analysis that the ectopic expression of miR-125a-5p and miR-125b significantly inhibited the growth of both Hep3B and SNU-449 cell lines (see FIGS. 13A and 13B). Further, the influence of the miRNAs on cell cycle distribution was evaluated, and as a result, it was shown that only miR-125a-5p and miR-125b induced G1 arrest, unlike corresponding control groups (scramble sequences of miRNA) or other miRNAs (miR-148a and miR-152) (see FIGS. 13C and 13D). Quantitative analysis of G1 phase indicated that cells expressing miR-125a-5p and miR-125b showed a significantly high ratio of G1 phase compared to cells that the control group or cells expressing miR-148a and miR-152 (see FIG. 13E).

In conclusion, these results demonstrate that miR-125a-5p and miR-125b are all director inhibitors of endogenous SIRT7 and can function as tumor suppressors in hepatocarcinogenesis.

Example II-5

Inactivation Mechanism of Tumor Suppressors, miR-125a-5p and miR-125b in HCC

II-5-1. Influence on Transcriptional Process

Whether epigenetic silencing in hepatocarcinogenesis and/or p53 activity influences the transcriptional expression of miR-125a-5p and miR-125b was examined. Liver cancer cells were treated with the DNA methylation inhibitor 5-aza-dC (5-aza-2-deoxycytidine) or the histone deacetylation inhibitor TSA (Trichostatin A) in order to observe whether DNA methylation or histone modification restore the endogenous expression of miR-125a-5p and miR-125b.

Figure 14:
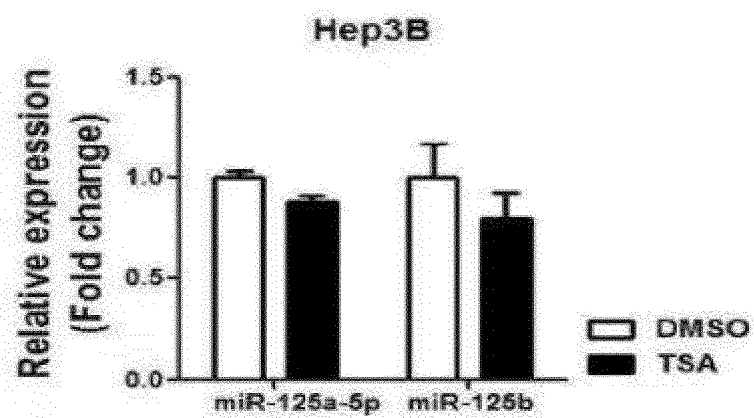
FIG. 14 shows the influence of a histone deacetylase inhibitor (TSA, trichostatin) on miR-125a-5p and miR-125b in HCC(14A-Hep3B, 14B-SNU-449).
Figure 14:
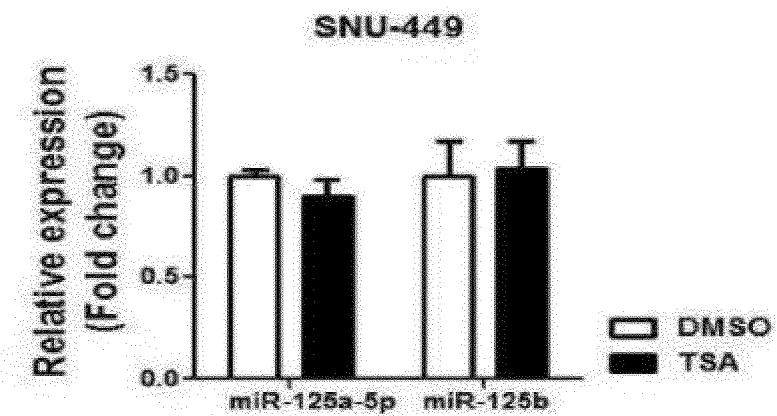

As a result, treatment of Hep3B and SNU-449 cells with 5-aza-dC selectively restored the expression of miRNA-125b in the two cell lines (see FIGS. 14A and 14B), whereas treatment of the cells with TSA had no influence on the expression of miR-125a-5p and miR-125b (see FIG. 14).

Further, in order to examine whether 5-aza-dC selectively inhibits miR-125b, promoter methylation sites in the cells were examined.

Figure 15:
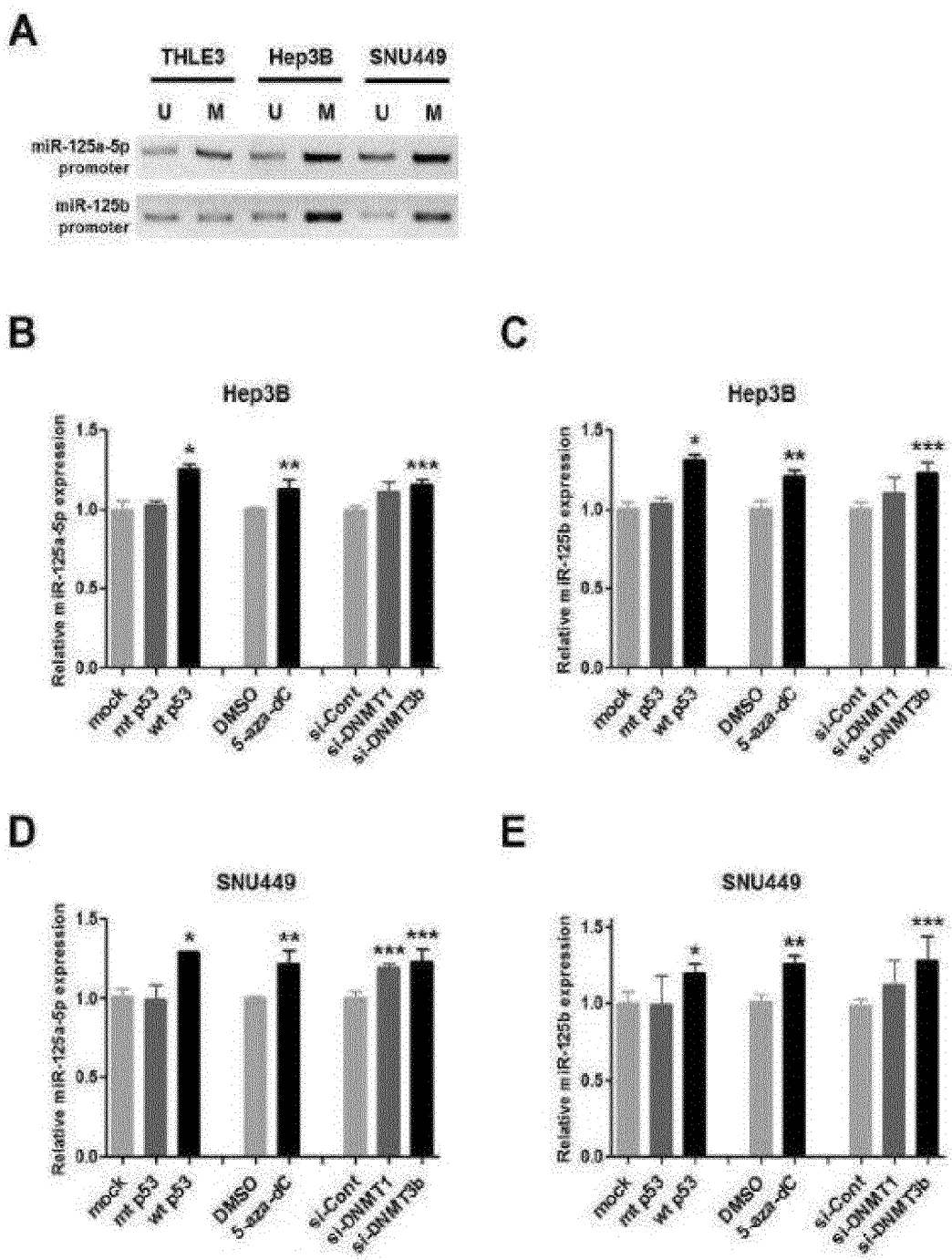
FIG. 15 shows experimental results on the inhibitory mechanism of miR-125a-5p and miR-125b in hepatocarcinogenesis.

As a result, it was observed that the normal liver cell line (THLE-3) and the HCC cell lines (Hep3B and SNU-449) showed hypermethylation in the promoter region of miR-125a-5p, whereas miR-125b was not methylated in THLE-3 and was highly methylated only in HCC cells (see FIG. 15A).

In addition, the use of a wild-type p53-expressing plasmid (pCMV-Neo-Bam-p53-wt) restored p53 activity in HCC cells. This is because Hep3B cells expresses p53-null and SNU-449 cells express only mutant p53.

Figure 16:
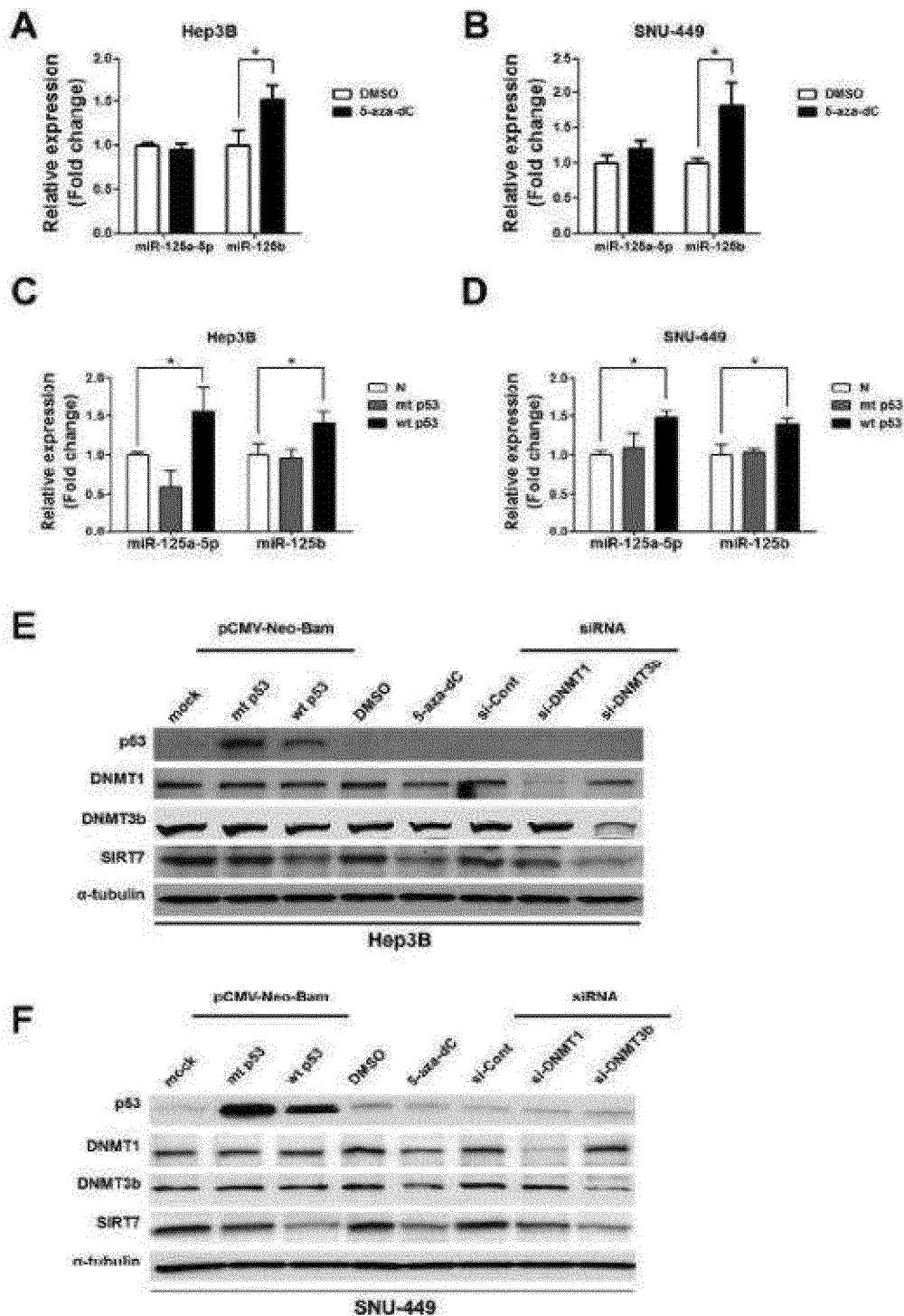
FIG. 16 shows experimental results on the inactivation mechanism of the tumor inhibitors miR-125a-5p and miR-125b in hepatocarcinogenesis.

As a result, it was shown that the endogenous expression of miR-125a-5p and miR-125b in Hep3B and SNU-449 cells was significantly increased by the ectopic expression of wild-type p53. The ectopic expression of wild-type p53 reduced the inhibition of SIRT7, whereas the expression of mutant-type p53 did not influence the expression level of SIRT7 (measured by Western blot analysis) in Hep3B and SNU-449 cells (see FIGS. 16E and 16F). Also, the inhibition of SIRT7 was observed in the cells treated with 5-aza-dC, and it was found that the targeted disruption of DNMT1 and DNMT3 induced the inhibition of SIRT7 expression in Hep3B and SNU-449 cells (see FIGS. 16E and 16F).

Additionally, the results of qRT-PCR showed that the endogenous expression of miR-125a-5p and miR-125b in Hep3B and SNU-449 cells was induced by ectopic p53 expression, 5-aza-dC treatment and the knockdown of DNMT1 and DNMT3b (see FIGS. 15B to 15E).

Such results show the mechanism of the endogenous inhibition of promoter methylation and/or p53 activity in HCC.

II-5-1 Clinical Assessment

To demonstrate the clinical significance of this fining of the present invention, human HCC tissues were analyzed.

First, the expression of SIRT7 protein in different subsets of human HCCs was examined. It was observed that SIRT7 was significantly highly expressed in all the HCCs compared to the adjacent non-tumor tissue (see FIG. 17A).

In addition, the endogenous expression of miR-125a-5p and miR-125b in human HCCs was analyzed by qRT-PCR. As a result, as shown in FIGS. 17B and 17C, the endogenous expression of miR-125a-5p and miR-125b significantly inhibited.

Such HCC samples were examined for p53 mutation using SSCP (single-stranded conformational polymorphism) and direct sequencing.

Figure 17:
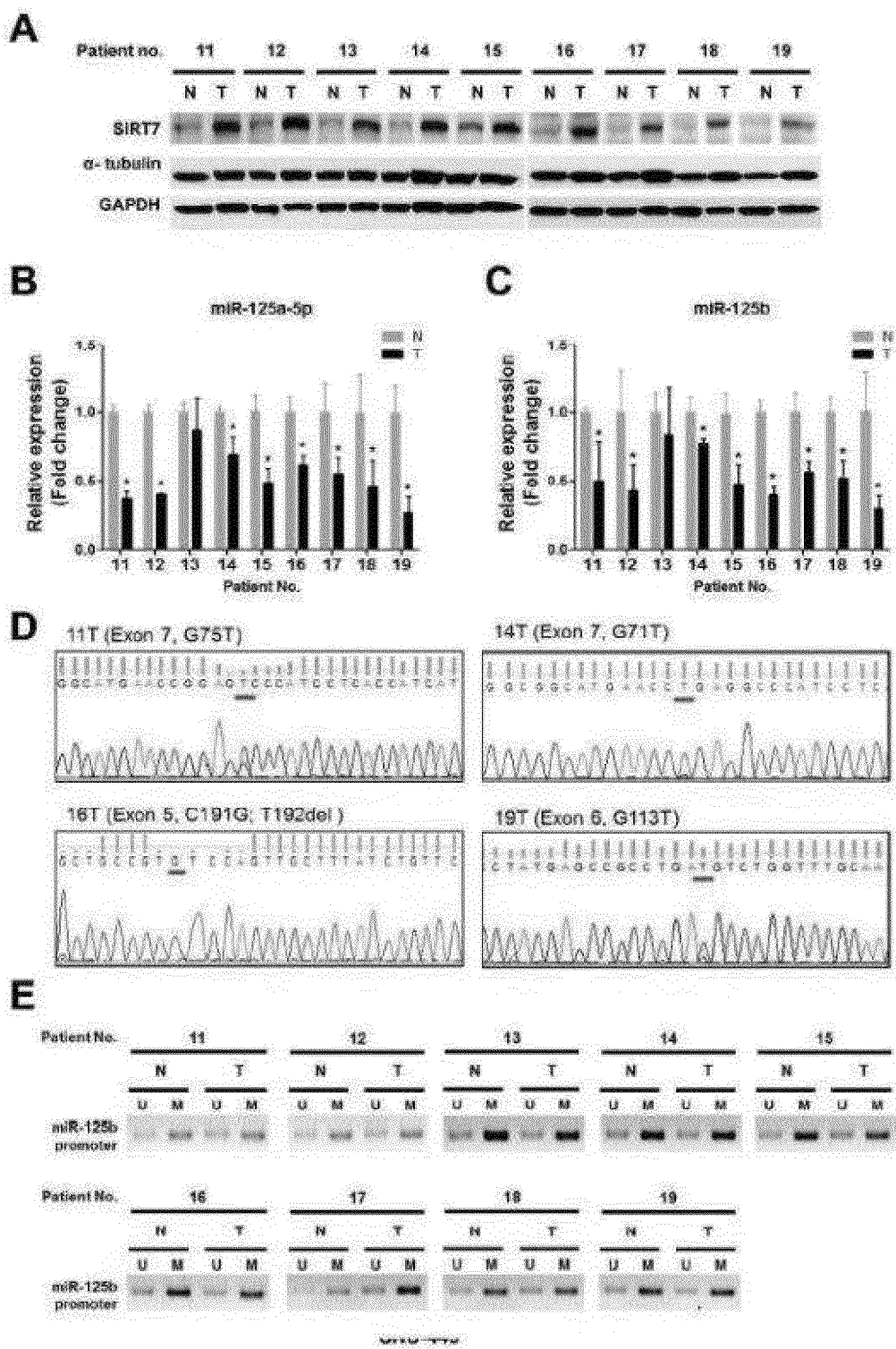
FIG. 17 shows in vivo evaluation results for a mechanism for the endogenous regulation of miR-125a-5p and miR-125b in hepatocarcinogenesis.

As shown in FIG. 17D, when the DNA-binding motif (i.e., exons 5 to 8) of p53 gene was analyzed, and as a result, four patients (patient numbers 11 14, 16 and 19) among nine patients showed a mutation in the exons (see FIG. 17D).

Finally, the sample tissue samples were examined for promoter methylation of miR-125b, and as a result, it was shown that, in the case of patient No. 17, the promoter region of miR-125b was very highly methylated compared to that in non-tumor tissue (see FIG. 17E). Based on the methylation-specific PCR analysis, it was found that hypermethylation is not the common mechanism of the inhibition of miR-125b. In addition, patient Nos. 12, 15 and 18 did not show mutation in p53 gene or showed methylation in the promoter region of miR-125b.

Nevertheless, 4HCC had a mutation in the DNA binding domain of p53 gene, and 1 HCC showed hypermethylation in the promoter region of miR-125b.

TABLE 2

| Patient No. | Expression | | p53 position | | Promoter methylation miR-125b |
|---|---|---|---|---|---|
| | SIRT7 | miR-125a-5p | Mutation | LOH | |
| 11 | Up | Down | Down | exon7 G75T | No | N/C |
| 12 | Up | Down | Down | No | No | N/C |
| 13 | Up | Down | Down | No | No | N/C |
| 14 | Up | Down | Down | No | No | N/C |
| 15 | Up | Down | Down | No | No | N/C |
| 16 | Up | Down | Down | No | No | N/C |
| 17 | Up | Down | Down | No | No | N/C |
| 18 | Up | Down | Down | No | No | Up |
| 19 | Up | Down | Down | No | No | N/C |
| 20 | Up | Down | Down | No | No | N/C |

LOH: Loss of Heterozygosity

Thus, a possible mechanism for the endogenous regulation of miR-125a-5p and miR-125b in hepatocarcinogenesis could be seen.

INDUSTRIAL APPLICABILITY

The expression level of SIRT7 according to the present invention is higher in cancer tissue or cancer cells than in non-liver cancer tissue or non-liver cancer cells. Thus, when a substance for measuring the level of SIRT7 is used as a cancer diagnostic marker, cancer can be easily diagnosed and predicted in a rapid and accurate manner. This substance can be used as a target for development of an agent for preventing or treating cancer.

In addition, miR-125a-5p or miR-125b according to the present invention can regulate the expression of SIRT7, which is overexpressed in cancer cells, to arrest cells at G1/S phase. Thus, it can influence the cell cycle to inhibit the growth of tumor cells. Accordingly, miR-125a-5p or miR-125b, which is an miRNA that regulates the expression of SIRT7, can be used as a target for treating cancer cells and can be used for development of a cancer therapeutic agent.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for treating cancer of a patient by administration to the patient of a composition comprising, as an active ingredient, siRNA (small interference RNA) oligonucleotide having a sequence complementary to a nucleotide sequence of the SIRT7 (sirtuin 7) gene, wherein the siRNA oligonucleotide has a nucleotide sequence set forth in SEQ ID NO: 3 or 4.

2. The method of claim 1, wherein the cancer is at least one cancer selected from the group consisting of hepatocellular carcinoma (HCC), biliary duct cancer, and metastatic liver cancer.

3. The method of claim 1, wherein the administration to the patient comprises oral, transdermal, subcutaneous, intravenous or intramuscular administration.

* * * * *

UNITED STATES PATENT AND TRADEMARK OFFICE
CERTIFICATE OF CORRECTION

Page 1 of 2

PATENT NO. : 9,274,117 B2
APPLICATION NO. : 14/138035
DATED : March 1, 2016
INVENTOR(S) : Suk-Woo Nam et al.

It is certified that error appears in the above-identified patent and that said Letters Patent is hereby corrected as shown below:

Specification

Column 2, line 49: "miR-125-5p" should be --miR-125a-5p--.

Column 3, line 14: "SI1RT7" should be --SIRT7--.

Column 3, line 45: "I11" should be --III--.

Column 7, line 12: "sufficiency" should be --sufficiently--.

Column 8, line 9: "as well a" should be --as well as--.

Column 8, line 14: "as" should be --a--.

Column 12, line 3: "(HIMC)" should be --(HMC)--.

Column 12, line 41: "mRNiA" should be --mRNA--.

Column 17, line 15: "historic" should be --histone--.

Column 17, line 29: "methyation" should be --methylation--.

Column 19, line 43: "eukaryolic" should be --eukaryotic--.

Column 19, line 53: "SIR17" should be --SIRT7--.

Column 20, line 35: "SIR17" should be --SIRT7--.

Column 22, line 33: "cheeked" should be --checked--.

Column 23, line 6: "PVDP" should be --PVDF--.

Column 23, line 21: "fractional ion" should be --fractionation--.

Signed and Sealed this
Nineteenth Day of July, 2016

Michelle K. Lee
*Director of the United States Patent and Trademark Office*

CERTIFICATE OF CORRECTION (continued)
U.S. Pat. No. 9,274,117 B2

Specification

Column 24, line 20: "Rule" should be --Role--.

Column 25, line 25: "Hce3B" should be --Hep3B--.

Column 25, line 34: "analysed" should be --analyzed--.

Column 25, line 44: "acelylated" should be --acetylated--.

Column 26, line 21: "rumor" should be --tumor--.

Column 26, line 63: "pMF18S-HDAC2" should be --pME18S-HDAC2--.

Column 29, line 48: "Amnion's" should be --Ambion's--.

Column 30, line 37: "MIT" should be --MTT--.

Column 30, line 54: "PVDf" should be --PVDF--.

Column 30, line 60: "tubolin" should be --tubulin--.

Column 30, line 60: "tubolin" should be --tubulin--.

Column 31, line 7: "acelylated" should be --acetylated--.

Column 32, line 15-16: "http://cent.hsc.use.edu/cpgislands2/epg.aspx" should be --http://ccnt.hsc.usc.edu/cpgislands2/cpg.aspx--.

Column 32, line 55: "patterns" should be --patients--.

Column 32, line 56: "SIRT7expression" should be --SIRT7 expression--.

Column 32, line 59: "SIRT7knockdown" should be --SIRT7 knockdown--.

Column 34, line 30: "acetylaled" should be --acetylated--.

Column 34, line 31: "inaciivation" should be --inactivation--.

Column 34, line 57: "(sec FIG. 10B)" should be --(see FIG. 10B)--.

Column 35, line 10: "psiCHECH2-SIRT7_3-UTR" should be --psiCHECK2-SIRT7_3-UTR--.

SEQUENCE LISTING

<160> NUMBER OF SEQ ID NOS: 52

<210> SEQ ID NO 1
<211> LENGTH: 6244
<212> TYPE: DNA
<213> ORGANISM: Artificial Sequence
<220> FEATURE:
<223> OTHER INFORMATION: Mammalian SIRT7 gene

<400> SEQUENCE: 1

```
cgcggcctgc cgtgtgaggc ggaagcggaa gagcaggtct ccaggggagc gatggcagcc      60
gggggtctga gccgctccga gcgcaaagcg gcggagcggg tccggaggtt gcgggaggag     120
cagcagaggg agcgcctccg ccaggtacgc cgccgccgct ccccggcccg gccatgcccg     180
gcccgcgccg ccgctcaccg tccgcctgcc cgcaggtgtc gcgcatcctg aggaaggcgg     240
cggcggagcg cagcgccgag gagggccggc tgctggccga gagcgcggac ctggtaacgg     300
agctgcaggg ccggagccgg cggcgcgagg gcctgaagcg gcggcaggag gaggcgagtt     360
ccgcgtgcgg cgcgcgggcg ccccggttt  cgggagcagc tgggcgacg ggcggtcccg     420 ggtggggcgg cccggggcgg tgaccaccct ggcgtcttgg caggtgtgcg acgacccgga     480
ggagctgcgg gggaaggtcc gggagctggc cagcgccgtc cggaacgcca aatacttggt     540
cgtctacaca ggcgcgggaa tcagcacggt agggagggag gcggaggcgt accccaggac     600
```

```
ggagtatgag ctccagtaat cgcgaaaaac tcgcctttaa agcagctcta aggttttttc      660
tcttaaagaa acgaaatgac caaaacttac ctaaggtaaa cgcttttttaa acgcttggcc      720 tctgtgttac agccagttaa aaaaaacaag gagtagagat acgaatgggg tgtagtagcc      780
gactgctcgc aggcaccccc aggttatgtg gacagagcta agcccaaagt tgtgattttc      840
cactctgttc tgtccatgtc gagggaagat aagtagaaag tgacacagta agagccagaa      900
tacaccaggt gaaggagaga attgcattgt gttttgagaa gtttcactga caagttatcc      960
tgggctgtgg gacatcacta gctttgaaag tgtagctggc acctcgtcca tctaatttga     1020
tgggtgtgtg tggggtgttg ggcacgcgtc ggcctagcag atctgaaccc aggtgatttc     1080
tgttctcagg aagcttttag gtgacaagga tcaggcatgt gaacaaataa ccatactgta     1140
aagctggctg tgctgggtcg ctagagcaaa ctcagacaca cactctgcgc tcttggagtt     1200
gggaaaccca cctgcgttgg cttttgtgg gaggtggcct tgattgggcc ttgaaggatg     1260
ggtgagattt acagaaggtt ggaatgaggc actccaagca agaacagca gaggctcagc     1320 agcaagaatg caaaaaggga gttcactact gactcaaata cccggagccc tggggtttag     1380
tctcctccct ccacaagtca catgtaaaag tccagtcatg ctgggcgcgg tggctcatgc     1440
ctataatcct agcactttgg gaggccgagg tgggcggatc atgaggtcag tagttcaaga     1500
acaacctggc caaacggtg aaaccctgtc tctactaaaa atacaaaaat tagtcgggca     1560
tggtggtggg cacctgcaat cccagctact cgagaggctg aggcaggaga atcacttgaa     1620
actggaaggc ggaggttgca gtgagccgag atcatgccac tgcattccag cctgggcgaa     1680
agagctaaac tccgtctctc aaaaaaaaaa aaaaaaaaa aagtccagtc atgtaattat     1740
gtaacagtca cgtgacctgt tatggaactt ccaatggcaa ctaaaagcac atgcagctag     1800
tggatttcat cggagtgttt gaggttcccg tcttgaatgt gactgtcgga actactgtcc     1860 ggggggggtgg tgcattttc tgagtttaag caggagtcgg gagtccccaa aagggaacac     1920
aagacacctt gatcctggca tatcttgtgt gccctctgtg ggcctcagtt tgtttcacag     1980
gattgaaaac ctgggaagtt agatgctcat ctcatctgaa gaagttgttc tgcctttgtt     2040
aaggtggagc gggaatagtc agcactggga catgagaatg gacagtcgcc tggacccacc     2100
tagggattca ccatttgcta aatgtgtgag ctgtgggctc ggccctgggg cactttagg     2160 aacatgacta gtcttcccct gcagtgtgga ggacacatgt gccacagagc ccagctttgt     2220
gctcggtgcc agagaggctt ccggaggcag gcagggctgc gtgcagcctg aaggatgag     2280 ccaggccagg cgggaaacgg aagtccaggt agaaggggagg agccgaattg gggtacactc     2340
catatgggct caggcaggtc agcctgtgga atgaatagag gccaacatgc aggccagccc     2400
ggaatgcggc aggagtgaca gtggcttcc gtttctggga attctgccag tacctacagt     2460
ggtgcctttt gacttggctt acctttttttc tcgacatgca ggcagcgtct atcccagact     2520
accggggccc taatgagtg tggacactgc ttcagaaagg gagaagcgtt aggtaagcgg     2580
gccaggcatg gcctcccaca taggctgggc agcggcagca cgggcctgag ctccagctct     2640
cctcaccttg ccttcctttc tgcctggcag tgctgccgac ctgagcgagg ccgagccaac     2700
cctcacccac atgagcatca cccgtctgca tgagcagaag ctggtaagag ccctgggtgg     2760
ctggtacact tgccagggac caggcagagc accttggtgc ccagtgggca actaactgca     2820
cccgccctct gtctgccagt tgactccat gatgagcacc caccaagcgg ttaggccgc     2880 gggtttgatc ctcctgtgct tgactctcca ggacagaagg ggagctcccc ctctgaacca     2940
tcccatccgc agccagcctc agcctcagag ctgctggtgg cctttcccct ttgtgattcc     3000
```

```
cttgcatttt tctgtggacc tcagaagcca tcctagtcac aggggaggct tataggacat   3060
ctctggggac cttctgctga acaccctcaa ccaatggggt gtagtggttg atctgcctag   3120
gtccccaggg acctgaaatg tcatgaccca agagagcatg gatctggggc agagtggccc   3180
ttgccaaacc ccgagccact tcccaacctt gccgggacgg tgcaacctct tgccctccca   3240
gccactccag gtgcatcagg gctggaggaa ggacagcccc tccccaccac aggccctctt   3300
gactcctggt ggttggacct gttgtgtgtt ttactttcta aggctctctg ggggacgga   3360 gctgcccctg gttttgggag ccatcggcgg ggctcagaac agcctcgctg tggccgggta   3420
ctgacctccc caccaccact ggcagccatc cctcccttg ccacccgttc tgccttccag   3480
gtgcagcatg tggtgtctca gaactgtgac gggctccacc tgaggagtgg gctgccgcgc   3540
acggccatct ccgagctcca cgggaacatg tacattgaag tgagcagtcc tgcagggacc   3600
cagggtctcc atgggcaggc gggtcccact cactgtgccc tcttgcctct aggtctgtac   3660
ctcctgcgtt cccaacaggg agtacgtgcg ggtgttcgat gtgacggagc gcactgccct   3720
ccacagacac cagacaggcc ggacctgcca caagtgtggg acccagctgc gggacaccat   3780
tgtgcacttt ggggagaggg ggacgttggg gcagcctctg aactgggaag cggcgaccga   3840
ggctgccagc agagcagaca ccatcctgtg tctagggtcc agcctgaagg tacgtgccga   3900
tgacacaatg agtgaaccga gcccctgccc gcccgagggt gtccagctct gcggcccagc   3960
actgtacaga cttgtccctt gtgtgtgtgc ggtgtctgtc tgtctgcttc cacaggttct   4020
aaagaagtac ccacgcctct ggtgcatgac caagcccct agccggcggc cgaagcttta   4080
catcgtgaac ctgcaggtaa ctcgggtgct gagagccacg tccttagatc tgggtcttag   4140
aacgcacagc cagagacacc ccacacccat gcaccagggc ggtctgatag gccccgtg    4200 ggtgctcagg gagcaccgac tgagcccgta ggggccaagg ctgacaggcc accgggaagg   4260
gttgggctgc tgttactctc actcggcttt ccctgtcctc agtggacccc gaaggatgac   4320
tgggctgccc tgaagctaca tgggaagtgt gatgacgtca tgcggctcct catggccgag   4380
ctgggcttgg agatccccgc ctatagcagg tgagtgagcc gctgcagcag cctgcttccc   4440
cgcacctctg tgtgctgggc cttgtctgtc ttctctcgtg agctgagtgt ggaggaagct   4500
ctgaggtgtt tgcagtggtg cctgaggcat gactgaagcg tggtggtctc cagagggcct   4560
gacctcggtg gttggcggag accctgcgtg tgccactcct gccctggctg atgtggcaca   4620
cacaatcccc gcggggagag ggattctgcc cgcgtgctcc tgctccaggc ctccccgtgg   4680
agctctccga gatgcctggt gggaagcatc tggaggggac gagcactcgg cagctctggt   4740
cagacagaat ctgtgtgctt ggttttggga gttggcgtac tttgggaaag cttaaacaaa   4800
ctgtgcctta atacagaatt tgtgataatt tagacttggt gtatgtattg agtaaaaagt   4860
ttacactctc tttctctgtg aattttcagg gtcttatagg ggaaatcaat aacttctttt   4920
aatcaaaggt ttcaagaaat taaggatccc ttcaccttct gggcctggca cttcttgtat   4980
gttatgtgtg tggtgttctg tgatgtgggc tatcgtgtac tgtatttttt ttttacatta   5040
acttagctca ttttccttat cagtgcgtat ctgtatctta agttatgatc tgtggttctg   5100
catctccgtc agacacatgc tttcttcacg gggtcgtctg taggccacgc ctccctagtc   5160
agctgggaag ggggagaggg tctggtccac ctgccccagc ggtacaagtg aaggtgggg    5220 cccagagttg ctagtgactc atccctggag acggaggcag ccctgggggcc actgctgccc   5280 caccctgtgt gtgcacgccg ctcagtggtg gacaaggaca cggagttttg aggagaccga   5340
```

```
gctagtgtgg gtgccgacct ttgagtcacc acctaagagg tgacctctcc cacatccgtt    5400
ctgcagcttg gtaacaatga agctgccgcc aaccagagcc ccgccgcagt tgacacggga    5460 gggaaggga tgggaaggca gggaccgcag acagctttcc cgagctgggg caggtgtgac     5520
tgcgagaggc tcccaggccc gcctgatgcc gctttcccct tttggcaggt ggcaggatcc    5580
cattttctca ctggcgactc ccctgcgtgc tggtgaagaa ggcagccaca gtcggaagtc    5640
gctgtgcaga agcagagagg aggccccgcc tggggaccgg ggtgcaccgc ttagctcggc    5700
ccccatccta gggggctggt ttggcagggg ctgcacaaaa cgcacaaaaa ggaagaaagt    5760
gacgtaatca cgtgctcgat gaagaacagt tggcactttg cagatggcca gtgtcacggt    5820
gaaggctggg ttgcccccac gggtctaggg agaacgaact ctttggggat gacattttca    5880
ccgtgacatt tttagccatt tgtccttgag gaagccccct gcactgctgc ggttgtaccc    5940
tgatacggcc tggccatcga ggacacctgc ccatccggcc tctgtgtcaa gaggtggcag    6000
ccgcaccttt ctgtgagaac ggaactcggg ttatttcagc cccggcctgc agagtggaag    6060
cgcccagcgg cctttcctcg ctcaccaggc cagtctcagg gcctcaccgt atttctacta    6120
ctacttaatg aaaaagtgtg aactttatag aatcctctct gtactggatg tgcggcagag    6180
gggtggctcc gagcctcggc tctatgcaga ccttttatt tctattaaac gtttctgcac     6240
tggc                                                                6244
```

<210> SEQ ID NO 2
<211> LENGTH: 400
<212> TYPE: PRT
<213> ORGANISM: Artificial Sequence
<220> FEATURE:
<223> OTHER INFORMATION: Mammalian SIRT7 protein

<400> SEQUENCE: 2

```
Met Ala Ala Gly Gly Leu Ser Arg Ser Glu Arg Lys Ala Ala Glu Arg
1               5                   10                  15

Val Arg Arg Leu Arg Glu Glu Gln Arg Glu Arg Leu Arg Gln Val
            20                  25                  30

Ser Arg Ile Leu Arg Lys Ala Ala Ala Glu Arg Ser Ala Glu Glu Gly
        35                  40                  45

Arg Leu Leu Ala Glu Ser Ala Asp Leu Val Thr Glu Leu Gln Gly Arg
    50                  55                  60

Ser Arg Arg Arg Glu Gly Leu Lys Arg Arg Gln Glu Glu Val Cys Asp
65                  70                  75                  80

Asp Pro Glu Glu Leu Arg Gly Lys Val Arg Glu Leu Ala Ser Ala Val
                85                  90                  95

Arg Asn Ala Lys Tyr Leu Val Val Tyr Thr Gly Ala Gly Ile Ser Thr
            100                 105                 110

Ala Ala Ser Ile Pro Asp Tyr Arg Gly Pro Asn Gly Val Trp Thr Leu
        115                 120                 125

Leu Gln Lys Gly Arg Ser Val Ser Ala Ala Asp Leu Ser Glu Ala Glu
    130                 135                 140

Pro Thr Leu Thr His Met Ser Ile Thr Arg Leu His Glu Gln Lys Leu
145                 150                 155                 160

Val Gln His Val Val Ser Gln Asn Cys Asp Gly Leu His Leu Arg Ser
                165                 170                 175

Gly Leu Pro Arg Thr Ala Ile Ser Glu Leu His Gly Asn Met Tyr Ile
            180                 185                 190

Glu Val Cys Thr Ser Cys Val Pro Asn Arg Glu Tyr Val Arg Val Phe
```

-continued

```
                195                 200                 205
Asp Val Thr Glu Arg Thr Ala Leu His Arg His Gln Thr Gly Arg Thr
210                 215                 220

Cys His Lys Cys Gly Thr Gln Leu Arg Asp Thr Ile Val His Phe Gly
225                 230                 235                 240

Glu Arg Gly Thr Leu Gly Gln Pro Leu Asn Trp Glu Ala Ala Thr Glu
                245                 250                 255

Ala Ala Ser Arg Ala Asp Thr Ile Leu Cys Leu Gly Ser Ser Leu Lys
            260                 265                 270

Val Leu Lys Lys Tyr Pro Arg Leu Trp Cys Met Thr Lys Pro Pro Ser
275                 280                 285

Arg Arg Pro Lys Leu Tyr Ile Val Asn Leu Gln Trp Thr Pro Lys Asp
290                 295                 300

Asp Trp Ala Ala Leu Lys Leu His Gly Lys Cys Asp Asp Val Met Arg
305                 310                 315                 320

Leu Leu Met Ala Glu Leu Gly Leu Glu Ile Pro Ala Tyr Ser Arg Trp
                325                 330                 335

Gln Asp Pro Ile Phe Ser Leu Ala Thr Pro Leu Arg Ala Gly Glu Glu
            340                 345                 350

Gly Ser His Ser Arg Lys Ser Leu Cys Arg Ser Arg Glu Glu Ala Pro
        355                 360                 365

Pro Gly Asp Arg Gly Ala Pro Leu Ser Ser Ala Pro Ile Leu Gly Gly
370                 375                 380

Trp Phe Gly Arg Gly Cys Thr Lys Arg Thr Lys Arg Lys Val Thr
385                 390                 395                 400

<210> SEQ ID NO 3
<211> LENGTH: 21
<212> TYPE: RNA
<213> ORGANISM: Artificial Sequence
<220> FEATURE:
<223> OTHER INFORMATION: si-SIRT7-sense

<400> SEQUENCE: 3
ucaauguaca uguucccgug g                                               21

<210> SEQ ID NO 4
<211> LENGTH: 21
<212> TYPE: RNA
<213> ORGANISM: Artificial Sequence
<220> FEATURE:
<223> OTHER INFORMATION: si-SIRT7-anti sense

<400> SEQUENCE: 4
ucaauguaca uguucccgug g                                               21

<210> SEQ ID NO 5
<211> LENGTH: 21
<212> TYPE: DNA
<213> ORGANISM: Artificial Sequence
<220> FEATURE:
<223> OTHER INFORMATION: si-Cont-sense

<400> SEQUENCE: 5
ccuacgccac caauuucgut t                                               21

<210> SEQ ID NO 6
<211> LENGTH: 21
<212> TYPE: DNA
<213> ORGANISM: Artificial Sequence
```

```
<220> FEATURE:
<223> OTHER INFORMATION: si-Cont-anti sense

<400> SEQUENCE: 6
acgaaauugg uggcguaggt t                                              21

<210> SEQ ID NO 7
<211> LENGTH: 24
<212> TYPE: RNA
<213> ORGANISM: Artificial Sequence
<220> FEATURE:
<223> OTHER INFORMATION: MiR-125a-5p

<400> SEQUENCE: 7
ucccugagac ccuuuaaccu guga                                           24

<210> SEQ ID NO 8
<211> LENGTH: 22
<212> TYPE: RNA
<213> ORGANISM: Artificial Sequence
<220> FEATURE:
<223> OTHER INFORMATION: MiR-125b

<400> SEQUENCE: 8
ucccugagac ccuaacuugu ga                                             22

<210> SEQ ID NO 9
<211> LENGTH: 34
<212> TYPE: DNA
<213> ORGANISM: Artificial Sequence
<220> FEATURE:
<223> OTHER INFORMATION: SIRT7-3UTR-F

<400> SEQUENCE: 9
ccgctcgagc ggtcacgtgc tcgatgaaga acag                                34

<210> SEQ ID NO 10
<211> LENGTH: 39
<212> TYPE: DNA
<213> ORGANISM: Artificial Sequence
<220> FEATURE:
<223> OTHER INFORMATION: SIRT7-3UTR-R

<400> SEQUENCE: 10
atttgcggcc gctttagcca gtgcagaaac gtttaatag                           39

<210> SEQ ID NO 11
<211> LENGTH: 37
<212> TYPE: DNA
<213> ORGANISM: Artificial Sequence
<220> FEATURE:
<223> OTHER INFORMATION: SIRT7-3UTR-125 mt-F

<400> SEQUENCE: 11
cgctcaccag gccagtgagt gcgcctcacc gtatttc                             37

<210> SEQ ID NO 12
<211> LENGTH: 36
<212> TYPE: DNA
<213> ORGANISM: Artificial Sequence
<220> FEATURE:
<223> OTHER INFORMATION: SIRT7-3UTR-125 mt-R

<400> SEQUENCE: 12
aaatacggtg aggcgcactc actggcctgg tgagcg                              36
```

```
<210> SEQ ID NO 13
<211> LENGTH: 37
<212> TYPE: DNA
<213> ORGANISM: Artificial Sequence
<220> FEATURE:
<223> OTHER INFORMATION: SIRT7-3UTR-148 mt-F

<400> SEQUENCE: 13
ccttgaggaa gccccttcgt gtgctgcggt tgtaccc                                37

<210> SEQ ID NO 14
<211> LENGTH: 37
<212> TYPE: DNA
<213> ORGANISM: Artificial Sequence
<220> FEATURE:
<223> OTHER INFORMATION: SIRT7-3UTR-148 mt-R

<400> SEQUENCE: 14
gggtacaacc gcagcacacg aaggggcttc ctcaagg                                37

<210> SEQ ID NO 15
<211> LENGTH: 39
<212> TYPE: DNA
<213> ORGANISM: Artificial Sequence
<220> FEATURE:
<223> OTHER INFORMATION: SIRT7-3UTR-193 mt-F

<400> SEQUENCE: 15
cctttcctcg ctcaccagcg gtgtctcagg gcctcaccg                              39

<210> SEQ ID NO 16
<211> LENGTH: 38
<212> TYPE: DNA
<213> ORGANISM: Artificial Sequence
<220> FEATURE:
<223> OTHER INFORMATION: SIRT7-3UTR-193 mt-R

<400> SEQUENCE: 16
ggtgaggccc tgagacaccg ctggtgagcg aggaaagg                               38

<210> SEQ ID NO 17
<211> LENGTH: 23
<212> TYPE: RNA
<213> ORGANISM: Artificial Sequence
<220> FEATURE:
<223> OTHER INFORMATION: hsa-miR-125a-5p

<400> SEQUENCE: 17
uccugagacc cuuuaaccug uga                                               23

<210> SEQ ID NO 18
<211> LENGTH: 22
<212> TYPE: RNA
<213> ORGANISM: Artificial Sequence
<220> FEATURE:
<223> OTHER INFORMATION: hsa-miR-125b

<400> SEQUENCE: 18
ucccugagac ccuaacuugu ga                                                22

<210> SEQ ID NO 19
<211> LENGTH: 22
<212> TYPE: RNA
<213> ORGANISM: Artificial Sequence
<220> FEATURE:
<223> OTHER INFORMATION: hsa-miR-148a
```

<400> SEQUENCE: 19
ucagugcacu acagaacuuu gu                                            22

<210> SEQ ID NO 20
<211> LENGTH: 21
<212> TYPE: RNA
<213> ORGANISM: Artificial Sequence
<220> FEATURE:
<223> OTHER INFORMATION: hsa-miR-152

<400> SEQUENCE: 20
ucagugcaug acagaacuug g                                             21

<210> SEQ ID NO 21
<211> LENGTH: 22
<212> TYPE: RNA
<213> ORGANISM: Artificial Sequence
<220> FEATURE:
<223> OTHER INFORMATION: hsa-miR-193a-3p

<400> SEQUENCE: 21
aacuggccua caaaguccca gu                                            22

<210> SEQ ID NO 22
<211> LENGTH: 54
<212> TYPE: DNA
<213> ORGANISM: Artificial Sequence
<220> FEATURE:
<223> OTHER INFORMATION: U6 snRNA-RT

<400> SEQUENCE: 22
gtcgtatcca gtgcagggtc cgaggtattc gcactggata cgacaaaaat atgg          54

<210> SEQ ID NO 23
<211> LENGTH: 50
<212> TYPE: DNA
<213> ORGANISM: Artificial Sequence
<220> FEATURE:
<223> OTHER INFORMATION: hsa-miR-125a-5p-RT

<400> SEQUENCE: 23
gtcgtatcca gtgcagggtc cgaggtattc gcactggata cgactcacag               50

<210> SEQ ID NO 24
<211> LENGTH: 50
<212> TYPE: DNA
<213> ORGANISM: Artificial Sequence
<220> FEATURE:
<223> OTHER INFORMATION: hsa-miR-125b-RT

<400> SEQUENCE: 24
gtcgtatcca gtgcagggtc cgaggtattc gcactggata cgactcacaa               50

<210> SEQ ID NO 25
<211> LENGTH: 50
<212> TYPE: DNA
<213> ORGANISM: Artificial Sequence
<220> FEATURE:
<223> OTHER INFORMATION: hsa-miR-148a-RT

<400> SEQUENCE: 25
gtcgtatcca gtgcagggtc cgaggtattc gcactggata cgacacaaag               50

<210> SEQ ID NO 26

```
<211> LENGTH: 50
<212> TYPE: DNA
<213> ORGANISM: Artificial Sequence
<220> FEATURE:
<223> OTHER INFORMATION: hsa-miR-152-RT

<400> SEQUENCE: 26
gtcgtatcca gtgcagggtc cgaggtattc gcactggata cgacccaagt          50

<210> SEQ ID NO 27
<211> LENGTH: 50
<212> TYPE: DNA
<213> ORGANISM: Artificial Sequence
<220> FEATURE:
<223> OTHER INFORMATION: hsa-miR-193a-3p-RT

<400> SEQUENCE: 27
gtcgtatcca gtgcagggtc cgaggtattc gcactggata cgacactggg          50

<210> SEQ ID NO 28
<211> LENGTH: 21
<212> TYPE: DNA
<213> ORGANISM: Artificial Sequence
<220> FEATURE:
<223> OTHER INFORMATION: U6 snRNA-F

<400> SEQUENCE: 28
ggctgccgaa ggatgacacg c                                         21

<210> SEQ ID NO 29
<211> LENGTH: 23
<212> TYPE: DNA
<213> ORGANISM: Artificial Sequence
<220> FEATURE:
<223> OTHER INFORMATION: hsa-miR-125a-5p-F

<400> SEQUENCE: 29
tcctgagacc ctttaacctg tga                                       23

<210> SEQ ID NO 30
<211> LENGTH: 22
<212> TYPE: DNA
<213> ORGANISM: Artificial Sequence
<220> FEATURE:
<223> OTHER INFORMATION: hsa-miR-125b-F

<400> SEQUENCE: 30
tccctgagac cctaacttgt ga                                        22

<210> SEQ ID NO 31
<211> LENGTH: 22
<212> TYPE: DNA
<213> ORGANISM: Artificial Sequence
<220> FEATURE:
<223> OTHER INFORMATION: hsa-miR-148a-F

<400> SEQUENCE: 31
tcagtgcact acagaacttt gt                                        22

<210> SEQ ID NO 32
<211> LENGTH: 21
<212> TYPE: DNA
<213> ORGANISM: Artificial Sequence
<220> FEATURE:
<223> OTHER INFORMATION: hsa-miR-152-F

<400> SEQUENCE: 32
```
tcagtgcatg acagaacttg g                                              21

<210> SEQ ID NO 33
<211> LENGTH: 22
<212> TYPE: DNA
<213> ORGANISM: Artificial Sequence
<220> FEATURE:
<223> OTHER INFORMATION: hsa-miR-193a-3p-F

<400> SEQUENCE: 33
aactggccta caaagtccca gt                                             22

<210> SEQ ID NO 34
<211> LENGTH: 16
<212> TYPE: DNA
<213> ORGANISM: Artificial Sequence
<220> FEATURE:
<223> OTHER INFORMATION: Universal-R

<400> SEQUENCE: 34
gtgcagggtc cgaggt                                                    16

<210> SEQ ID NO 35
<211> LENGTH: 25
<212> TYPE: DNA
<213> ORGANISM: Artificial Sequence
<220> FEATURE:
<223> OTHER INFORMATION: miR-125b-U-F

<400> SEQUENCE: 35
gggaaaatga gagtttttag tgtgt                                          25

<210> SEQ ID NO 36
<211> LENGTH: 25
<212> TYPE: DNA
<213> ORGANISM: Artificial Sequence
<220> FEATURE:
<223> OTHER INFORMATION: miR-125b-U-R

<400> SEQUENCE: 36
caatctcaaa atttaatata tcact                                          25

<210> SEQ ID NO 37
<211> LENGTH: 23
<212> TYPE: DNA
<213> ORGANISM: Artificial Sequence
<220> FEATURE:
<223> OTHER INFORMATION: miR-125b-M-F

<400> SEQUENCE: 37
gaaaatgaga gttttagtg cgt                                             23

<210> SEQ ID NO 38
<211> LENGTH: 25
<212> TYPE: DNA
<213> ORGANISM: Artificial Sequence
<220> FEATURE:
<223> OTHER INFORMATION: miR-125b-M-R

<400> SEQUENCE: 38
caatctcgaa atttaatata tcgct                                          25

<210> SEQ ID NO 39
<211> LENGTH: 20
<212> TYPE: DNA

```
<213> ORGANISM: Artificial Sequence
<220> FEATURE:
<223> OTHER INFORMATION: E5-F1

<400> SEQUENCE: 39
gctgccgtgt tccagttgct                                                     20

<210> SEQ ID NO 40
<211> LENGTH: 20
<212> TYPE: DNA
<213> ORGANISM: Artificial Sequence
<220> FEATURE:
<223> OTHER INFORMATION: E5-R1

<400> SEQUENCE: 40
ccagccctgt cgtctctcca                                                     20

<210> SEQ ID NO 41
<211> LENGTH: 20
<212> TYPE: DNA
<213> ORGANISM: Artificial Sequence
<220> FEATURE:
<223> OTHER INFORMATION: E6-F1

<400> SEQUENCE: 41
ggcctctgat tcctcagtga                                                     20

<210> SEQ ID NO 42
<211> LENGTH: 20
<212> TYPE: DNA
<213> ORGANISM: Artificial Sequence
<220> FEATURE:
<223> OTHER INFORMATION: E6-R1

<400> SEQUENCE: 42
gccactgaca accaccctta                                                     20

<210> SEQ ID NO 43
<211> LENGTH: 20
<212> TYPE: DNA
<213> ORGANISM: Artificial Sequence
<220> FEATURE:
<223> OTHER INFORMATION: E7-F1

<400> SEQUENCE: 43
tgccacaggt ctccccaagg                                                     20

<210> SEQ ID NO 44
<211> LENGTH: 20
<212> TYPE: DNA
<213> ORGANISM: Artificial Sequence
<220> FEATURE:
<223> OTHER INFORMATION: E7-R1

<400> SEQUENCE: 44
agtgtgcagg gtggcaagtg                                                     20

<210> SEQ ID NO 45
<211> LENGTH: 20
<212> TYPE: DNA
<213> ORGANISM: Artificial Sequence
<220> FEATURE:
<223> OTHER INFORMATION: E8-F1

<400> SEQUENCE: 45
ccttactgcc tcttgcttct                                                     20
```

<210> SEQ ID NO 46
<211> LENGTH: 20
<212> TYPE: DNA
<213> ORGANISM: Artificial Sequence
<220> FEATURE:
<223> OTHER INFORMATION: E8-R1

<400> SEQUENCE: 46
ataactgcac ccttggtctc                                         20

<210> SEQ ID NO 47
<211> LENGTH: 24
<212> TYPE: DNA
<213> ORGANISM: Artificial Sequence
<220> FEATURE:
<223> OTHER INFORMATION: SIRT7-3'UTR-312-335-WT

<400> SEQUENCE: 47
cgctcaccag gccagtctca gggc                                    24

<210> SEQ ID NO 48
<211> LENGTH: 24
<212> TYPE: DNA
<213> ORGANISM: Artificial Sequence
<220> FEATURE:
<223> OTHER INFORMATION: SIRT7-3'UTR-312-335-MT

<400> SEQUENCE: 48
cgctcaccag gccagtgagt ggca                                    24

<210> SEQ ID NO 49
<211> LENGTH: 21
<212> TYPE: DNA
<213> ORGANISM: Artificial Sequence
<220> FEATURE:
<223> OTHER INFORMATION: SIRT7-3'UTR-133-160-WT

<400> SEQUENCE: 49
agaggaagcc ccttgcactg c                                       21

<210> SEQ ID NO 50
<211> LENGTH: 21
<212> TYPE: DNA
<213> ORGANISM: Artificial Sequence
<220> FEATURE:
<223> OTHER INFORMATION: SIRT7-3'UTR-133-160-MT

<400> SEQUENCE: 50
agaggaagcc ccttcgtgtg c                                       21

<210> SEQ ID NO 51
<211> LENGTH: 20
<212> TYPE: DNA
<213> ORGANISM: Artificial Sequence
<220> FEATURE:
<223> OTHER INFORMATION: SIRT7-3'UTR-207-328-WT

<400> SEQUENCE: 51
accagcacac caggccagtc                                         20

<210> SEQ ID NO 52
<211> LENGTH: 20
<212> TYPE: DNA
<213> ORGANISM: Artificial Sequence
<220> FEATURE:

<223> OTHER INFORMATION: SIRT7-3'UTR-207-328-MT

<400> SEQUENCE: 52
accagcacac cagcggtgtc 20